(12) United States Patent
Dunn et al.

(10) Patent No.: US 10,603,385 B2
(45) Date of Patent: Mar. 31, 2020

(54) METHODS AND COMPOSITIONS FOR TEMPLATED ASSEMBLY OF NUCLEIC ACID SPECIFIC HETEROCOMPOUNDS

(71) Applicant: TRIBIOTICA LLC, Madison, WI (US)

(72) Inventors: Ian Dunn, Sydney (AU); Matthew Lawler, Madison, WI (US)

(73) Assignee: TriBiotica LLC, Madison, WI (US)

( * ) Notice: Subject to any disclaimer, the term of this patent is extended or adjusted under 35 U.S.C. 154(b) by 0 days.

(21) Appl. No.: 14/895,398

(22) PCT Filed: Jun. 4, 2014

(86) PCT No.: PCT/US2014/040822
§ 371 (c)(1),
(2) Date: Dec. 2, 2015

(87) PCT Pub. No.: WO2014/197547
PCT Pub. Date: Dec. 11, 2014

(65) Prior Publication Data
US 2016/0106854 A1    Apr. 21, 2016

Related U.S. Application Data

(60) Provisional application No. 61/831,133, filed on Jun. 4, 2013.

(51) Int. Cl.
*A61K 47/54*    (2017.01)
*A61K 39/00*    (2006.01)
(Continued)

(52) U.S. Cl.
CPC ........ *A61K 47/549* (2017.08); *A61K 39/0011* (2013.01); *C12N 15/1068* (2013.01);
(Continued)

(58) Field of Classification Search
CPC .............. A61K 47/549; A61K 39/0011; A61K 2039/5158; A61K 2039/6025;
(Continued)

(56) References Cited

U.S. PATENT DOCUMENTS 5,514,546 A   5/1996   Kool
5,858,731 A   1/1999   Sorge
(Continued)

FOREIGN PATENT DOCUMENTS

JP    H10512446    12/1998
JP    2009528988    8/2009
(Continued)

OTHER PUBLICATIONS

Blanco-Canosa and Dawson, An efficient Fmoc-SPPS approach for the generation of thioester peptide precursors for use in native chemical ligation, Angew Chem Int Ed Engl 2008 47(36):6851-6855.
(Continued)

*Primary Examiner* — Joseph G. Dauner
(74) *Attorney, Agent, or Firm* — Stradley Ronon Stevens & Young, LLP

(57) ABSTRACT

The present disclosure is directed methods and products for synthesizing and using targeted templated assembly reactants comprising at least one nucleic acid recognition moiety, at least one selectively-reactive moiety, and at least one effector partial moiety. The nucleic acid recognition moiety can bind a target nucleic acid sequence within a sample. The nucleic acid recognition moiety also can bind the selectively-reactive moiety. Additionally, the effector partial moiety can bind the selectively-reactive moiety to produce an active effector structure. Also disclosed are methods of
(Continued)

delivering the targeted templated assembly reactants and active effector structures formed from the targeted templated assembly reactants.

15 Claims, 15 Drawing Sheets

Specification includes a Sequence Listing.

(51) Int. Cl.
  *C12N 15/113* (2010.01)
  *C12N 15/11* (2006.01)
  *C12N 15/10* (2006.01)

(52) U.S. Cl.
  CPC ........ *C12N 15/111* (2013.01); *C12N 15/1131* (2013.01); *A61K 2039/6025* (2013.01); *C12N 2310/351* (2013.01); *C12N 2310/3513* (2013.01); *C12N 2310/3517* (2013.01); *C12N 2320/30* (2013.01)

(58) Field of Classification Search
  CPC . C12Q 1/6811; C12N 15/1068; C12N 15/111; C12N 15/1131; C12N 2310/3517; C12N 2310/3513; C12N 2320/30; C12N 2310/351

See application file for complete search history.

(56) References Cited

U.S. PATENT DOCUMENTS

| | | | |
|---|---|---|---|
| 2002/0172965 A1 | 11/2002 | Kamb et al. | |
| 2005/0026178 A1 | 2/2005 | Nilsen-Hamilton | |
| 2005/0048192 A1 | 3/2005 | Raines et al. | |
| 2005/0287548 A1* | 12/2005 | Bao | B82Y 5/00 435/6.11 |
| 2006/0099592 A1* | 5/2006 | Freskgard | C12N 15/1068 435/6.12 |
| 2006/0147963 A1 | 7/2006 | Barone et al. | |
| 2007/0099222 A1 | 5/2007 | Gee et al. | |
| 2007/0190597 A1 | 8/2007 | Agnew et al. | |
| 2008/0044834 A1* | 2/2008 | Heyduk | C12N 15/111 435/6.11 |
| 2008/0050731 A1 | 2/2008 | Agnew et al. | |
| 2008/0071074 A1 | 3/2008 | Skrzypczynski et al. | |
| 2009/0124571 A1 | 5/2009 | Morvan et al. | |
| 2010/0048866 A1 | 2/2010 | Raines et al. | |
| 2010/0055728 A1* | 3/2010 | Yang | C12Q 1/00 435/23 |
| 2012/0009566 A1* | 1/2012 | Soukka | C12Q 1/6818 435/5 |
| 2015/0203841 A1 | 7/2015 | Rasmussen | |
| 2016/0025726 A1 | 1/2016 | Altin et al. | |
| 2016/0106854 A1 | 4/2016 | Dunn et al. | |

FOREIGN PATENT DOCUMENTS

| | | |
|---|---|---|
| JP | 2014055167 | 3/2014 |
| WO | 0061775 A1 | 10/2000 |
| WO | 2004011486 | 2/2004 |
| WO | 2006058496 | 6/2006 |
| WO | 2011089393 A1 | 7/2011 |
| WO | 2012057689 | 5/2012 |
| WO | 2014197547 A1 | 11/2014 |
| WO | 2015122835 | 8/2015 |
| WO | 2016089958 | 6/2016 |
| WO | 2017049094 | 3/2017 |

OTHER PUBLICATIONS

Le Gall et al., Protable flanking sequences modulate CTL epitope processing, J Clin Invest 2007 117(11):3563-3575.
Roosild et al., Structure of anti-FLAG M2 Fab domain and its use in the stabilization of engineered membrane proteins, Acta Crystallogr Sect F Struct Biol Cryst Commun 2006 62(9):835-839.
Sletten et al., From mechanism to mouse: a tale of two bioorthogonal reactions, Acc Chem Res 2011 44(9):666-76.
Tam and Raines, Coulombic effects on the traceless Staudinger ligation in water, Bioorg Med Chem 2009 17 (3):1055-1063.
Tam et al., Water-soluble phosphinothiols for traceless Staudinger ligation and integration with expressed protein ligation, J Am Chem Soc 2007 129(37):11421-11430.
Imoto et al., DNA-templated click chemistry for creation of novel DNA binding molecules, Bioorganic & Medicinal Chem Lett 2008 18(20):5660-5663.
Walder et al., Complementary carrier peptide synthesis: general strategy and implications for prebiotic origin of peptide synthesis, PNAS 1979 76(1):51-55.
Pai et al., "Using RNA aptamers and the proximity ligation assay for the detection of cell surface antigens", Methods Mol Biol, 2009, 504, pp. 385-398.
Official Action dated Mar. 6, 2019 in related U.S. Appl. No. 15/529,807.
D.Y. Wu and B. Wallace "The Ligation Amplification Reaction (LAR)—Amplification of Specific DNA Sequences Using Sequential Rounds of Template-Dependent Ligation", Genomics, 1989, 4:560-569.
Bendifallah et al., "Evaluation of Cell-Penetrating Peptides (CPPs) as Vehicles for Intracellular Delivery of Antisense Peptide Nucleic Acid (PNA)", Bioconjugate Chem, 2006, 17, pp. 750-758.
Kazane, et al., "Self-Assembled Antibody Multimers Through Peptide Nucleic Acid Conjugation", JACS, 2012, 135, pp. 340-346.
Monroy-Contreras et al., "Molecular Beacons: Powerful Tools for Imaging RNA in Living Cells", J Nuc Acids, 2011, pp. 5-6.
Ponomarenko et al., "Recent advances in self-assembled fluorescent DNA structures and probes", Curr Top Med Chem, 2015, 15(13), pp. 1162-1178.
Zhao et al, "Solid-phase synthesis and evaluation of TAR RNA targeted beta-carboline-nucleoside conjugates", Organic and Biomolecular Chemistry, 2008, 6(20), pp. 3741-3750.
Niwayama et al., "A Pyrene Maleimide with a Flexible Linker for Sampling of Longer Inter-Thiol Distances by Excimer Formation", PLoS ONE, 2011, 6(10), e26691.
Clackson et al., "Redesigning an FKBP-ligand interface to generate chemical dimerizers with novel specificity", PNAS USA, 1998, 95(18):10437-10442.
Kalia et al., "Reactivity of Intein Thioesters: Appending a Functional Group to a Protein", ChemBioChem, 2006, 7:1375-1383.
Knecht et al., "Oligohis-tags: mechanisms of binding to Ni2+ surfaces", J Mol Recognit, 2009, 22:270-279.
Weisbrod et al., "Synthesis of Water-Soluble Phosphinophenol for Traceless Staudinger Ligation", Synlett, 2010, 5:787-789.
Overkamp et al., "Benchmarking various green fluorescent protein variants in Bacillus subtilis, *Streptococcus pneumoniae*, and Lactococcus lactis for live cell imaging", Appl Environ Microbiol, 2013, 79(20):6481-6490.
Paulmurugan et al., "Monitoring protein-protein interactions using split synthetic renilla luciferase protein-fragment-assisted complementation", Anal Chem, 2003, 75(7):1584-1589.
Official Action dated Dec. 6, 2019 in related U.S. Appl. No. 15/529,807.
Official Action dated Dec. 11, 2019 in related U.S. Appl. No. 15/601,449.

* cited by examiner

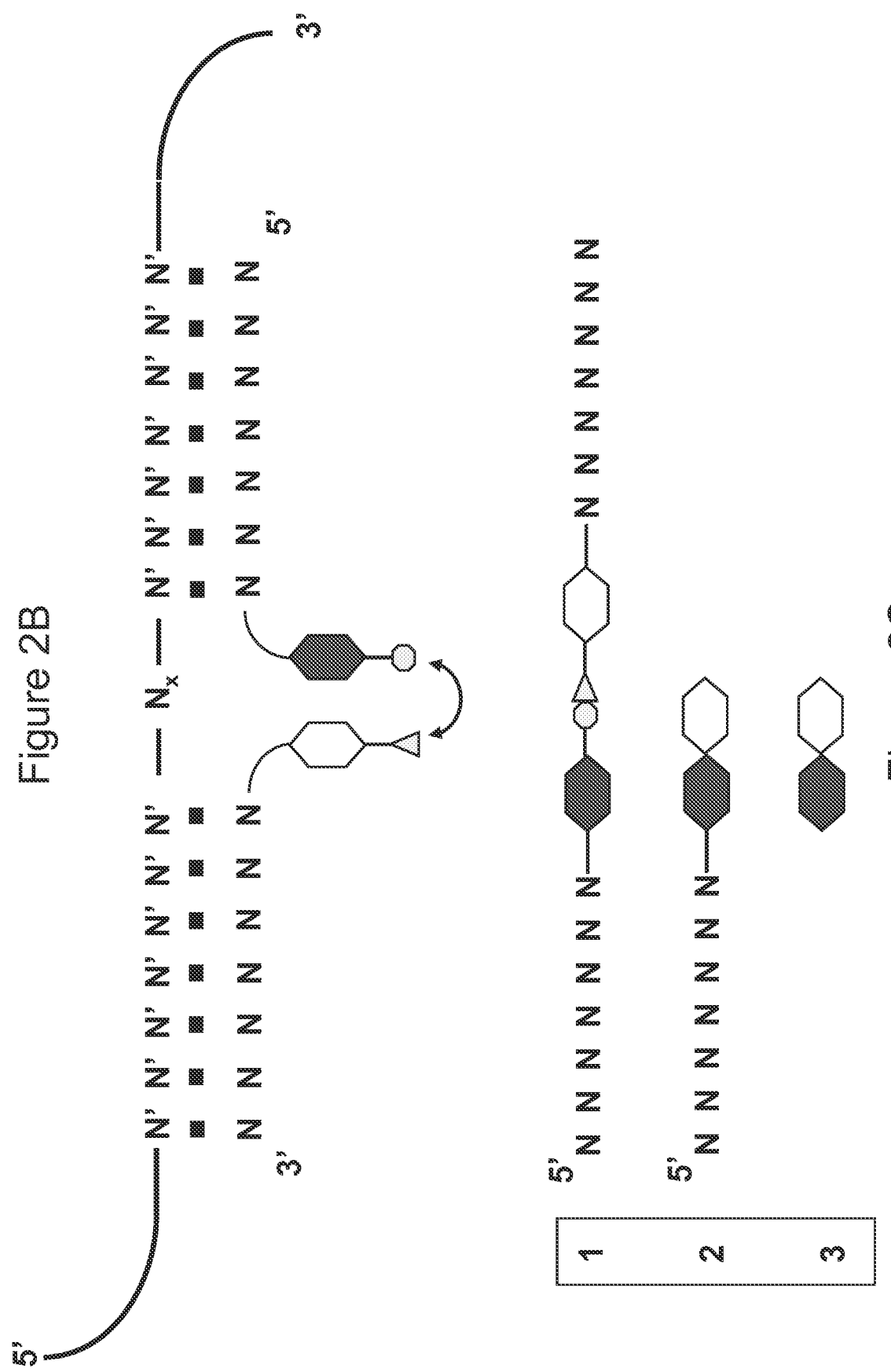

METHODS AND COMPOSITIONS FOR TEMPLATED ASSEMBLY OF NUCLEIC ACID SPECIFIC HETEROCOMPOUNDS

CROSS-REFERENCE TO RELATED APPLICATIONS

This application is a 35 U.S.C. § 371 national phase application of PCT Application No. PCT/US2014/40822, filed Jun. 4, 2014, which claims priority to U.S. Application No. 61/831,133, filed Jun. 4, 2013, each of which is incorporated herein by reference in its entirety.

FIELD

The present disclosure concerns methods of templated assembly and compositions of templated assembly reactants including nucleic acid-specific heterocompounds.

BACKGROUND

A goal of drug development is delivering potent bio-therapeutic interventions to pathogenic cells, such as virus infected cells, neoplastic cells, cells producing an autoimmune response, and other dysregulated or dysfunctional cells. Examples of potent bio-therapeutic interventions capable of combating pathogenic cells include toxins, pro-apoptotic agents, and immunotherapy approaches that re-direct immune cells to eliminate pathogenic cells. Unfortunately, developing these agents is extremely difficult because of the high risk of toxicity to adjacent normal cells or the overall health of the patient.

A method that has emerged to allow delivery of potent interventions to pathogenic cells while mitigating toxicity to normal cells is targeting of therapeutics by directing them against molecular markers specific for pathogenic cells. Targeted therapeutics have shown extraordinary clinical results in restricted cases, but are currently limited in their applicability due to a lack of accessible markers for targeted therapy. It is extremely difficult, and often impossible, to discover protein markers for many pathogenic cell types.

More recently, therapies targeted to nucleic acid targets specific to pathogenic cells have been developed. Existing nucleic acid-targeted therapies, such as siRNA, are able to down-modulate expression of potentially dangerous genes, but do not deliver potent cytotoxic or cytostatic interventions and thus are not particularly efficient at eliminating the dangerous cells themselves.

Hence, there exists a need to combat the poor efficacy and/or severe side effects of existing bio-therapeutic interventions.

SUMMARY

The present disclosure is directed to methods and products for making and using targeted templated assembly reactants. In one aspect, targeted templated assembly reactants can include at least one nucleic acid recognition moiety that binds a target nucleic acid sequence, at least one selectively-reactive moiety bound to the nucleic acid recognition moiety and at least one effector partial moiety, wherein the effector partial moiety and the selectively-reactive moiety are capable of binding to produce an active effector structure. In another aspect, targeted templated assembly reactants can include at least one nucleic acid recognition moiety, at least one bio-orthogonal moiety and at least one effector partial moiety. Also disclosed is a method of synthesizing a targeted templated assembly reactant by generating at least one nucleic acid recognition moiety that is capable of binding a target nucleic acid sequence, generating at least one selectively-reactive moiety that is capable of binding a corresponding selectively-reactive moiety, and generating at least one effector partial moiety that is capable of binding a corresponding effector partial moiety to produce an active effector structure. Methods of synthesizing an active effector structure also include generating at least two templated assembly reactants, contacting the targeted templated assembly reactants to a target nucleic acid sequence and producing an active effector structure. Methods of delivering at least two targeted templated assembly reactants to a pathogenic cell are also included herein. The methods can include administering a therapeutically effective amount of the targeted templated assembly reactants to the pathogenic cell, and producing at least one active effector structure in the pathogenic cell.

In some embodiments, the targeted templated assembly composition is disclosed. The nucleic acid recognition moiety can be a nucleic acid-binding oligomer and the nucleic acid oligomer that can hybridize to the target nucleic acid sequence. Examples of such oligomers can include an oligomer selected from the group consisting of DNA nucleotides, RNA nucleotides, phosphorothioate-modified nucleotides, 2-O-alkylated RNA nucleotides, halogenated nucleotides, locked nucleic acid nucleotides (LNA), peptide nucleic acids (PNA), morpholino nucleic acid analogues (morpholinos), pseudouridine nucleotides, xanthine nucleotides, hypoxanthine nucleotides, 2-deoxyinosine nucleotides, other nucleic acid analogues capable of base-pair formation, and combinations thereof. The nucleic acid-binding moiety can bind a target nucleic acid sequence selected from the group consisting of an oncogene, a mutant gene, an oncoviral gene, a viral nucleic acid sequence, a microbial nucleic acid sequence, a differentially expressed gene, and a fragment, portion or a nucleic acid gene product thereof.

In some embodiments, the selectively-reactive moiety binds to the nucleic acid recognition moiety. The selectively-reactive moiety can be linked to the nucleic acid recognition moiety. The selectively-reactive moiety can also be biologically inert, such as a bio-orthogonal reactive molecule. Examples of selectively-reactive moieties can include an azide, a cyclooctyne, a nitrone, a norbornene, an oxanorbornadiene, a phosphine, a dialkyl phosphine, a trialkyl phosphine, a phosphinothiol, a phosphinophenol, a cyclooctene, a nitrile oxide, a thioester, a tetrazine, an isonitrile, a tetrazole, a quadricyclane, and derivatives thereof. The effector partial moiety can also include a first effector partial moiety that binds with the selectively-reactive moiety and a second effector partial moiety that binds with the first effector partial moiety to produce the active effector structure. The effector partial moiety can also include a chemical linker capable of interacting with the selectively-reactive moiety to produce the active effector structure. The effector partial moiety can be a peptide, a non-active portion of a peptidomimetic structure, a non-active portion of a drug, or other bioactive compound that is less than 20 kDa.

In some embodiments, an active effector structure is disclosed. The active effector can include a product of a reaction of at least one selectively-reactive moiety structure and at least one effector partial moiety bound to the selectively-reactive moiety. The active effector structure can also include at least one nucleic acid recognition moiety bound to the reaction product. The active effector can regulate at least one of enzyme activity, gene/protein expression such as modulating expression of a target gene, molecular signaling, and molecular interaction and/or possess targeted activity as compared to an activity of the effector partial moiety. The active effector can also induce at least one of an immune response, programmed cell death, apoptosis, programmed non-specific or programmed necrosis, lysis, growth inhibition, inhibition of viral infection, inhibition of viral replication, inhibition of oncogene expression, modification of gene expression, inhibition of microbial infection, and inhibition of microbe replication. In one embodiment, the active effector structure is an antibody.

The chemical linker can also be located between the nucleic acid recognition moiety and the selectively-reactive moiety, and/or between the selectively-reactive moiety and the effector partial moiety and/or be a flexible moiety, a cleavage site, and/or a chemical modification site. The chemical linker can functionalize the nucleic acid recognition moiety, the bio-orthogonal moiety, and/or the effector partial moiety by improving at least one of solubility, hydrophobicity, charge, cell-permeability, toxicity, bio-distribution, and stability of the targeted templated assembly composition. Examples of chemical linkers can include of an alkyl group, an alkenyl group, an amide, an ester, a thioester, a ketone, an ether, a thioether, a disulfide, an ethylene glycol, a cycloalkyl group, a benzyl group, a heterocyclic group, a maleimidyl group, a hydrazone, a urethane, azoles, an imine, a haloalkyl, a carbamate, and combination thereof. The target nucleic acid sequence can include a cancer-specific nucleic acid sequence, a viral nucleic acid sequence, a microbial-specific nucleic acid sequence, a differentially expressed gene, a disease-specific nucleic acid sequence, and a fragment, portion or a nucleic acid gene product thereof.

In some embodiments, a method of synthesizing a templated assembly reactant and a method of synthesizing an active effector structure are disclosed. The methods can also include determining competency of the nucleic acid recognition moiety, selectively-reactive moiety, and the effector partial moiety to produce the active effector structure.

In some embodiments, a method of delivering at least two targeted templated assembly reactants to a pathogenic cell is disclosed. The method can also include detecting the presence or absence of the target nucleic acid sequence prior to administering the targeted templated assembly composition. In another embodiment, the method includes inducing at least one of programmed cell death of the pathogenic cell, apoptosis of the pathogenic cell, non-specific or programmed necrosis of the pathogenic cell, lysis of the pathogenic cell, and growth inhibition of the pathogenic cell.

The administered composition can also include two or more sets of templated assembly reactants, where a set of template assembly reactants includes a targeted templated assembly reactant and a corresponding targeted templated assembly reactant. The set can also include two or more sets of nucleic acid recognition moieties that are capable of binding two or more target nucleic acid sequences Two or more target nucleic acid sequences may be found within the same gene transcript, or on distinct and separate transcripts. Two or more sets of corresponding templated assembly reactants recognizing distinct nucleic acid target sequences within the same cellular transcript may independently carry the same effector partial structures that react to form additional copies of the same effector products in a template-directed manner.

In some embodiments, two or more sets of corresponding templated assembly reactants recognizing distinct and separate nucleic acid target sequences may carry the same effector partial structures that react to form effector products in a template-directed manner.

In some embodiments, two or more sets of corresponding templated assembly reactants recognizing the same cellular nucleic acid target sequences may carry distinct effector partial structures that react to form distinct effector products in a template-directed manner. Two or more sets of templated assembly reactants can include effector partial moieties capable of producing two or more active effector structures.

In some embodiments, two or more sets of corresponding templated assembly reactants recognizing distinct and separate nucleic acid target sequences may carry the distinct effector partial structures that react to form distinct effector products in a template-directed manner. In the embodiments where two or more sets of effector partial moieties are included in the composition, two or more active effector structures can be produced to induce two or more effector activities.

The pathogenic cell can be a virus infected cell, a tumor cell, and a cell infected with a microbe, or a cell that produces a molecule that leads to a disease, such as an cell that produces an antibody that induces allergy, anaphylaxis or autoimmune disease, or a cytokine that mediates a disease. In embodiments where the pathogenic cell is a virus infected cell, the method can further include inducing at least one of programmed cell death of the virus infected cell, apoptosis of the virus infected cell, non-specific or programmed necrosis of the virus infected cell, lysis of the virus infected cell, inhibition of viral infection, and inhibition of viral replication. In embodiments where the pathogenic cell is a tumor cell, the method can further include inducing at least one of programmed cell death of the tumor cell, apoptosis of the tumor cell, non-specific or programmed necrosis of the tumor cell, lysis of the tumor cell, inhibition of the tumor cell growth, inhibition of oncogene expression in the tumor cell, and modification of gene expression in the tumor cell. In embodiments where the pathogenic cell is a microbe-infected cell, the method can further include inducing at least one of programmed cell death of the microbe-infected cell, apoptosis of the microbe-infected cell, non-specific or programmed necrosis of the microbe-infected cell, lysis of the microbe-infected cell, inhibition of microbial infection, and inhibition of microbe replication. In embodiments where the pathogenic cell produces disease-mediating molecules, the method can include inducing at least one of programmed cell death of the disease-inducing cell, apoptosis of the disease-inducing cell, necrosis of the disease-inducing cell, lysis of the disease-inducing cell, and inhibition of production of disease mediating molecules.

BRIEF DESCRIPTION OF THE DRAWINGS

The appended drawings have been included herein so that the above-recited features, advantages and objects of the disclosure will become clear and can be understood in detail. These drawings form a part of the specification. It is to be noted, however, that the appended drawings illustrate embodiments of the disclosure and should not be considered to limit the scope of the disclosure.

FIG. 1A shows interaction between two nucleic acid recognition moieties on a target nucleic acid template, indicating distinct effector partial moieties (A and B) and distinct selectively-reactive moieties (1 and 2).

FIG. 1B shows a tripartite assembly, using three effector partial structures (A, B, C) and two distinct selectively reactive moieties (1 and 2). The 5' end of one nucleic acid recognition moiety is linked to effector partial moiety B bearing a dual modification with selectively-reactive moiety 2, to facilitate the formation of a tripartite reaction product.

FIG. 1C depicts templated assembly through a unimolecular arrangement, where the 5' and 3' ends of a single nucleic acid recognition moiety are modified with selectively reactive moieties, and the latter becomes spatially juxtaposed only in the presence of a specific nucleic acid target.

FIG. 2B shows hybridization of each templated assembly reactant onto a target RNA such that the bio-orthogonal reactive moieties are juxtaposed for reaction. N' denotes complementary nucleobases in the target RNA strand for each nucleobase N in each templated assembly reactant.

FIG. 2C shows examples of templated assembly ligation products, and assembled effector structures: 1) non-traceless ligation, 2) traceless ligation, and 3) traceless ligation and free effector structure after chemical or enzymatic cleavage from carrier nucleic acid.

DESCRIPTION OF THE DISCLOSURE

Figure 1A:
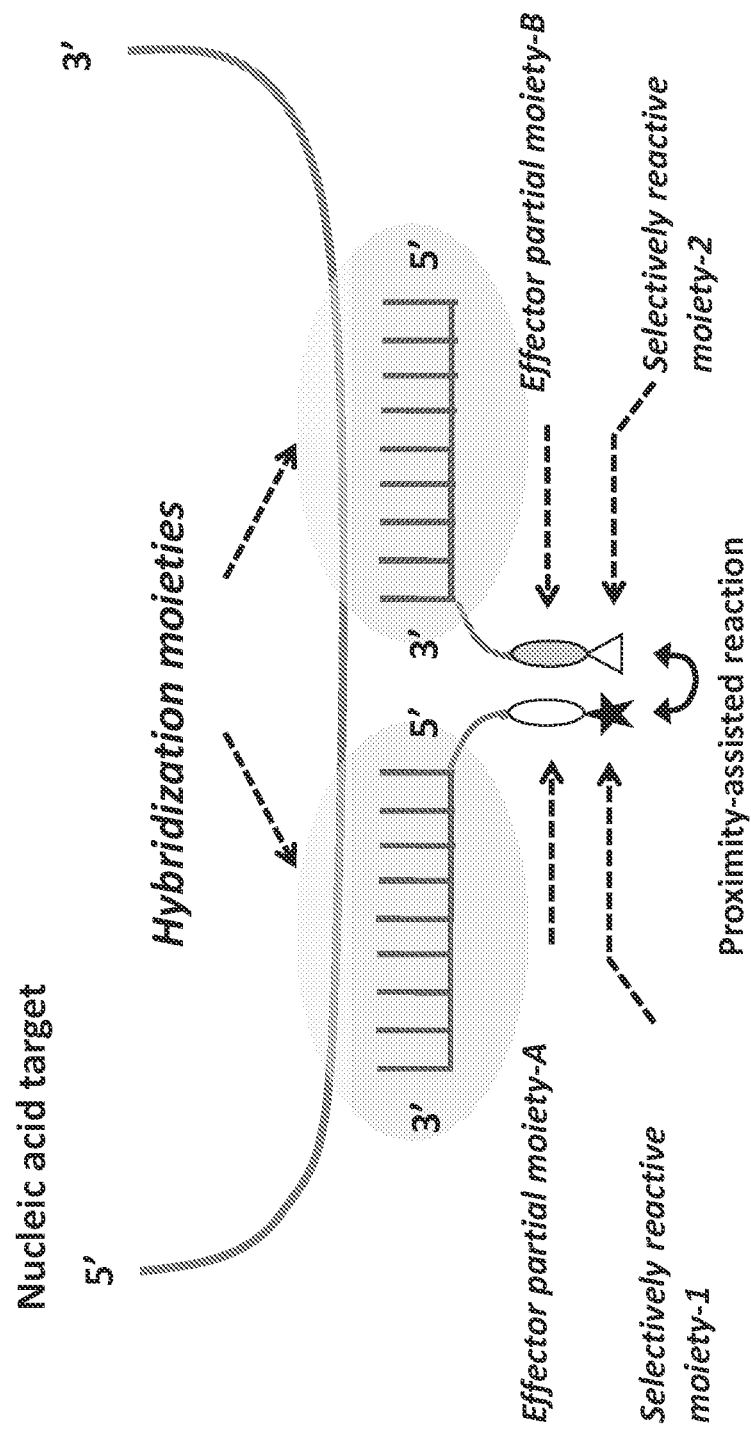
FIG. 1A is an illustration of an embodiment of templated assembly reactants including two separate compounds.

Certain exemplary embodiments will now be described to provide an overall understanding of the principles of the structure, function, manufacture, and use of the compositions and methods disclosed herein. One or more examples of these embodiments are illustrated in the accompanying drawings. Those skilled in the art will understand that the compositions and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Conventional targeted therapies are limited by availability of target antigens, ability to down-modulate expression of pathogenic genes or efficiency of eliminating the pathogenic cells themselves. In contrast, the disclosed methods and compositions avoid many of the most common pitfalls associated with these therapeutics. Targeting specific genetic templates in the pathogenic cells, the disclosed methods and compositions avoid off-target toxicity and enhance pathogen-specific reactivity. Unlike immunotherapy protocols, the disclosed disclosure utilizes the pathogenic cell's unique transcriptome to produce novel molecules that can mediate desirable outcomes. The cells are accordingly targeted for directed intervention, such as by self-destruction or immunotherapeutic destruction by other cells, without inducing toxicity against normal cells.

Nucleic Acid Templated Assembly

The current disclosure enables one to produce desired chemical structures selectively in the presence of specific nucleic acid sequences, even in the presence of other biological materials. The disclosure describes templated assembly of two or more reactants on target nucleic acids, which generates an active effector product where target nucleic acids are present. Nucleic acid templated assembly improves reaction kinetics by increasing local effective concentration of corresponding reactants when target nucleic acids are present, and may also lower the activation barrier to product formation by correctly positioning reactants to participate in the reaction. The disclosed disclosure enables targeted therapy for diseases such as cancers and immune system disorders by producing active effector structures only where the target nucleic acid is present.

The basic scheme of nucleic acid templated assembly is depicted below:

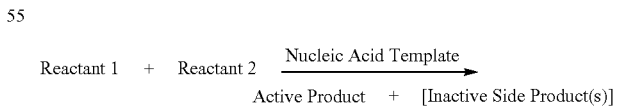

Reactant 1 + Reactant 2 $\xrightarrow{\text{Nucleic Acid Template}}$ Active Product + [Inactive Side Product(s)]

Nucleic acid templated assembly brings two or more templated assembly reactants into proximity to generate a templated assembly ligation product. The term "templated assembly ligation product," as used herein, refers to the product structure or structures formed by interaction, binding or reaction of one or more nucleic acid templated assembly reactants. A templated assembly ligation product may include an active effector product capable of producing a desired biological activity. Templated assembly ligation product formation is facilitated by the individual templated assembly reactants being assembled in a position- and/or orientation-specific manner through binding interactions, such as hybridization and annealing, with a target nucleic acid. Templated assembly reactants that come together on a single target template to take part in a templated assembly reaction are referred to herein as a "set of corresponding reactants" or "corresponding templated assembly reactants." A set of corresponding templated assembly reactants bind in a sequence-specific manner to spatially proximate parts of a nucleic acid target template, and readily react with each other to produce templated assembly ligation products including an active effector structure.

A templated assembly reactant can include a nucleic acid recognition moiety to direct sequence-specific binding to the target template at a position spatially proximate to a corresponding reactant. A templated assembly reactant can also include a selectively-reactive moiety, such that the selectively-reactive moieties of a set of corresponding reactants participate readily in reactions with each other, but may not readily react with other compounds in the pathogenic cell or biological sample. Unlike other templated assembly systems which do not permit reactions to occur in complex environments such as living cells, utilization of selectively-reactive moieties can allow nucleic acid templated assembly to occur in highly complex chemical environments, including living cells. A templated assembly reactant can also include an effector partial moiety, such that when a set of corresponding reactants participates in a target templated reaction, an active effector product can be generated. An effector partial moiety may include some or all of the nucleic acid recognition moiety and the selectively-reactive moiety. A templated assembly reactant may optionally include chemical linkers or accessory groups, which may facilitate synthesis of the reactant, improve its chemical or biological properties, and/or introduce additional functionality to the reactant.

An example of a practical advantage to the templated assembly approach disclosed herein is the intrinsic modularity of the molecules. For example, if a particularly potent effector molecule can be produced as a result of the assembly of the effector partial moieties into the full effector molecule, the same effector molecule can also be produced through templating on a wide variety of distinct nucleic acid targets. This can be achieved by binding the same effector partial structures linked to selectively reactive groups to different nucleic acid recognition moieties, whose binding to a designated target nucleic acid brings the selectively reactive groups into spatial proximity. By such means the full effector molecule can be assembled by binding to the nucleic acid target to produce the same final biological effect. In addition, several different transcripts can be targeted within the same cell to avoid templating failure through possible loss of, or acquired inaccessibility towards, a single specific target transcript. The same effector product molecules can, accordingly, be synthesized on different nucleic acid targets within the same target cell. In a similar manner, different effector products can be assembled on the same transcript to avoid possible resistance to any given effector mechanism that can be produced within a target cell. Thus, by identifying a variety of target transcripts within a pathogenic cell, it is possible to use the same effector assembly for cellular elimination, or to assemble different effector products on the same transcript. The advantage of such modularity provides flexibility to the templated assembly technology not seen in existing bio-therapeutic interventions.

Figure 1B:
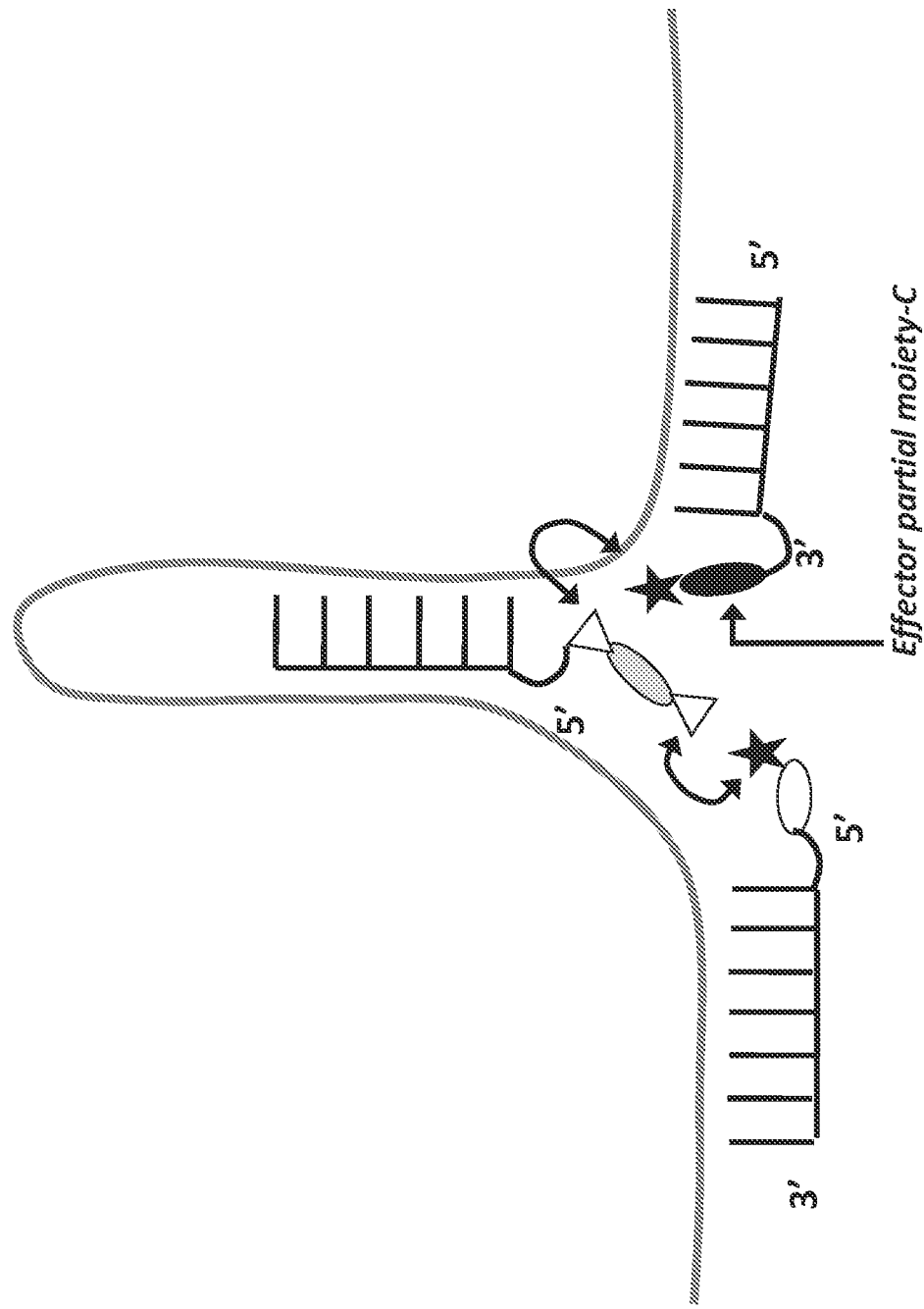
FIG. 1B is an illustration of another embodiment of templated assembly including two or more separate compounds.
Figure 1C:
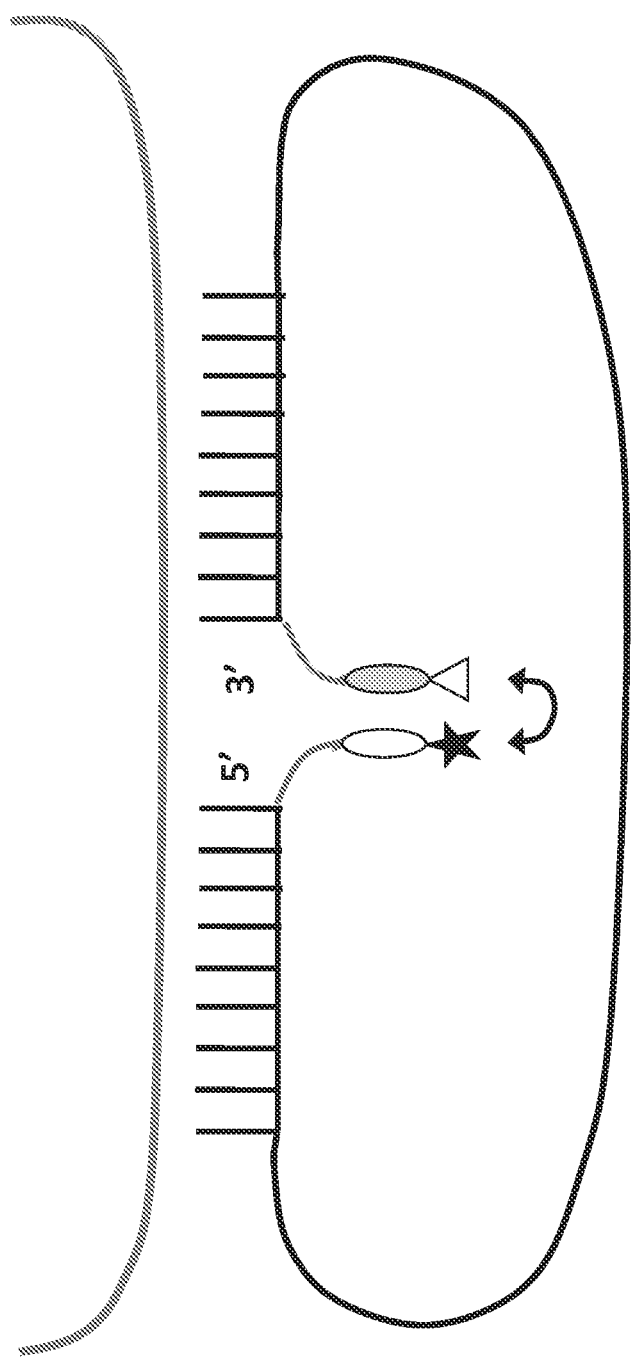
FIG. 1C is an illustration of another embodiment of templated assembly with templated assembly reactants connected by a chemical linker.

In some embodiments, a set of corresponding templated assembly reactants is comprised of templated assembly reactants that are two or more separate compounds, as shown in FIG. 1A and FIG. 1B. In another embodiment, a set of corresponding templated assembly reactants may be connected by a chemical linker in such a way as the corresponding reactants can be physically connected but maintain a spatial separation unless a target template is present to bring them into proximity for a templated assembly reaction, as shown in FIG. 1C.

The disclosure generally describes methods and compositions of templated assembly reactants comprising at least one nucleic acid recognition moiety, at least one selectively-reactive moiety, and at least one effector partial moiety.

The disclosure further describes methods for administering a set of corresponding templated assembly reactants to generate active effector structures in the presence of target nucleic acid template. Exemplary active effector structures capable of producing desired biological activity are also described.

Figure 2A:
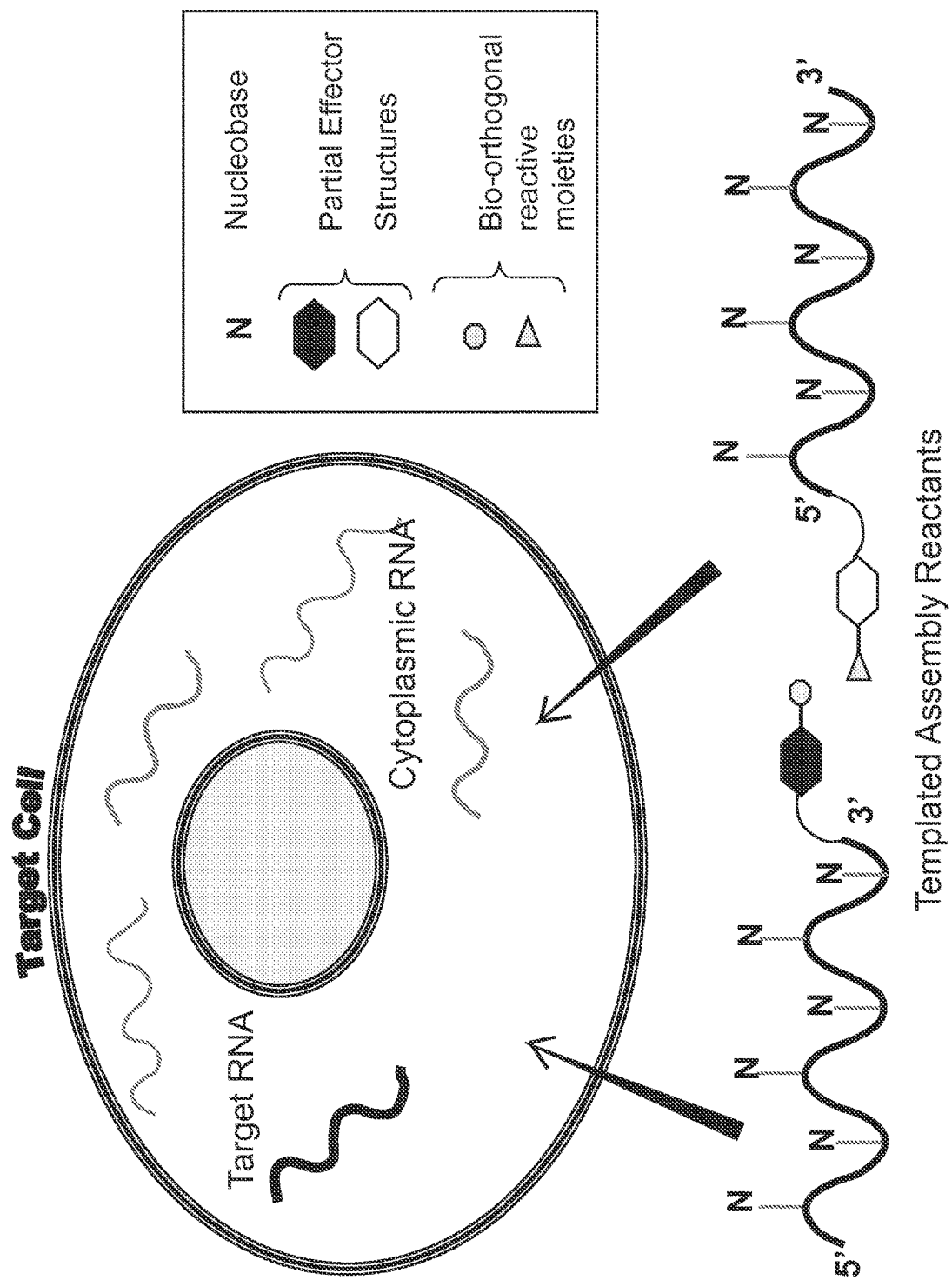
FIG. 2A is an illustration of a cellular target compartment containing a specific target RNA molecule (representative of any general targeted nucleic acid), and two participating templated assembly reactants, bearing effector partial structures and 5' and 3' bio-orthogonal reactive moieties. The templated assembly reactants are co-delivered into the target compartment for access to target RNA.

The general approach is depicted in FIG. 2A and examples of templated assembly products are shown in FIGS. 2B and 2C. Further details of the methods and compositions are described in the following sections.

Design and Synthesis of Nucleic Acid Templated Assembly Reactants

To generate a desired activity selectively in target cells, it is necessary to synthesize templated assembly reactant compounds that: a) in the presence of target nucleic acid, produce an active effector product that generates the desired activity; b) do not produce the active effector product or appreciable amounts of activity in the absence of target nucleic acid; and c) are not depleted by unproductive side-reactions in the presence of natural biomolecules. Templated assembly reactant compounds with these properties can be synthesized by carrying out the following steps, where the order of the steps may be altered to suit particular cases:

Identifying a suitable target nucleic acid template in pathogenic cells or sample material.

Determining a suitable active effector structure that can produce a desired effect in pathogenic cells or sample material.

Determining a templating strategy.

Designing and synthesizing nucleic acid recognition moieties that can bind the target nucleic acid template.

Designing and synthesizing selectively reactive moieties compatible with producing the suitable active effector structure.

Designing and synthesizing effector partial moieties compatible with producing the suitable active effector structure.

Synthesizing the complete nucleic acid templated assembly reactant(s).

Figure 3:
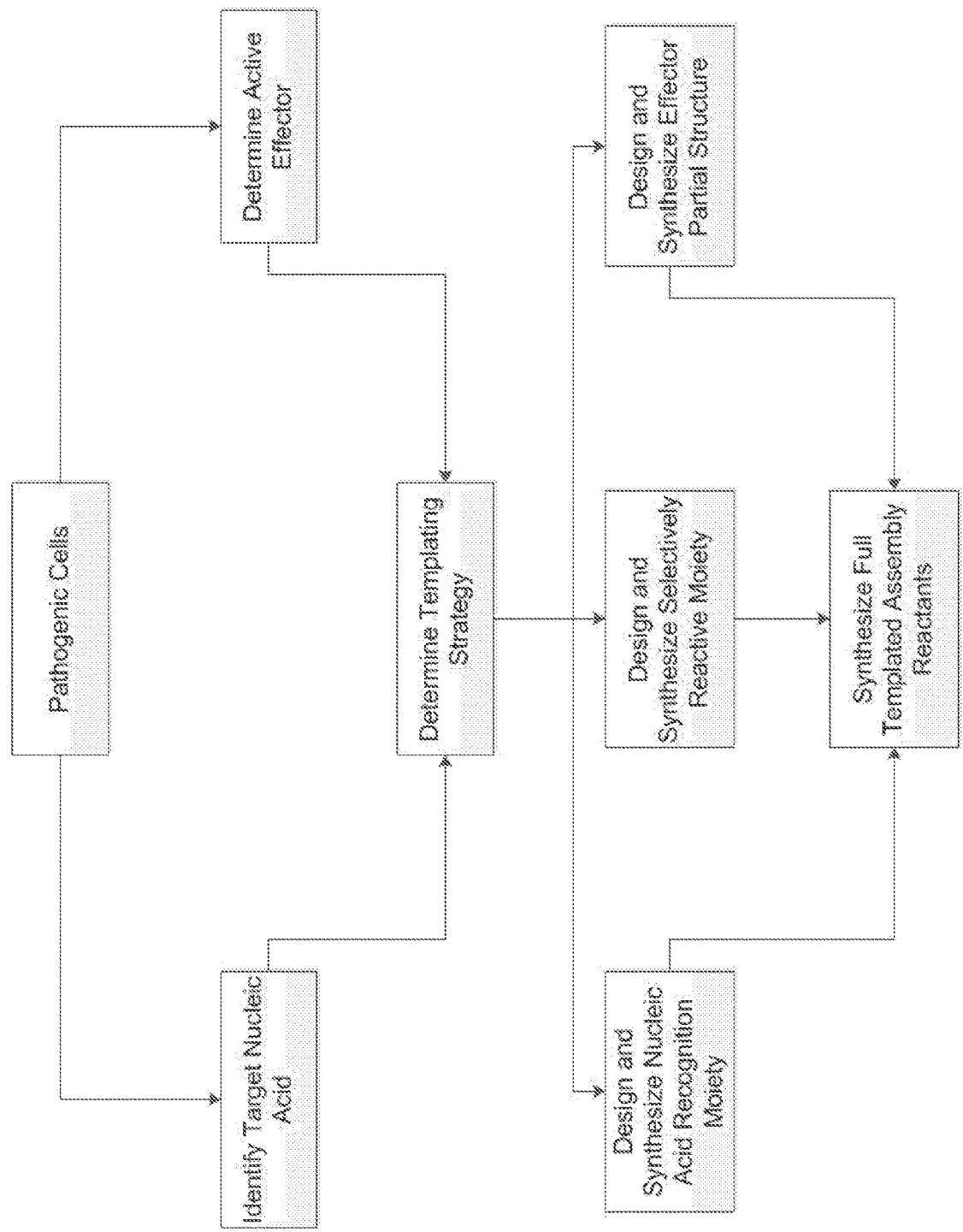
FIG. 3 is a flow diagram of the steps of templated assembly reactant synthesis.
Figure 4:
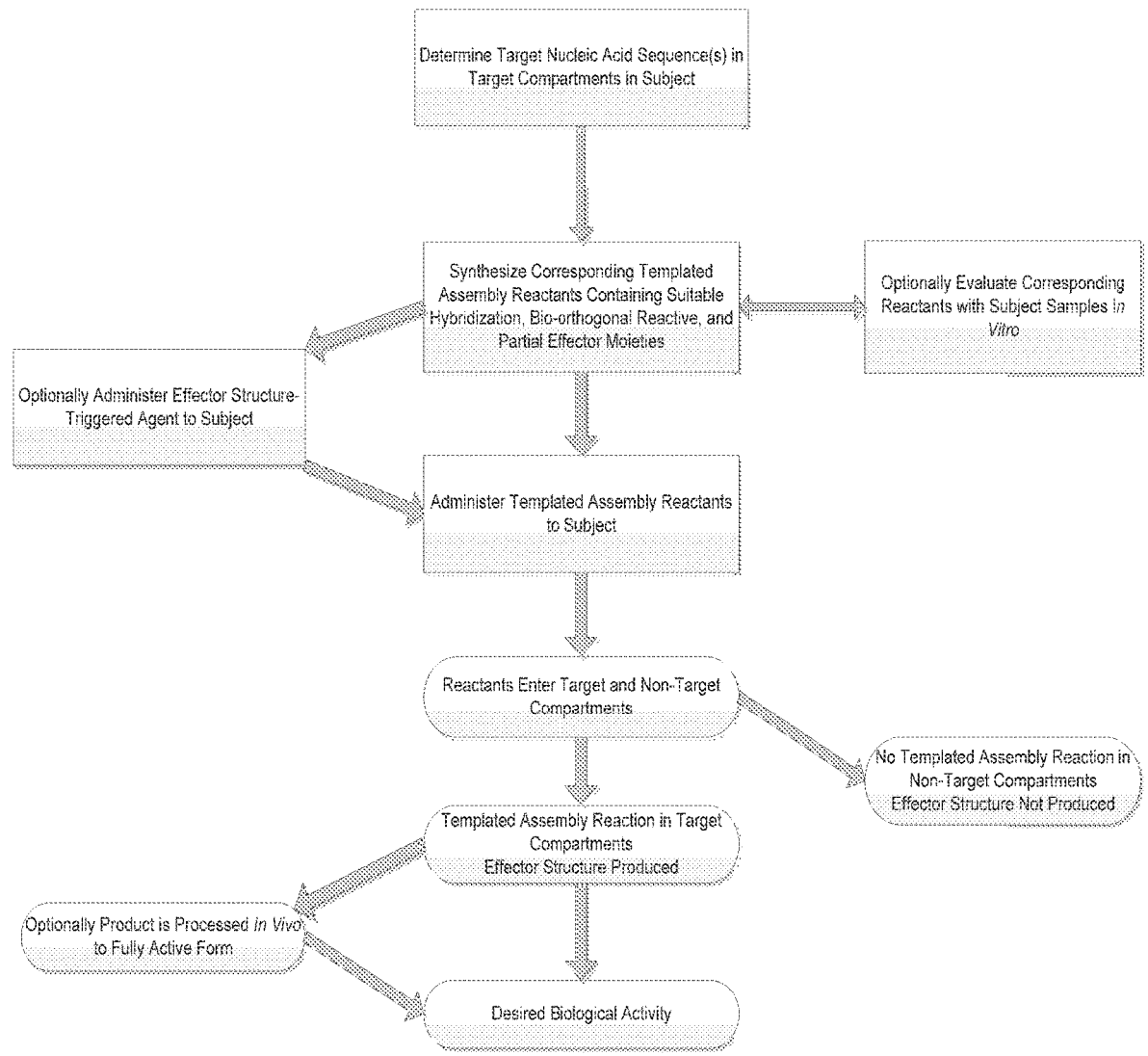
FIG. 4 shows a flowchart for a method of generating desired biological activity utilizing nucleic acid templated assembly. Boxes represent steps requiring activity on the part of the practitioner; ovals represent steps that occur spontaneously after administration.

FIG. 3 depicts a flowchart of the steps of templated assembly reactant synthesis process. Details of each of these steps are described in the following sections.

Target Nucleic Acids

Any nucleic acid can be a possible target nucleic acid for nucleic acid templated assembly provided that at least some sequence information is available, sufficient to bind nucleic acid recognition moiety either directly or indirectly. Some non-limiting examples of nucleic acid recognition moiety units can include oligonucleotides, peptide nucleic acid oligomers, and morpholino oligomers. Some non-limiting examples of target nucleic acid sequences can include mRNA, genomic or organellar DNA, episomal or plasmid DNA, viral DNA or RNA, miRNA, rRNA, snRNA, tRNA, or any other biological or artificial nucleic acid sequence.

In some embodiments, the target nucleic acid can be present in a target compartment but absent in a non-target compartment. An example of this embodiment includes nucleic acid sequences present in a pathogenic or diseased cell, but absent in a healthy cell. The term "pathogenic cell" as used herein can refer to a cell that is capable of causing or promoting a diseased or an abnormal condition, such as a cell infected with a virus, a tumor cell, and a cell infected with a microbe.

Any cell, virus, tissues, spatial regions, lysate, or other subcomponent of a sample that contains a target nucleic acid can provide the target nucleic acid. Target compartments that contain the target nucleic acid can include, but are not limited to, pathogenic cells, cancer cells, viruses, host cells infected by a virus or other pathogen, or cells of the immune system that are contributing to autoimmunity such as cells of the adaptive or innate immune systems, transplant rejection, or an allergic response. In one embodiment, a target nucleic acid can be present in a virus or cell infected by a virus, but absent in healthy cells. Some non-limiting examples of virus can include DNA viruses, RNA viruses, or reverse transcribing viruses. In one embodiment, a target nucleic acid can be present in a tumor or cancerous cell, but absent in healthy cells. Some non-limiting examples of cancers can include those caused by oncoviruses, such as the human papilloma viruses, Epstein-Barr virus, hepatitis B virus, hepatitis C virus, human T-lymphotropic viruses, Merkel cell polyoma virus, and Kaposi's sarcoma-associated herpesvirus. In another embodiment, a target nucleic acid can be present in an infectious agent or microbe, or a cell infected by an infectious agent or microbe but is absent in healthy cells. Some non-limiting examples of infectious agents or microbes can include viruses, bacteria, fungi, protists, prions, or eukaryotic parasites.

The target nucleic acid sequence can also be a fragment, portion or part of a gene, such as an oncogene, a mutant gene, an oncoviral gene, a viral nucleic acid sequence, a microbial nucleic acid sequence, a differentially expressed gene, and a nucleic acid gene product thereof.

Some non-limiting examples of virus-specific target nucleic acids can include sequences present in DNA viruses, RNA viruses, or reverse transcribing viruses. Some non-limiting examples of cancer-specific nucleic acids can include sequences derived from oncoviruses, including, but not limited to, human papilloma virus, Epstein-Barr virus, hepatitis B virus, hepatitis C virus, human T-lymphotropic virus, Merkel cell polyoma virus, and Kaposi's sarcoma-associated herpesvirus. Examples of cancer-specific target nucleic acids can include mutant oncogenes, such as mutated ras, HRAS, KRAS, NRAS, BRAF, EGFR, FLT1, FLT4, KDR, PDGFRA, PDGFRB, ABL1, PDGFB, MYC, CCND1, CDK2, CDK4, or SRC genes; mutant tumor suppressor genes, such as TP53, TP63, TP73, MDM1, MDM2, ATM, RB1, RBL1, RBL2, PTEN, APC, DCC, WT1, IRF1, CDK2AP1, CDKN1A, CDKN1B, CDKN2A, TRIM3, BRCA1, or BRCA2 genes; and genes expressed in cancer cells, where the gene may not be mutated or genetically altered, but is not expressed in healthy cells of a sample at the time of administration, such as carcinoembryonic antigen.

In some embodiments, the target nucleic acid can be present in a differential amounts or concentrations in the target compartments as compared to the non-target compartments. Examples can include, but are not limited to, genes expressed at a different level in cancer cells than in healthy cells, such as myc, telomerase, HER2, or cyclin-dependent kinases. In one embodiment, the target nucleic acid sequence can be a gene that is at least 1.5× fold differentially expressed in the target versus the non-target compartments. Some examples of these can include, but are not limited to, genes related to mediating Type I allergic responses, for which target RNA molecules contain immunoglobulin epsilon heavy chain sequences; genes expressed in T cell subsets, such as specific T cell receptors (TCRs) which recognize self-antigens in the context of particular major histocompatibility (MHC) proteins like proinsulin-derived peptide and clonally-specific mRNAs containing α or β variable-region sequences, derived from diabetogenic CD8+ T cells; and cytokines whose production may have adverse outcomes through exacerbation of inflammatory responses, including but not limited to TNF-alpha, TNF-beta, IL-1, IL-2, IL-4, IL-6, IL-8, IL-10, IL-12, IL-15, IL-17, IL-18, IL-21, IL-22, IL-27, IL-31, IFN-gamma, OSM, and LIF.

In some embodiments, a target nucleic acid is present in target compartments and an acceptable subgroup of non-target compartments, but not in a different or distinct subgroup of non-target compartments. Some non-limiting examples can include genes expressed in cancer cells and limited to classes of healthy cells, such as cancer-testis antigens, survivin, prostate-specific antigen, carcinoembryonic antigen (CEA), alpha-fetoprotein and other onco-fetal proteins. Also, many tissues and organs are not essential to otherwise healthy life in the face of serious disease. For example, melanocyte antigens, such as Melan-A/MART-1 and gp100 are expressed on many malignant melanomas as well as normal melanocytes, and therapies that target these antigens can destroy both tumors and normal melanocytes, resulting in vitiligo, but major tumor reduction. Likewise, the reproductive organs may be surgically removed, such as testis, ovary and uterus, as well as associated organs such as breast and prostate may be targeted when tumors of these tissues arise, and destruction of normal tissues within these organs may be a tolerable consequence of therapy. Furthermore, some cells that produce hormones, such as thyroxine and insulin can be replaced with the relevant protein, allowing potential targeting of normal cells that may exist in the presence of tumors of these origins.

Target nucleic acids can also include novel sequences, not previously identified. In one embodiment, a sample or samples can be evaluated by sequence analysis, such as next-generation sequencing, whole-transcriptome (RNA-seq) or whole-genome sequencing, microarray profiling, serial analysis of gene expression (SAGE), to determine the genetic makeup of the sample. Target nucleic acid sequences can be identified as those present in target compartments, but not present in non-target compartments, or present in differential amounts or concentrations in target compartments as compared to non-target compartments. Sequences identified by this method can then serve as target nucleic acids.

Determine Effector Structure

The effector structure is the trigger that drives a desired action in the sample. Some examples of desired effector activity can include, but are not limited to, inducing an immune response, programmed cell death, apoptosis, non-specific or programmed necrosis, lysis, growth inhibition, inhibition of viral infection, inhibition of viral replication, inhibition of oncogene expression, modification of gene expression, inhibition of microbial infection, and inhibition of microbe replication, as well as combinations of these biological activities. In another embodiment, the effector structure can serve as a ligand for an antibody to induce an immune response at the site of the pathogenic cells, or to localize antibody-directed therapies—such as an antibody bearing a therapeutic payload—to the site of the pathogenic cells. In another embodiment, the effector structure can modulate expression of a target gene. In another embodiment, the effector structure can regulate enzyme activity, gene/protein expression, molecular signaling, and molecular interaction An effector structure is a product of a combination of templated assembly reactants, or a combination of portions of templated assembly reactants, that produces a desired activity in a sample. The active effector structure can possess a targeted activity or an elevated level of activity as compared to either or both of the effector partial moieties individually. In one embodiment, the active effector structure can possess a new or substantially different activity than the individual moieties, as compared to either or both of the effector partial moieties individually.

A diverse array of effector structures may be produced by nucleic acid templated assembly. Any active product may serve as an effector structure as long as such a structure can be produced by the templated assembly of relatively inactive precursors that can be combined by reaction of corresponding selectively-reactive groups may serve as an effector structure. Thus, any compound that may be reconstituted from separate portions by formation of an amide bond, triazole linkage, phosphine oxide linkage, or other bio-orthogonal ligation product as described herein may serve as an active effector structure. Furthermore, such compounds can be assembled on virtually any accessible nucleic acid template, thus allowing assembly in a very diverse set of samples.

General forms of effector structures include but are not limited to:

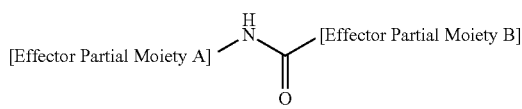

Amide-linked Effector Structure created by a non-traceless bio-orthogonal reaction.

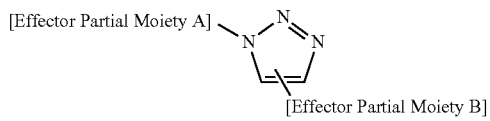

Triazole-linked effector structure produced by an azide-alkyne bio-orthogonal reaction.

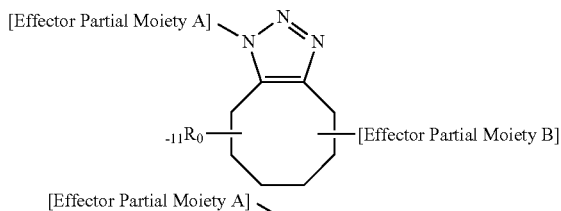

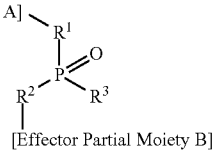

Phosphine oxide-linked effector structures produced by non-traceless Staudinger ligation bio-orthogonal reactions.

Active effector structures can also include proteins, peptides containing standard or non-standard amino acids, peptidomimetic structures, and drugs or other bioactive compounds that permit or require the interaction or incorporation of the effector structure.

In some embodiments, effector structures may be liberated from the other moieties in the templated assembly product by cleavage of the bonds connecting the effector structure to the remainder of the product. Cleavage may be achieved by hydrolysis of the connecting bonds, or by enzymatic cleavage by proteins or other compounds endogenous to the sample. Non-limiting examples of these cleavable bonds include esters, thioesters, imines, hydrazones, cleavage motifs of cellular proteases, or substrates of cellular enzymes. Cleavable groups may be introduced by their incorporation into a templated assembly reactant moiety, linker, or accessory group during synthesis, or may be generated during the ligation reaction. In one embodiment, post-ligation cleavage or other in situ chemical modification of the effector structure may be required for the effector structure to trigger a desired activity.

An effector structure may also trigger activity by acting within a target compartment (for example, within a cell), at the surface of a target compartment (for example, at the cell surface), in the vicinity of the target compartment (for example, when the effector structure is actively exported from the cell, leaks from the cell, or released upon cell death), or diffuse or be carried to a distant region of the sample to trigger a response. In some embodiments, effector structures can be targeted to their active sites by incorporation of targeting groups in the templated assembly product. Some non-limiting examples of targeting groups can include endoplasmic reticulum transport signals, golgi apparatus transport signals, nuclear transport signals, mitochondrial transport signals, ubiquitination motifs, other proteosome targeting motifs, or glycosylphosphatidylinositol anchor motifs. Targeting groups may be introduced by their incorporation into a templated assembly reactant moiety, chemical linker, or accessory group during synthesis, or may be generated during the ligation reaction.

In some embodiments, the effector structure can be presented on the surface of a target compartment. In another embodiment, the effector structure can be presented on the surface of a cell as a ligand bound to a major histocompatibility complex molecule.

In some embodiments, the effectors can be endogenous peptides, etc, and their analogue, or completely synthetic structures which are targets for effector structure-triggered agents such as antibodies. Availability of target nucleic acid can limit production of active effectors, therefore it may be desirable to have effector structures that exert activity when present at low levels.

The effector structures can also be produced by templating on accessible nucleic acid transcripts in a highly diverse set of samples, and combinations of effector structures can be produced on the same transcript, or on different transcripts that may be simultaneously present within a sample, such as a cell. Thus, a single effector structure can be assembled on different templates within the same sample, or several effector structures can be assembled on the same template, or several templates within the same sample, producing more copies of particular effector molecules, as well as a more diverse array of effector molecules on available templates within a sample.

Figure 5:
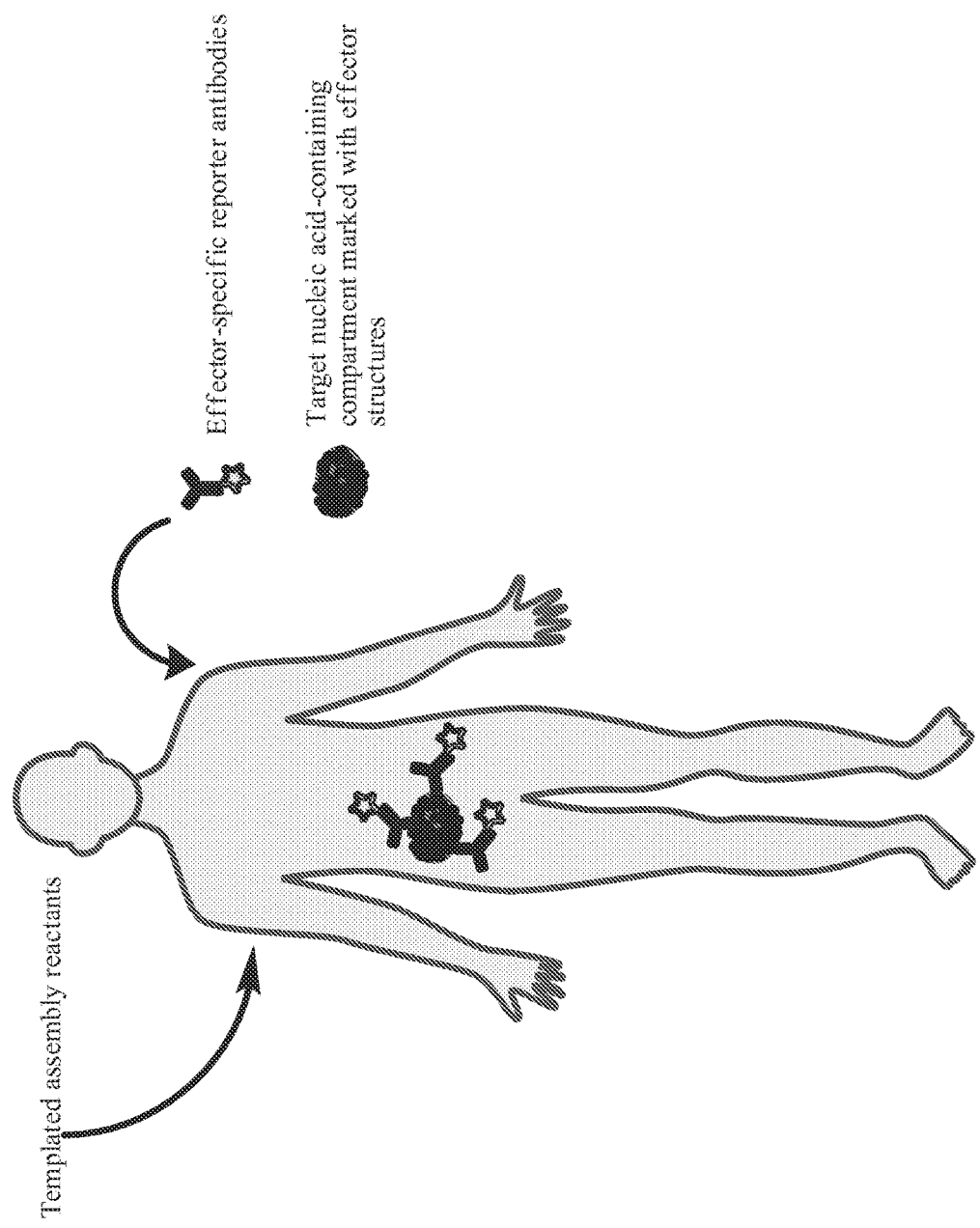
FIG. 5 is an illustration depicting localization of targets within the subject and specificity of the targeted templated assembly products to the localized targets.
Figure 6:
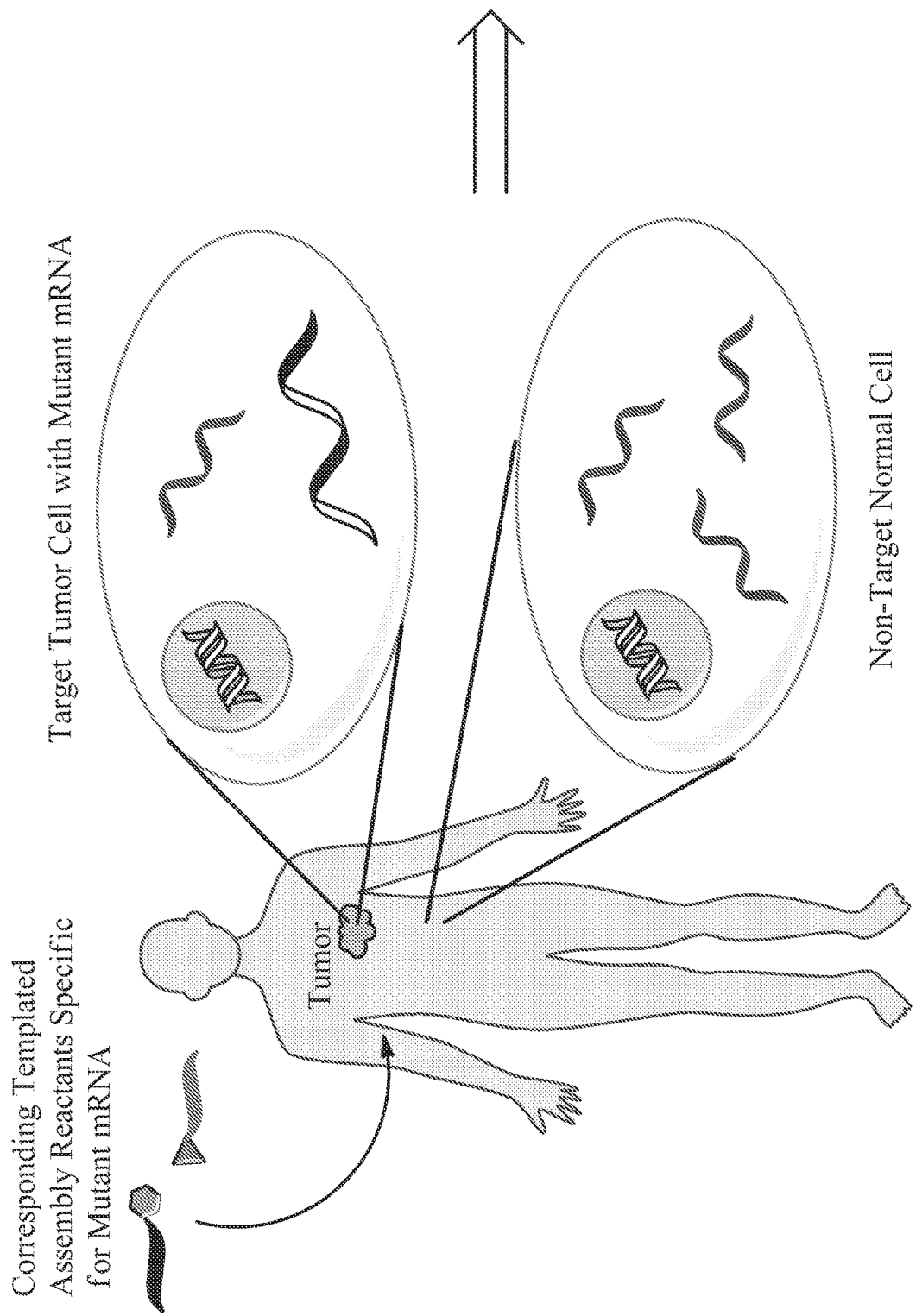
FIG. 6 is an illustration of an example of therapeutic use for selective elimination of tumor cells—before treatment.
Figure 7:
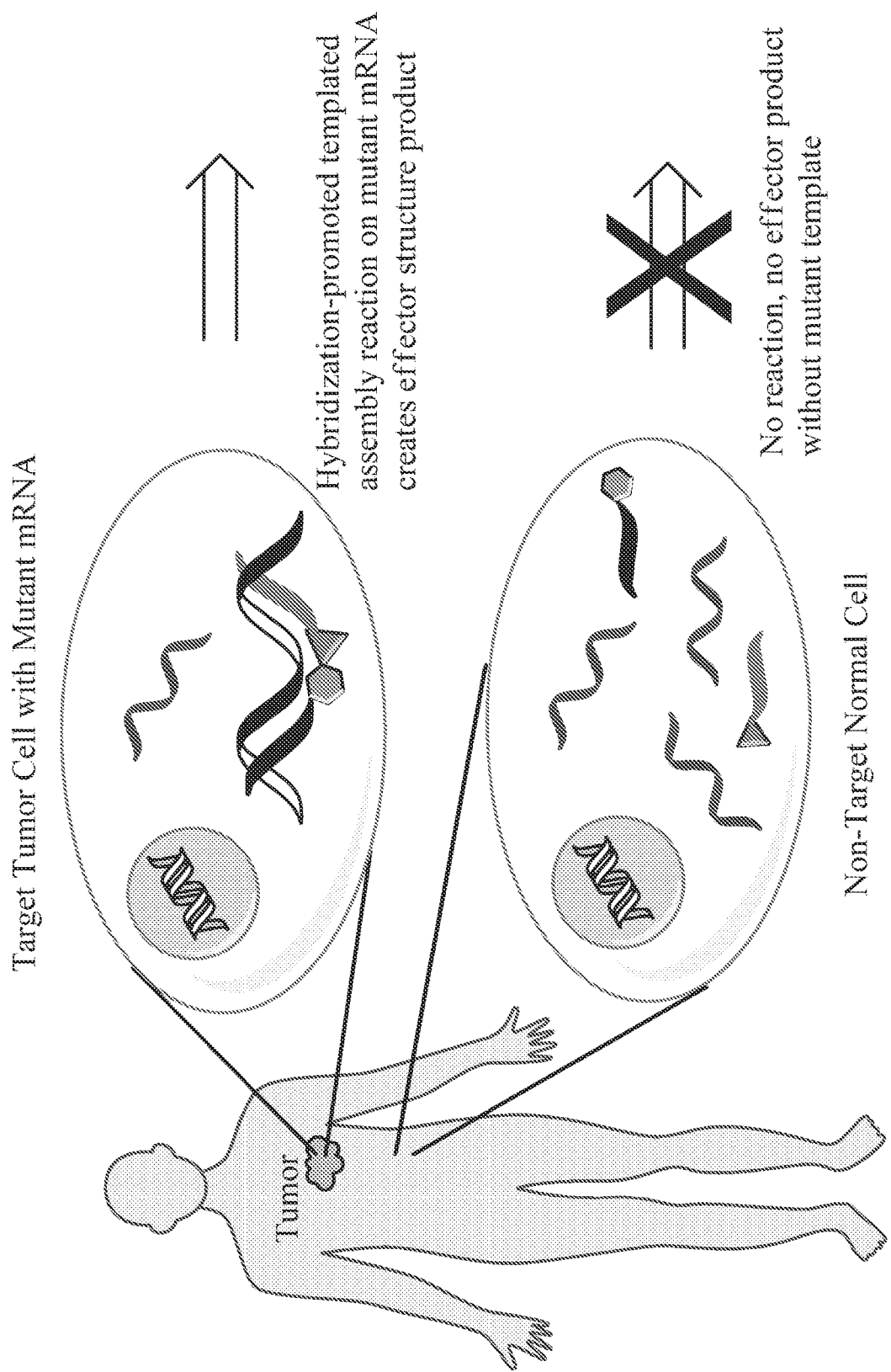
FIG. 7 is an illustration of an example of therapeutic use for selective elimination of tumor cells—hybridization during treatment.

Effector Structures as Chemical Markers for Localization of Target Nucleic Acids In some embodiments, effector structure-specific antibodies can be utilized in to indicate the location of target compartments within the sample, using antibody-detection methods. In these embodiments, corresponding templated assembly reactants as well as a reporter antibody can be administered. Effector structures are produced in target compartments, causing reporter antibody to bind and accumulate at target compartments. The location of the target compartments can then be determined by the reporter function of the antibody. FIG. 5 illustrates this general scheme of target compartment localization. Target compartments that may be localized include, but are not limited to, cancer cells, tumors, cells infected by a virus or other infectious agent, or any cell or group of cells expressing a specific nucleic acid sequence of interest that is not expressed in all cells of the sample. FIGS. 6 and 7 illustrate a general scheme of therapeutic use for selective elimination of tumor cells, before treatment (FIG. 6) and hybridization during treatment (FIG. 7).

Effector Structures Producing Desired Activity in Living Cells

Figure 8:
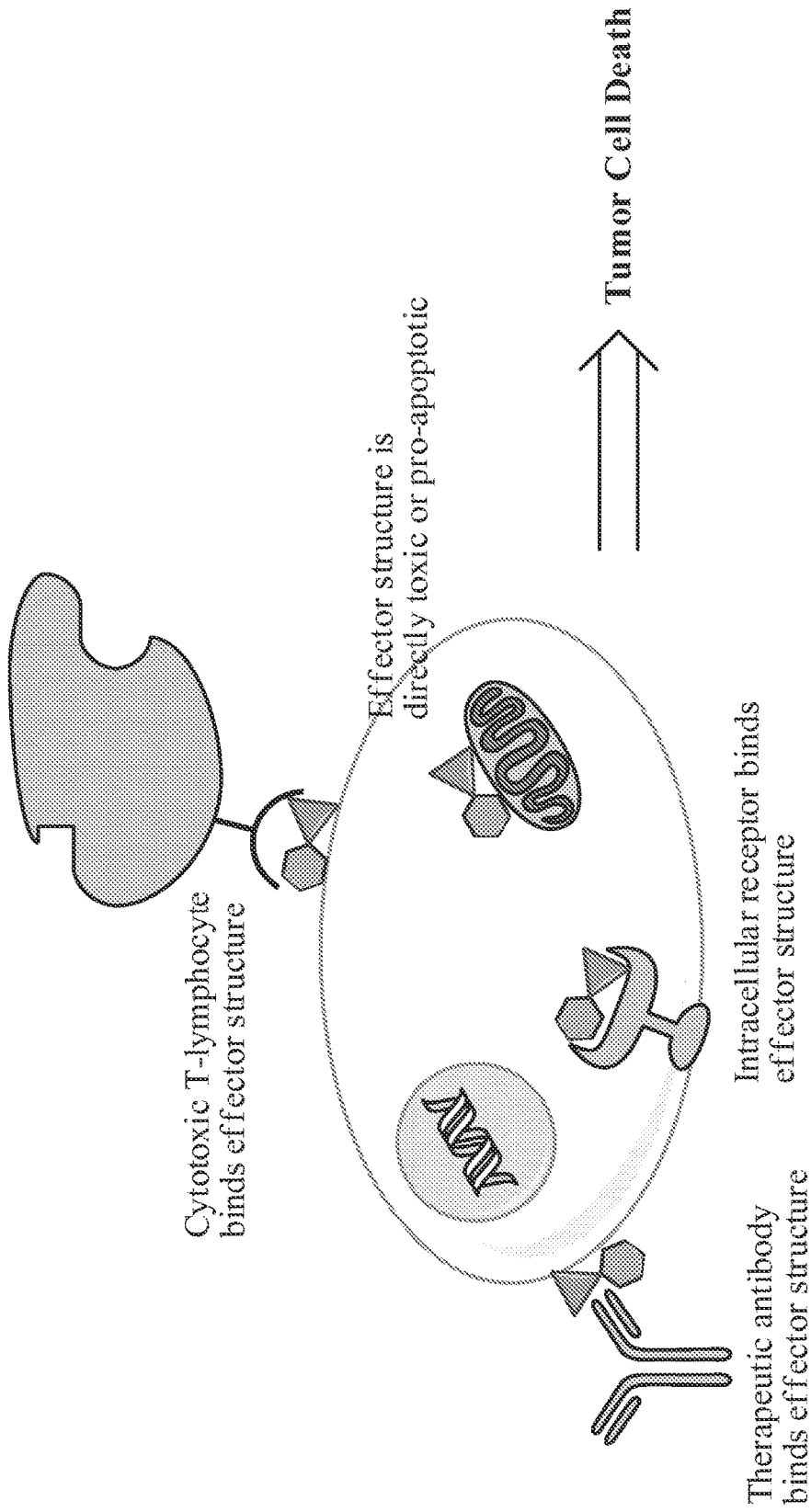
FIG. 8 is an illustration depicting effector structures produced in target cells and acting through different mechanisms to induce apoptosis: cytotoxic T-lymphocytes, therapeutic antibodies, intracellular receptors, direct cellular interaction.

Specific cellular populations can be modulated through the generation of effector structures, which ultimately result in the destruction or alteration of designated cellular target compartments. Effector structure-generated activity may be designed to delete undesired cellular target compartments. FIG. 8 illustrates the effector structures employing different mechanisms to induce apoptosis, such as cytotoxic T-lymphocytes, therapeutic antibodies, intracellular receptors, and direct cellular interaction.

Cytotoxic and Pro-Apoptotic Effector Structures

In some embodiments, killing or growth inhibition of target cells can be induced by direct interaction with cytotoxic, microbicidal, or virucidal effector structures. Numerous toxic molecules known in the art can be produced. In one embodiment, traceless bio-orthogonal reactive chemistry may produce toxic peptides. Some examples of toxic peptides can include, but are not limited to, bee melittin, conotoxins, cathelicidins, defensins, protegrins, and NK-lysin.

In some embodiments, killing or growth inhibition of target cells can be induced by pro-apoptotic effector structures. For example, effector peptides produced using traceless bio-orthogonal chemistry may include pro-apoptotic peptides, including but not limited to, prion protein fragment 106-126 (PrP 106-126), Bax-derived minimum poropeptides associated with the caspase cascade including Bax 106-134, and pro-apoptotic peptide (KLAKLAK)2.

Thrombogenic Effector Structures

In some embodiments, the effector molecule produced can be thrombogenic, in that it induces activation of various components of the clotting cascade of proteins, or activation of proteins, or activation and/or aggregation of platelets, or endothelial damage that can lead to a biologically active process in which a region containing pathogenic cells can be selectively thrombosed to limit the blood supply to a tumor or other pathogenic cell. These types of effectors can also induce clotting, or prevent clotting, or prevent platelet activation and aggregation in and around targeted pathogenic cells.

Immune Activating Effector Structures

In some embodiments, effector structures can mediate killing or growth inhibition of target cells or viruses by activating molecules, pathways, or cells associated with the immune system. Effector structures may engage the innate immune system, the adaptive immune system, and/or both.

Effector Structures Activating the Innate Immune System

In some embodiments, effector structures can mediate killing or growth inhibition of cells or viruses by stimulation of the innate immune system. In one embodiment, effector structures can include pathogen-associated molecular patterns (PAMPs), damage-associated molecular patterns (DAMPs), and synthetic analogues thereof.

In some embodiments, the innate immune system can be engaged by effector structures that activate the complement system. A non-limiting example of a complement activating effector structures can be the C3a fragment of complement protein C3.

In some embodiments, effector structures can be agonists of formylated peptide receptors. In one embodiment, the formylated tripeptide formyl-Met-Leu-Phe can be produced using traceless bio-orthogonal chemistry. A specific example scheme for generating fMLF peptides using traceless templated assembly reactants can include:

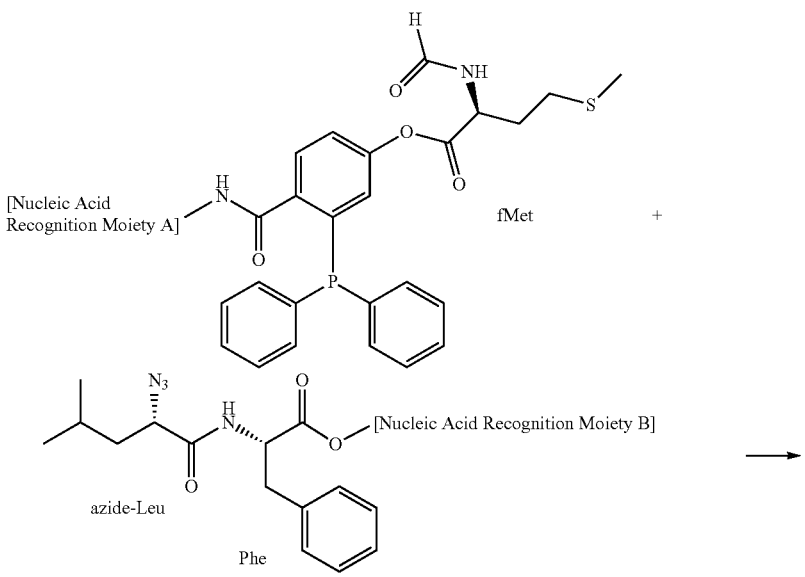

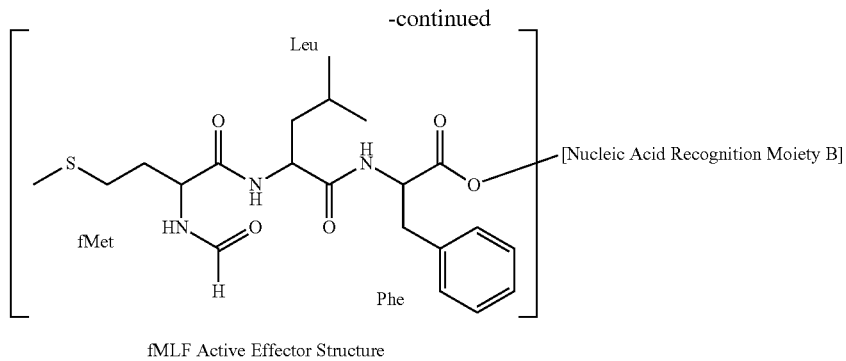

fMLF Active Effector Structure

In some embodiments, small peptide agonists of the formylated peptide receptor such as the peptide Trp-Lys-Tyr-Met-Val-(D-Met) can be produced.

In some embodiments, effector structures with natural or synthetic ligands of Toll-Like Receptors (TLR) can be produced. In a non-limiting example, an effector structure can include peptide fragments of heat shock proteins (hsp) known to be TLR agonists.

In some embodiments, traceless bio-orthogonal chemistry may be used to produce the muramyl dipeptide agonist of the NOD2 receptor to activate an inflammatory response.

Effector Structures Activating the Adaptive Immune System

In some embodiments, effector structures can mediate killing or growth inhibition of cells or viruses by activating molecules or cells of the adaptive immune system. Unique to the adaptive immune system, molecules or cells can be engineered to recognize an extraordinary variety of structures, thus removing the constraint that the effector structure must be intrinsically active or bind to an endogenous protein.

Because of the modularity of the system, a single engineered molecule or cell of the adaptive immune system can be utilized for therapy of any target compartments or target nucleic acids, since the same effector structure can be produced in the presence of any target nucleic acid. This is an advantage over the current state of the art, where new molecules or cells must be engineered to treat any new target, involving significant time, difficulty, and cost.

In some embodiments, an effector structure can be a ligand for an antibody or antibody fragment (including but not limited to Fab, Fv, and scFv). Traceless bio-orthogonal approaches can be used to produce a peptide or other epitope that is bound by an existing antibody, or an antibody can be developed to recognize an effector structure created by any selectively reactive or bio-orthogonal approach.

For therapeutic intervention in conjunction with templated assembly reactants, manufactured antibodies can be administered as effector structure-triggered agents. The term "effector structure-triggered agent" as used herein refers to an exogenously-produced compound or cell capable of initiating a desired activity upon binding to an effector structure. The agent may be administered to a sample before, during, or after administration of templated assembly reactants. An example can include, but is not limited to, reporter antibodies. In one embodiment, unmodified antibodies can be utilized to mediate therapeutic effects. In another embodiment, effector structure specific antibody can be manufactured with a payload attached designed to enhance the therapeutic effect. Some non-limiting examples of therapeutic antibody payloads can include cytotoxins, radioisotopes, radiosensitizers used in conjunction with radiation therapy, enzymes for the conversion of a co-administered prodrug to an active drug, or any other antibody-directed therapy.

In some embodiments, an antibody may be used for detection of an effector structure in vivo, thus localizing a target compartment within a subject.

In some embodiments, effector structures can activate T-cells. Activation of T-cells can be achieved by an effector structure binding to a T-cell receptor (TCR). In one embodiment, an effector structure can be presented on the surface of a target cell bound to a major histocompatibility complex molecule (MHC), facilitating binding of a T-cell receptor. An effector structure may be bound by MHC class I or MHC class II molecules. In an exemplary embodiment, an effector structure is bound by MHC class I molecules. The structure that binds to the TCR can be a conventional peptide antigen, or a "superantigen" that binds to a broad subset of T cells that express a particular variable (V) region. As opposed to a TCR that is selected to interact with specific antigen, a superantigen can activate a large number of T cell populations that have receptors capable of binding to different antigen-MHC complexes, and induce a strong inflammatory response to set off a cascade of inflammatory mediators. Thus a superantigen or superantigen mimetic can be produced as an active effector structure that can recruit large numbers of T cells to a pathogenic cell, and lead to destruction or limitation in the growth of such cells.

Natural ligands bound to MHC class I molecules are typically peptides of 8 to 10 amino acids in length, though other lengths are permissible. Natural ligands bound to MHC class II molecules are typically peptides of 15 to 24 amino acids in length, though other lengths are permissible. Effector structures can be produced using traceless bio-orthogonal chemistry. A peptide that is a known MHC ligand can be utilized as an effector structure, or a novel peptide can be produced. Assays for evaluating binding of peptides to MHC molecules are known in the art, and may be used to evaluate candidate effector structures for MHC binding MHC molecules are also known to bind non-peptide structures and peptidomimetics. Non-traceless bio-orthogonal templated assembly approaches may be utilized to create peptidomimetic MHC-binding antigens for activation of T-cell receptors. In one embodiment, the peptidomimetic can be a peptide of 6 to 40 amino acids or non-standard amino acids, where between 1 to 4 residues are replaced by a non-traceless bio-orthogonal ligation structure, such as:

where R1 and R2 are covalently bonded standard or non-standard amino acids, m=0 to 40, n=0 to 40, and m+n=2 to 39. In some embodiments, m+n=3 to 11, producing structures suitable for binding to MHC class I.

Some examples of effector structures using the MART-1 immunodominant tumor associated antigen as a design scaffold can include:

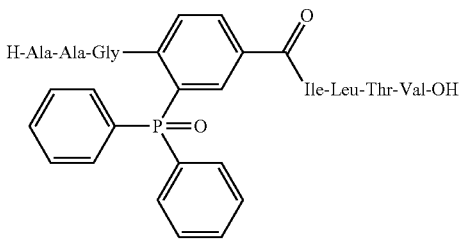

Example peptidomimetic effector structure based on Staudinger ligation chemistry.

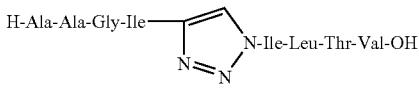

Example of peptidomimetic effector structure based on azide-alkyne ligation chemistry.

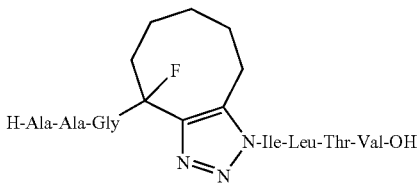

Example of peptidomimetic effector structure based on azide-cyclooctyl alkyne ligation chemistry.

Peptidomimetic effector structures may be designed based on a natural ligand known to bind MHC and activate a T-cell receptor (as in the examples above.) Alternatively, the peptidomimetic effector structure may be an entirely new structure, and a new T-cell clone or antibody-TCR chimera (T-body) may be developed for use as an effector structure-triggered agent. This approach offers the benefit of using highly non-self, non-cross-reactive effector structures which may increase activity while reducing undesired side-effects during therapy.

In some embodiments, natural peptide or peptidomimetic MHC-binding effector structures can be utilized in conjunction with adoptive T-cell therapy, where the adoptive T-cell serves as an effector structure-triggered agent. An adoptive T cell therapy provides a patient with exogenous T cells which can accomplish a therapeutically desirable immuno-reaction. However, allogenic T cells can be potentially problematic either from host rejection, or the risk of graft-vs.-host disease.

Recently developed techniques have enabled the use of autologous T cells for various therapeutic applications, where host genetic incompatibility is avoided. Clinically relevant T cell subsets (including clonally-derived cells with specific TCRs) can be expanded in vitro and returned to autologous patients. Greater selectivity can be achieved by means of autologous T cells transfected in vitro with vectors enabling the expression of TCRs of known specificity against target antigens (such as those known to be expressed on tumors), or engineered chimeric antigen receptors with equivalent desired specificities.

Once an active effector structure has been selected, appropriate selectively-reactive moieties and effector partial moieties can be designed for incorporation into the templated assembly reactant(s). These moieties are designed such that they can reconstitute the active effector moiety when a templated assembly reaction occurs.

Determine Nucleic Acid Templating Strategy

When a suitable nucleic acid target sequence is identified and an active effector product is determined, a strategy for designing a set of corresponding templated assembly reactants can be produced. A set of corresponding templated assembly reactants is selected such that:

a) they will bind the target nucleic acid template at suitable proximate spatial positions as determined by the hybridization sites of their nucleic acid recognition moieties and, b) the selectively reactive moieties of the templated assembly reactants can react with each other in a manner that facilitates formation of the active effector product from the effector partial moieties.

The following sections describe the design and synthesis of each individual moiety, and processes for synthesizing entire templated assembly reactants. Optional chemical linkers or accessory groups that may be incorporated into templated assembly reactants are also described.

Nucleic Acid Recognition Moiety Design and Synthesis

A nucleic acid templated assembly reactant includes at least one nucleic acid recognition moiety. The nucleic acid recognition moiety is the targeting component of the composition that recognizes specific target sequences and interacts in a sequence-specific manner with the target nucleic acids via Watson-Crick or Hoogsteen base-pairing interactions. The nucleic acid recognition moiety can bind to the target nucleic acids or may facilitate binding to the target nucleic acids. In one embodiment, the nucleic acid recognition moiety binds directly to the target nucleic acids.

The phrase "nucleic acid recognition moiety" as used herein refers to a compound that facilitates sequence-specific binding to a target nucleic acid. The main function of the nucleic acid recognition moiety is to use the target molecule as a site for templated assembly. This differs from many current technologies, as their hybridization is often optimized to block or inhibit the target molecule directly.

In some embodiments, the nucleic acid recognition moiety binds to a target nucleic acid. The binding can be through direct hybridization of the nucleic acid recognition moiety with the target nucleic acid or indirectly through an intermediate, such as a linker, that binds both the nucleic acid recognition moiety and the target nucleic acid. The phrases "target nucleic acid sequence" and "target nucleic acid" are used interchangeably and refer to a sequence of units or nucleic acids which are intended to act as a template for nucleic acid templated assembly.

The nucleic acid recognition moiety may include oligomers of base-pair forming units, such as nucleic acids or nucleic acid analogues. The oligomer may be made of multiple units where some or all of the units are bases capable of forming Watson-Crick or Hoogsteen base-pairing interactions, allowing sequence-specific binding to target nucleic acids in a duplex or multiplex structure.

The oligomer sequence may be DNA nucleotides, RNA nucleotides, phosphorothioate-modified nucleotides, 2-O-alkylated RNA nucleotides, halogenated nucleotides, locked nucleic acid nucleotides (LNA), peptide nucleic acids (PNA), morpholino nucleic acid analogues (morpholinos), pseudouridine nucleotides, xanthine nucleotides, hypoxanthine nucleotides, 2-deoxyinosine nucleotides, other nucleic acid analogues capable of base-pair formation, or combinations thereof. In one embodiment, the nucleic acid recognition moiety includes nucleic acids and hybridizes to mRNA targets.

The oligomers may also incorporate, interact with or be bound to specialized units. For example, when using the nucleic acid recognition moieties in the presence of nucleases that may degrade standard DNA or RNA, such as in live cells or lysates, it may be desirable to incorporate nuclease-resistant bases into the oligomer. Some non-limiting examples can include phosphorothioate bases, 2-O-alkylated or 2-halogenated RNA bases, locked nucleic acids, peptide nucleic acids, morpholinos or a chimera including at least one of these. Unlike antisense probes that depend on RNase H activity, internal bases of the oligomer need not induce RNase H hydrolysis of a target RNA transcript. Thus, there is no requirement for RNase H-inducing bases at any position in the nucleic acid recognition moiety.

The sequence of bases in a nucleic acid recognition moiety can be complementary to a hybridization site on a target nucleic acid, allowing sequence-specific binding of the nucleic acid recognition moiety to the target nucleic acid. In one embodiment, the hybridization site is selected such that its sequence is not similar to sequences known to be present in non-target nucleic acids. In another embodiment, the hybridization site includes one or more mutations found within the target nucleic acid, allowing specific binding of nucleic acid recognition moiety to the target nucleic acid but not to non-target nucleic acids that do not contain the mutation. In yet another embodiment, the nucleic acid recognition moiety may be designed as a stem-loop structure, with possible improvement in the desired binding interaction with target nucleic acids.

The binding site on the target nucleic acid can be anywhere from about 5 to about 100 bases in length. In one embodiment, the binding site on the target nucleic acid can be in the range of about 5 to about 50 bases in length. In another embodiment, the binding site on the target nucleic acid can be in the range of about 5 to about 40 bases in length. In yet another embodiment, the binding site on the target nucleic acid can be in the range of about 10 to about 30 bases in length.

Likewise, the nucleic acid recognition moiety can include an oligomer that can bind to the target nucleic acid. The oligomer can be anywhere from about 5 to about 100 bases in length. In one embodiment, the oligomer can be in the range of about 5 to about 50 bases in length. In another embodiment, the oligomer can be in the range of about 5 to about 40 bases in length. In yet another embodiment, the oligomer can be in the range of about 10 to about 30 bases in length.

The nucleic acid recognition moiety can also be optimized to provide a desired interaction with the target nucleic acid sequence. The length of the target nucleic acid that the nucleic acid recognition moiety binds can be selected based on chemical properties of the complementary sequence of the target nucleic acid. Such properties can include melting and annealing temperatures of the complementary sequence. The melting temperature, $T_m$, is defined as the temperature in degrees Celsius, at which 50% of all molecules of a given nucleic acid sequence are hybridized into a double strand, and 50% are present as single strands. The annealing temperature is generally 5° C. lower than the melting temperature.

The $T_m$ of the complementary sequence of the target nucleic acid can be in a range between about 10° C. below to about 40° C. above the temperature of the conditions in which the templated assembly reactant will be used. For example, if templated assembly reactants are to be used at 37° C., the nucleic acid recognition moiety may be designed with an expected $T_m$ between 27° C. to 77° C. In one embodiment, the template assembly reactants can be used at approximately 37° C., and the $T_m$ of the complementary sequence used in the nucleic acid recognition moiety is designed to be in the range of about 37° C. to about 52° C.

In some embodiments, nucleic acid recognition moiety can be designed such that the $T_m$ to bind the target nucleic acid is substantially different from the $T_m$ to bind a similar non-target nucleic acid. For example, the nucleic acid recognition moiety may be designed such that the hybridization site it binds to on a target nucleic acid includes the site of a mutation. In an exemplary embodiment, the $T_m$ of the nucleic acid recognition moiety binding to the target nucleic acid is at or above the temperature at which the templated assembly reactant will be used, while the $T_m$ of the nucleic acid recognition moiety binding to the non-target nucleic acid is below the temperature at which the templated assembly reactant will be used. The nucleic acid recognition moiety will then bind to mutant target sequence, but not to the non-target, non-mutant sequence.

Binding or hybridization sites of the nucleic acid recognition moieties of members of a set of corresponding templated assembly reactants can be on the same target nucleic acid. In one embodiment, the binding or hybridization sites can be found on the same target nucleic acid but separated by about 0 to about 100 bases on the target nucleic acid. In another embodiment, the binding or hybridization sites can be separated by about 0 to about 30 bases on the target nucleic acid. In another embodiment, the binding or hybridization sites can be separated by distances greater than 30 bases on the same target nucleic acid, but be brought into closer proximity through secondary or tertiary structure formation of the target nucleic acid. In one embodiment, the binding or hybridization sites can be separated by a distance greater than 100 bases and brought into closer proximity through secondary or tertiary structure formation of the target nucleic acid.

Oligomers may be synthesized by several methods known in the art. Nucleotide-based oligomers may be synthesized in solution or on a solid-phase using phosphoramidite chemistry. Peptide nucleic acids may also be synthesized in solution or on a solid phase using methods known in the art. Various methods of morpholino synthesis could also be used. Any of the aforementioned types of oligomer may also be obtained fully synthesized from various commercial sources.

Commercially available derivatized bases may be incorporated to introduce functional groups including but not limited to amines, hydrazides, thiols, carboxylic acids, isocyanates, aldehydes which may then be conjugated with active functional groups on other moieties using standard techniques of bioconjugation chemistry to facilitate synthesis of the complete templated assembly reactant.

Selectively-Reactive Moiety Design and Synthesis

A nucleic acid template assembly reactant composition also includes at least one selectively-reactive moiety. The selectively-reactive moiety enables the formation of nucleic acid recognition product, such as through a chemical reaction or physical interaction with a corresponding selectively-reactive moiety. The selectively-reactive moiety can interact with or bind to the nucleic acid recognition moiety. The selectively-reactive moiety can also interact with or bind to the effector partial moiety. The terms "bind," "binds," "binding," and "bound," as used herein, refer to a stable interaction between two molecules that are close to one another. The terms include physical interactions, such as chemical bonds (either directly linked or through intermediate structures), as well as non-physical interactions and attractive forces, such as electrostatic attraction, hydrogen bonding, and van der Waals/dispersion forces.

A selectively-reactive moiety can be biologically inert, in particular, the selectively-reactive moiety can interact readily with a corresponding selectively-reactive moiety, but will not readily interact with natural biomolecules. This is to ensure that the nucleic acid templated assembly product is formed when corresponding templated assembly reactants are assembled on a target nucleic acid. It also safeguards the nucleic acid templated assembly reactant from reacting with functional groups on other molecules present in the environment in which the assembly occurs, preventing the formation of intended product. An example of a selectively-reactive moiety includes a bio-orthogonal reactive moiety. A bio-orthogonal reactive moiety reacts chemically with a corresponding bio-orthogonal reactive moiety and does not readily react chemically with other biomolecules.

The selectively-reactive moiety provides a mechanism for templated reactions to occur in complex target compartments, such as a cell, virus, tissue, tumor, lysate, other biological structure, or spatial region within a sample that contains the target nucleic acid, or that contains a different amount of target nucleic acid than a non-target compartment. A selectively-reactive moiety can react with a corresponding selectively-reactive moiety, but does not react with common biochemical molecules under typical conditions. Unlike other reactive entities, the selectivity of selectively-reactive moiety prevents ablation of the reactive group prior to assembly of the product or reactant.

An example of selectively-reactive moiety can include a bio-orthogonal reactive moiety. The bio-orthogonal reactive moiety includes those groups that can undergo "click" reactions between azides and alkynes, traceless or non-traceless Staudinger reactions between azides and phosphines, and native chemical ligation reactions between thioesters and thiols. Additionally, the bio-orthogonal moiety can be any of an azide, a cyclooctyne, a nitrone, a norbornene, an oxanorbornadiene, a phosphine, a dialkyl phosphine, a trialkyl phosphine, a phosphinothiol, a phosphinophenol, a cyclooctene, a nitrile oxide, a thioester, a tetrazine, an isonitrile, a tetrazole, a quadricyclane, and derivatives thereof. Selectively reactive moieties of members of a set of corresponding templated assembly reactants are selected such that they will react with each other to produce an active effector structure.

Multiple selectively-reactive moieties can be used with the methods and compositions disclosed herein, some non-limiting examples include:

Azide-Alkyne "Click Chemistry"

Click chemistry is highly selective as neither azides nor alkynes react with common biomolecules under typical conditions. Azides of the form R—N$_3$ and terminal alkynes of the form R—C≡CH or internal alkynes of the form R—C≡C—R react readily with each other to produce Huisgen cycloaddition products in the form of 1,2,3-triazoles.

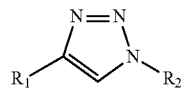

Azide-based templated assembly reactants have the substructure: R—N$_3$ where R is a chemical linker, nucleic acid recognition moiety, or effector partial moiety. Azides and azide derivatives may be readily prepared from commercially available reagents.

Azides can also be introduced to a effector partial moiety during synthesis of the effector partial moiety. In one embodiment, an azide group is introduced into a effector partial moiety comprised of a peptide by incorporation of a commercially available azide-derivatized standard amino acid or amino acid analogue during synthesis of the effector partial moiety peptide using standard peptide synthesis methods Amino acids may be derivatized with an azide replacing the α-amino group, affording a structure of the form:

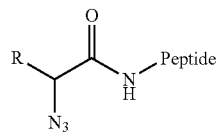

where R is a side chain of a standard amino acid or non-standard amino acid analogue.

Commercially available products can introduce azide functionality as an amino acid side chains, resulting in a structure of the form:

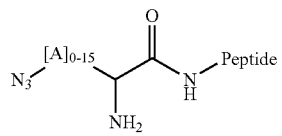

where A is any atom and its substituents in a side chain of a standard amino acid or non-standard amino acid analogue.

An azide may also be introduced into a effector partial moiety peptide after synthesis by conversion of an amine group on the peptide to an azide by diazotransfer methods. Bioconjugate chemistry can also be used to join commercially available derivatized azides to chemical linkers, nucleic acid recognition moieties, or effector partial moieties that contain suitable reactive groups.

Standard alkynes can be incorporated into a templated assembly reactant by methods similar to azide incorporation. Alkyne-functionalized nucleotide analogues are commercially available, allowing alkyne groups to be directly incorporated at the time of nucleic acid recognition moiety synthesis. Similarly, alkyne-derivatized amino acid analogues may be incorporated into a effector partial moiety by standard peptide synthesis methods. Additionally, diverse functionalized alkynes compatible with bioconjugate chemistry approaches may be used to facilitate the incorporation of alkynes to other moieties through suitable functional or side groups.

Azide-Activated Alkyne "Click Chemistry"

Standard azide-alkyne chemistry reactions typically require a catalyst, such as copper(I). Since copper(I) at catalytic concentrations is toxic to many biological systems, standard azide-alkyne chemistry reactions have limited uses in living cells. Copper-free click chemistry systems based on activated alkynes circumvent toxic catalysts.

Activated alkynes often take the form of cyclooctynes, where incorporation into the cyclooctyl group introduces ring strain to the alkyne.

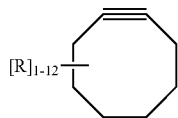

Heteroatoms or substituents may be introduced at various locations in the cyclooctyl ring, which may alter the reactivity of the alkyne or afford other alternative chemical properties in the compound. Various locations on the ring may also serve as attachment points for linking the cyclooctyne to a nucleic acid templated assembly moiety or linker. These locations on the ring or its substituents may optionally be further derivatized with accessory groups.

Multiple cyclooctynes are commercially available, including several derivatized versions suitable for use with standard bioconjugation chemistry protocols. Commercially available cyclooctyne derivatized nucleotides can aid in facilitating convenient incorporation of the selectively-reactive moiety during nucleic acid recognition moiety synthesis.

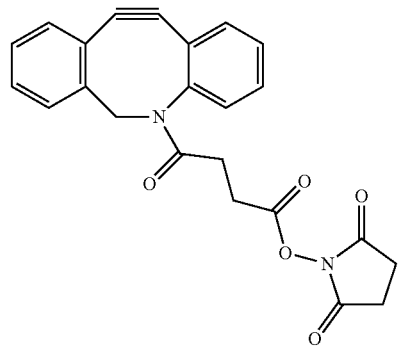 [SMILES: O=C(CCC(=O)N1Cc2ccccc2C#Cc2ccccc21)ON1C(=O)CCC1=O]

Cyclooctyne-azide based bio-orthogonal chemistry may produce templated assembly products of the general structure:

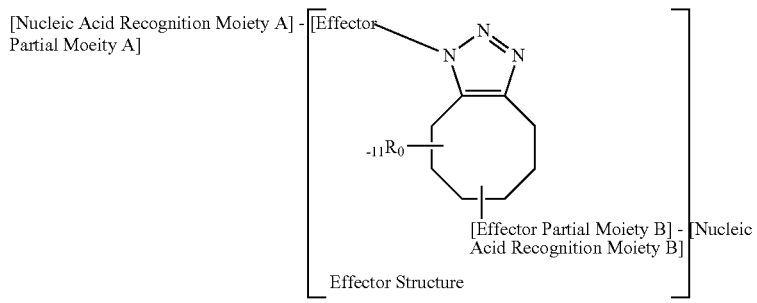

Another Example:

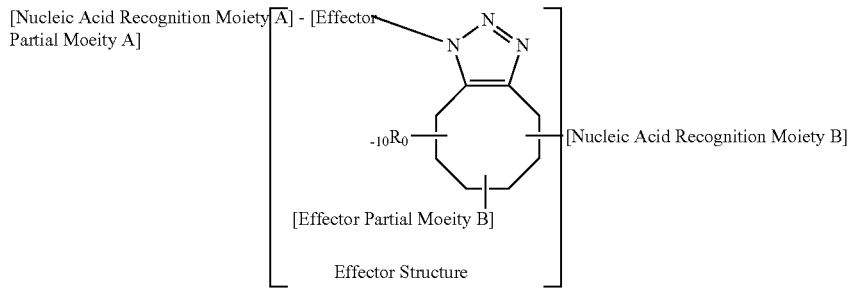

Azide-Phosphine Staudinger Chemistry

The Staudinger reduction, based on the rapid reaction between an azide and a phosphine or phosphite with loss of $N_2$, also represents a bio-orthogonal reaction. The Staudinger ligation, in which covalent links are formed between the reactants in a Staudinger reaction, is suited for use in nucleic acid templated assembly. Both non-traceless and traceless forms of the Staudinger ligation allow for a diversity of options in the chemical structure of products formed in these reactions.

Non-Traceless Staudinger Ligation

The standard Staudinger ligation is a non-traceless reaction between an azide and a phenyl-substituted phosphine such as triphenylphosphine, where an electrophilic trap substituent on the phosphine, such as a methyl ester, rearranges with the aza-ylide intermediate of the reaction to produce a ligation product linked by a phosphine oxide. An example of a Staudinger ligation product formed by templated assembly reactants A and B may have the structure:

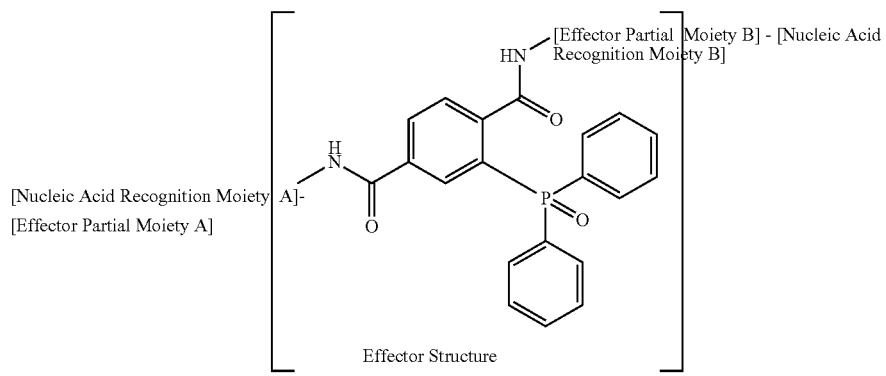

Effector Structure

Phenyl-substituted phosphines carrying electrophilic traps can also be readily synthesized. Derivatized versions are available commercially and suitable for incorporation into templated assembly reactants:

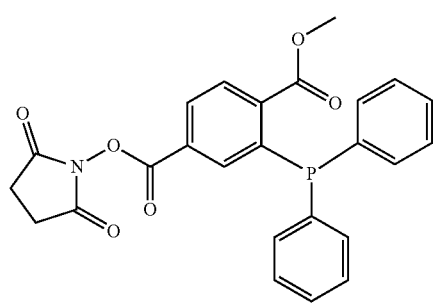 [SMILES: COC(=O)c1ccc(C(=O)ON2C(=O)CCC2=O)cc1P(c1ccccc1)c1ccccc1]

Traceless Staudinger Ligation

In some embodiments, phosphines capable of traceless Staudinger ligations may be utilized as selectively-reactive moieties. In a traceless reaction, the phosphine serves as a leaving group during rearrangement of the aza-ylide intermediate, creating a ligation typically in the form of a native amide bond. Compounds capable of traceless Staudinger ligation generally take the form of a thioester derivatized phosphine or an ester derivatized phosphine:

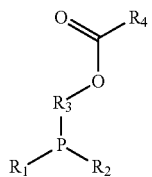

Ester derivatized phosphines for traceless Staudinger ligation.

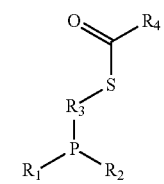

Thioester derivatized phosphines for traceless Staudinger ligations.

Chemical linkers or accessory groups may optionally be appended as substituents to the R groups in the above structures, providing attachment points for nucleic acid recognition moieties or for the introduction of additional functionality to the reactant.

Traceless Phosphinophenol Staudinger Ligation

Compared to the non-traceless Staudinger phenylphosphine compounds, the orientation of the electrophilic trap ester on a traceless phosphinophenol is reversed relative to the phenyl group. This enables traceless Staudinger ligations to occur in reactions with azides, generating a native amide bond in the product without inclusion of the phosphine oxide.

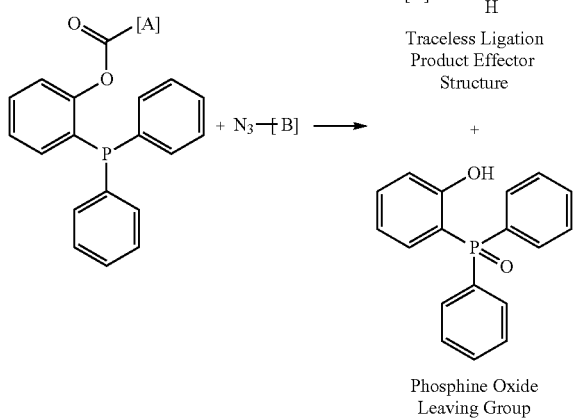

Traceless Ligation Product Effector Structure

Phosphine Oxide Leaving Group

The traceless Staudinger ligation may be performed in aqueous media without organic co-solvents if suitable hydrophilic groups, such as tertiary amines, are appended to the phenylphosphine. An article by Weisbord and Marx (2010) describes preparation of water-soluble phosphinophenol, which may be loaded with a desired effector partial moiety containing a carboxylic acid (such as the C-terminus of a peptide) via the mild Steglich esterification using a carbodiimide such as dicyclohexylcarbodiimide (DCC) or N,N'-diisopropylcarbodiimide (DIC) and an ester-activating agent such as 1-hydroxybenzotriazole (HOBT). This approach facilitates synthesis of templated assembly reactants of the form:

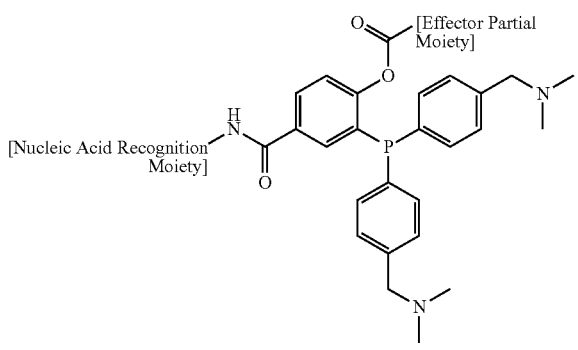

Water-soluble phosphinophenol-based traceless templated assembly reactant structure.

Traceless Phosphinomethanethiol Staudinger Ligation

Phosphinomethanethiols represent an alternative to phosphinophenols for mediating traceless Staudinger ligation reactions. In general, phosphinomethanethiols possess favorable reaction kinetics compared with phosphinophenols in mediating traceless Staudinger reaction. U.S. patent application 2010/0048866 and an article to Tam et al. (2007) describe preparation of water-soluble phosphinomethanethiols of the form:

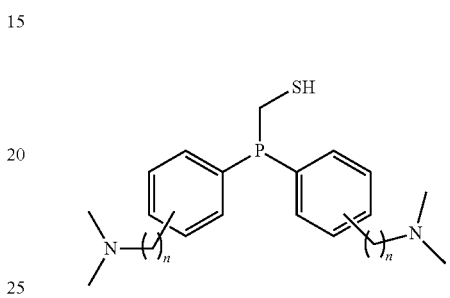

These compounds may be loaded with a peptide or other payload, in the form of an activated ester, to form a thioester suitable for use as a traceless bio-orthogonal reactive group:

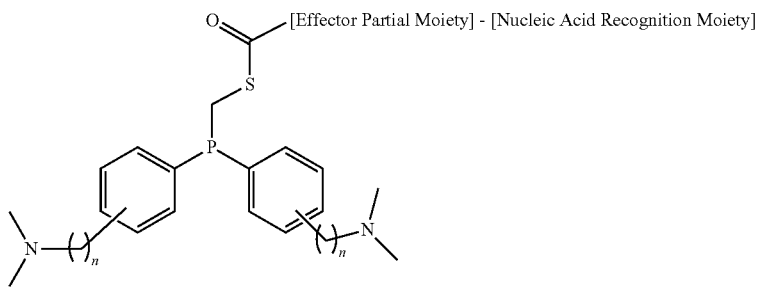

Templated assembly reactant structure based on water-soluble phosphinomethanethiol traceless Staudinger bio-orthogonal chemistry.

Native Chemical Ligation

Native chemical ligation is a bio-orthogonal approach based on the reaction between a thioester and a compound bearing a thiol and an amine. The classic native chemical ligation is between a peptide bearing a C-terminal thioester and another bearing an N-terminal cysteine, as seen below:

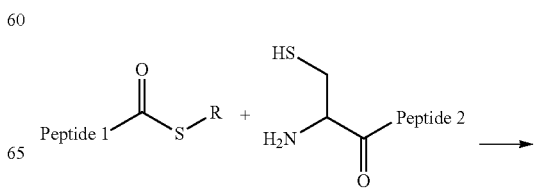

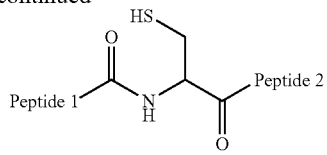

Native chemical ligation may be utilized to mediate traceless reactions producing a peptide or peptidomimetic containing an internal cysteine residue, or other thiol-containing residue if non-standard amino acids are utilized.

N-terminal cysteines may be incorporated by standard amino acid synthesis methods. Terminal thioesters may be generated by several methods known in the art, including condensation of activated esters with thiols using agents such as dicyclohexylcarbodiimide (DCC), or introduction during peptide synthesis via the use of "Safety-Catch" support resins.

Other Selectively Reactive Moieties

Any suitable bio-orthogonal reaction chemistry may be utilized for synthesis of templated assembly reactants, as long as it efficiently mediates a reaction in a highly selective manner in complex biologic environments. A recently developed non-limiting example of an alternative bio-orthogonal chemistry that may be suitable is reaction between tetrazine and various alkenes such as norbornene and trans-cyclooctene, which efficiently mediates bio-orthogonal reactions in aqueous media.

Chemical linkers or accessory groups may optionally be appended as substituents to the above structures, providing attachment points for nucleic acid recognition moieties or effector partial moieties, or for the introduction of additional functionality to the reactant.

Effector Partial Moiety Design and Synthesis

A nucleic acid templated assembly reactant further includes at least one effector partial moiety. The effector partial moiety is a portion of an active effector structure, such that when a set of corresponding templated assembly reactants take part in a templated reaction, their effector partial moieties combine to produce the desired active effector structure in the templated assembly ligation product. Thus, the effector partial moiety contributes to the chemical structure of the active effector structure. The effector partial moiety can be a distinct portion of the templated assembly reactant, or may include part or all of the nucleic acid recognition moiety and/or part or all of the selectively-reactive moiety. The terms "active effector structure" and "effector structure" are used interchangeably herein and refer to the active portion of a templated assembly product that triggers a desired effect.

The effector partial moiety does not possess the targeted activity or the same level of activity associated with the active effector structure. In some instances, the effector partial structure is substantially inactive as compared to the active effector structure. In one embodiment, the individual effector partial moieties can possess separate activity, but binding the effector partials moieties together creates an activity not possessed by them individually. For example, a bivalent effector structure that binds two different antibodies (each binds to a effector partial structure), making the effector suitable e.g., for detection in a sandwich ELISA as described in the Example 1 regarding the nucleic acid templated assembly diagnostic evaluation assay.

In some embodiments, a single effector partial moiety may be present as part the templated assembly reactant. However, a single effector partial moiety alone does not produce an active effector structure. An effector partial moiety may be positioned between the nucleic acid recognition moiety and the selectively-reactive moiety, or attached to the selectively-reactive moiety so that the selectively-reactive moiety is between the effector partial moiety and the nucleic acid recognition moiety, or both.

In some embodiments, more than one effector partial moieties may be present as part of a single templated assembly reactant. Assembly of the nucleic acid-templated assembly reactant allows one effector partial moiety to bind to a separate effector partial moiety, that results in the production of the active effector structure. More than one effector partial moiety may be attached to the selectively-reactive moiety so that the selectively-reactive moiety is between the effector partial moieties and the nucleic acid recognition moiety. In one embodiment, the effector partial moiety includes a chemical linker capable of binding the selectively-reactive moiety.

In some embodiments, multiple templated assembly reactants may be present to produce the active effector structure. More than one nucleic acid-templated assembly reactant are assembled and positioned within close proximity of one another, see FIG. 9 and FIG. 1B. The selectively-reactive moieties on the adjacent templated assembly reactants bind, through a chemical reaction such as a bio-orthogonal reaction, and the effector partial moieties are positioned to allow the production of the active effector structure.

Both efficiency of nucleic acid templated assembly reactions and efficiency of delivery of reactants to target compartments in a sample generally decrease with increasing size of the reactants. In some embodiments, one or more effector partial moieties are selected such that they are minimal in size while still producing an active effector structure. In one embodiment, the molecular size of a effector partial moiety is less than about 20 kDa. In another embodiment, the molecular size of a effector partial moiety is less than about 10 kDa.

The effector partial moiety can also be conjugated to other moieties on a templated assembly reactant such that the effector structure produced may be cleaved from the templated assembly ligation product after the reaction has occurred. Cleavage may occur via hydrolysis of a bond, or be catalyzed by enzymes or other molecules within a cell. Non-limiting examples of cleavage linkages include: esters, thioesters, imines, hydrazones, cleavage motifs of cellular proteases, or substrates of cellular enzymes.

In embodiments in which a traceless bio-orthogonal reactive group forms a native amide bond in the effector structure, the effector partial moiety may include a non-active portion of an active peptide, or a non-active portion of a non-peptide drug or endogenous bioactive compound that can be reconstituted via an amide bond to a corresponding portion.

In embodiments in which a non-traceless bio-orthogonal reactive group incorporates a phosphine oxide, triazole, or other bio-orthogonal ligation residue, effector partial moieties may include a non-active portion of a peptidomimetic structure or non-active portion of a drug or other bioactive compound. In these embodiments, the ligated residue from the bio-orthogonal reaction can be integrated into the effector structure.

Due to the diverse nature of effector partial moieties, various methods may be necessary for synthesis. In one embodiment, peptides are used, and effector partial moieties may be synthesized using standard Merrifield solid-phase synthesis. Synthesis approaches for other effector partial moieties are dictated by the specific chemical structure of the particular moiety.

Chemical Linkers

Chemical linkers may also be incorporated into the templated assembly reactants. The chemical linkers may be included between any of the moieties. Chemical linkers may optionally connect two or more of the moieties to introduce additional functionality or facilitate synthesis. The chemical linker can be a bond between any of the moieties. In some embodiments, the chemical linker can be between any of the nucleic acid recognition moiety and the selectively-reactive moiety, and the selectively-reactive moiety and the effector partial moiety. In one embodiment, the effector partial moiety includes a chemical linker capable of interacting with the selectively-reactive moiety to produce the active effector structure. The bond can include a physical interaction, such as chemical bonds (either directly linked or through intermediate structures), or a non-physical interaction or attractive force, such as electrostatic attraction, hydrogen bonding, and van der Waals/dispersion forces.

The chemical linkers may aid in facilitating spatial separation of the moieties, increasing flexibility of the moieties relative to each other, introducing a cleavage site or modification site to the templated assembly reactant, facilitating synthesis of the templated assembly reactant, improving physical or functional characteristics (such as solubility, hydrophobicity, charge, cell-permeability, toxicity, biodistribution, or stability) of a templated assembly reactant, or any combination of the above. In one embodiment, the chemical linker is derived from a cross-linker that facilitates connecting the templated assembly reactant moieties via bioconjugation chemistry. "Bioconjugation chemistry," as used herein, refers to the chemical synthesis strategies and reagents that ligate common functional groups together under mild conditions, facilitating the modular construction of multi-moiety compounds. Due to the mild reaction conditions, bioconjugate chemistry approaches can be suitable for ligating biomolecules, such as nucleic acids, peptides, or polysaccharides. Some non-limiting examples can include chains of one or more of the following: alkyl groups, alkenyl groups, amides, esters, thioesters, ketones, ethers, thioethers, disulfides, ethylene glycol, cycloalkyl groups, benzyl groups, heterocyclic groups, maleimidyl groups, hydrazones, urethanes, azoles, imines, haloalkyl groups, carbamates, or combinations of any of these.

In addition to chemical linkers between moieties, additional functionality may optionally be introduced to templated assembly reactants by the addition of accessory groups to the moieties. Some non-limiting examples of accessory groups can include appending a chemical tag or fluorophore to track the location of a templated assembly reactant or ligation product, or appending an agent that improves delivery of a templated assembly reactants to target compartments, such as cell-penetrating peptides, or stabilizing polyethylene glycol groups. Examples of non-limiting attachment points of accessory groups on suitable moieties are described herein. In one embodiment, any one or more of the nucleic acid recognition moiety, the selectively-reactive moiety, and the effector partial moiety can be functionalized with a chemical linker.

The nucleic acid recognition moiety of a templated assembly reactant may be attached to a chemical linker, effector partial moiety, or bio-orthogonal reactive moiety at either end of the nucleic acid recognition moiety, or an internal portion of the nucleic acid recognition moiety. In one embodiment, the attachment point can be at one end of a nucleic acid recognition moiety oligomer, attached to a terminal unit of the oligomer directly or via a chemical linker, to prevent steric blockage of hybridization. In another embodiment, the attachment point can be at an internal point of the nucleic acid recognition moiety that does not interfere with hybridization, such as the oligomer backbone, or a part of a base. For example, the N-7 position of a guanine base can serve as the attachment point since it does not participate in base-pairing. The above attachment points may also be suitable positions for attachment of accessory groups to add functionality to the templated assembly reactant.

Synthesis of Targeted Templated Assembly Reactants

Figure 9:
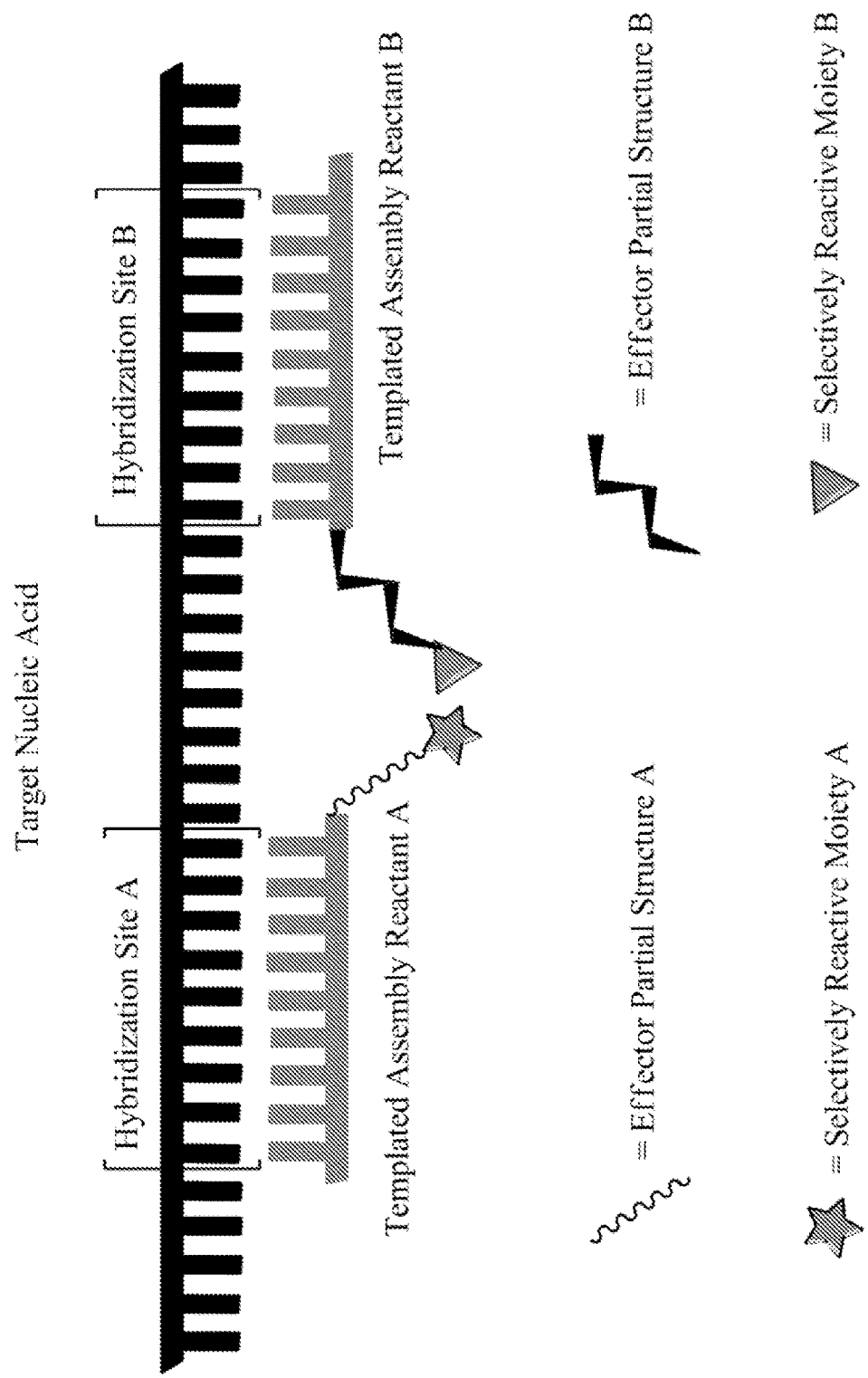
FIG. 9 is an illustration of targeted templated assembly products with multiple reactants, reactants A and B. Multiple nucleic acid recognition moieties hybridize to target sequences and allow reactants to combine to generate an active effector structure.

The method of synthesizing the template assembly composition includes generating at least one nucleic acid recognition moiety that is capable of binding a target nucleic acid sequence, generating at least one selectively-reactive moiety that is capable of binding the nucleic acid recognition moiety, and generating an effector partial moiety. These moieties are bound together using methods known in the art, such as bioconjugate chemistry, to produce complete templated assembly reactants. Moieties in different templated assembly reactants may be bound or attached together in different configurations, provided that the templated assembly reactant maintains proper activity. In one embodiment, attachment points of other moieties to the nucleic acid recognition moiety in corresponding reactants can be designed so that the selectively-reactive moieties are brought into close spatial proximity upon hybridization of the corresponding reactants to target nucleic acid. For example, when two corresponding nucleic acid recognition moieties hybridize to a target nucleic acid, a terminal unit of one nucleic acid recognition moiety will be in close proximity to a terminal unit of the other nucleic acid recognition moiety. These terminal units serve as the point of attachment for additional moieties in this embodiment, as depicted in FIG. 9.

To synthesize the templated assembly reactants, three general approaches that may be employed to bind the moieties. 1) A functional moiety may be bound to another by direct incorporation of one moiety into the other during synthesis. For example, alkyne functionalized nucleotides may be incorporated into nucleic acid recognition moiety during solid phase phosphoramidite oligonucleotide synthesis. Azide and alkyne functionalized amino acids are also commercially available, which may be incorporated into effector partial structure peptides during solid phase Merrifield peptide synthesis, or incorporated into peptide nucleic acids in a nucleic acid recognition moiety utilizing the same chemistry. 2) A functional group contained in one pre-synthesized moiety may be chemically converted to create an additional moiety in situ. For example, a primary amine contained in a nucleic acid recognition moiety or effector partial moiety may be converted to an azide by diazotransfer. 3) Separate pre-synthesized moieties may be joined using bioconjugate chemistry techniques to covalently link suitable functional groups on the moieties. These functional groups may be present naturally on a moiety, or may be introduced by incorporation of a derivatized group during synthesis of a moiety.

Use of Nucleic Acid Templated Assembly Reactants to Selectively Generate Effector Products Diagnostic Evaluation of Corresponding Templated Assembly Reactant Diagnostic test evaluations of a set of corresponding templated assembly reactants and the subject may be employed. This evaluation may serve to determine if a particular set of templated assembly reactants is competent to produce an effector structure in a given subject. This may be useful if the templated assembly reactants have not been utilized previously, or if a current sample is significantly different from previous samples, e.g. the sample contains a lower level of target nucleic acid than previous samples. The diagnostic test evaluations can also detect the presence or absence of target nucleic acids in a sample, or the abundance of target nucleic acids in a sample. The diagnostic test evaluation may also determine if a nucleic acid target is accessible for templated assembly reactions, providing information about secondary structures of a nucleic acid target in a sample. In one embodiment, the competency of the nucleic acid recognition moiety, selectively-reactive moiety, and the effector partial moiety to produce the active effector structure can be determined.

Figure 10:
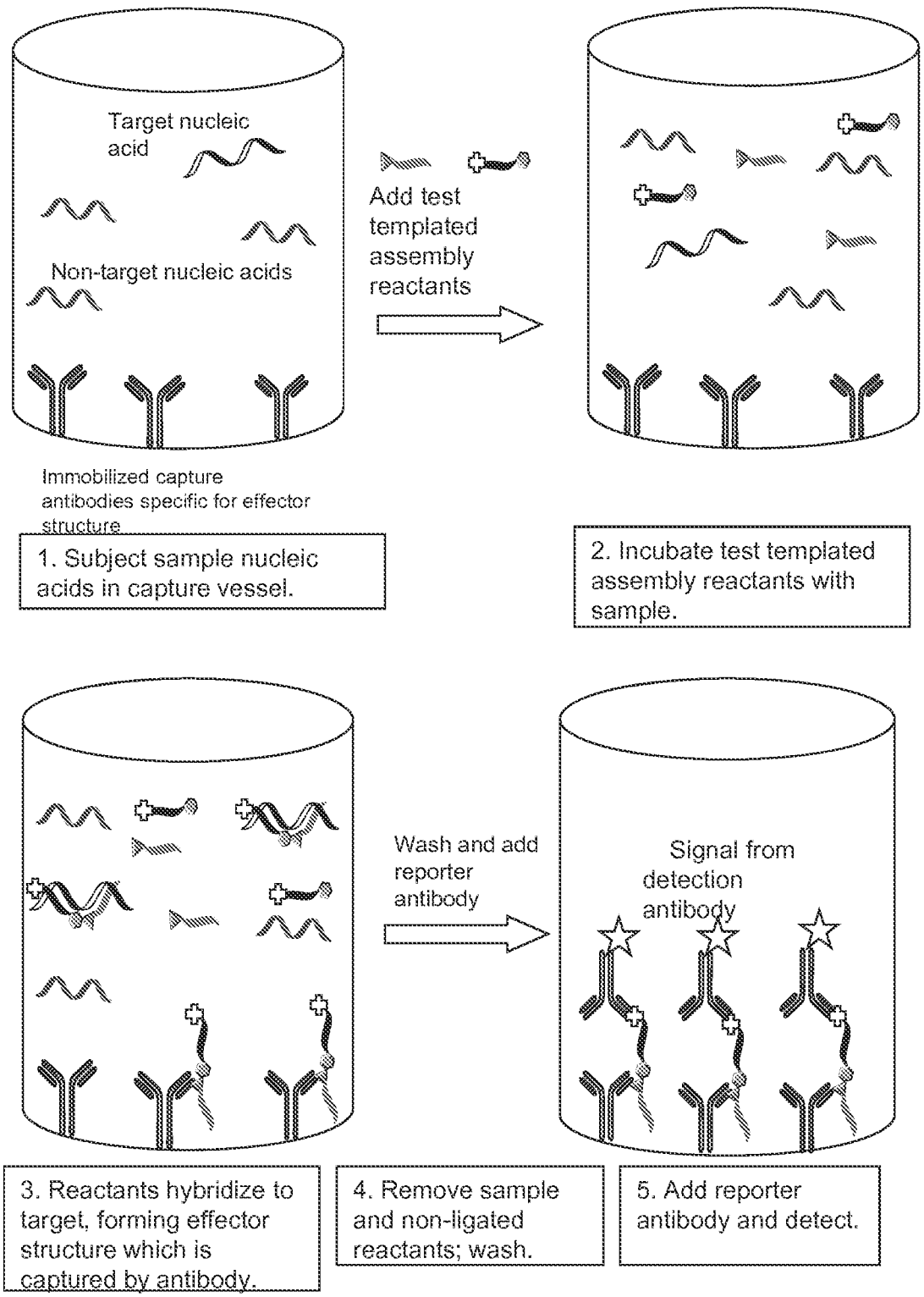
FIG. 10 is a diagram illustrating diagnostic evaluation of templated assembly reactants in a subject sample.

The diagnostic evaluation assay can include contacting the corresponding templated assembly reactants with a sample or multiple samples. See FIG. 10. If a convenient in vitro readout for the activity produced by the effector structure is available, templated assembly reactants may be administered to samples in vitro and monitored for activity produced by the effector structure. If in vitro detection of effector structure activity is not available, inconvenient, or costly, an alternative readout similar to sandwich enzyme-linked immunosorbent assays may be performed.

To perform the in vitro sandwich-style diagnostic evaluation assay, the following steps can be carried out. A sample or samples can be obtained from a subject to assay in vitro. Optionally, a target compartment sample (e.g., tumor biopsy) and non-target compartment negative control (e.g., a sample of healthy tissue) are obtained. Samples may be lysed in a suitable buffer to release nucleic acids, which may facilitate ease of use or increase the sensitivity of the assay. Templated assembly reactants can be administered to the sample or lysate. When target nucleic acid is present, templated assembly ligation products are formed. Ligated products can then be bound by an immobilized capture molecule. The molecule may be immobilized on a vessel, such as a microtiter plate well, or on a substrate, such as an agarose bead or magnetic bead that is mixed with assay medium. Sample material and non-ligated reactants can be removed and the immobilized complex can be washed. A detector molecule specific for an accessible part of the templated assembly ligation product can be incubated with the immobilized complex, and an appropriate detection readout can be performed. In one embodiment, specificity of the detector molecule, capture molecule, or both, may selectively detect a structure on the templated assembly ligation product that is not present on any templated assembly reactant before the templated assembly reaction occurs, such that the templated assembly ligation products can be captured and/or detected. For example, in FIG. 10, the specificity of the capture molecule selectively detects an effector product structure that is not present in the starting templated assembly reactants, ensuring that only templated ligation products are captured and detected.

In some embodiments, the specificity of the detector molecule can selectively detect a structure on one templated assembly reactant, and the specificity of the capture molecule can selectively detect a structure on a different templated assembly reactant, such that a templated assembly ligation product would include both structures and thus be detected. Sets of templated assembly reactants contained on a single compound, such as those depicted in FIG. 2C, may be incompatible with this embodiment.

Administration

Administration of sets of corresponding templated assembly reactants may vary according to the nature of the sample. One embodiment can include dispensing a targeted templated assembly reactants into a sample within a suitable vessel or chamber. In another embodiment, the sample may be dispensed into a vessel already containing the targeted templated assembly reactants. In yet another embodiment, the targeted template assembly reactants can be assembled in in vitro or in situ.

In some embodiments, the targeted template assembly reactants can be administered for templated assembly in vivo. To facilitate administration of the targeted templated assembly reactants to samples, prepared templated assembly reactants may be administered in any suitable buffer or formulation, optionally incorporating a suitable delivery agent, and contacted with the sample. Concentrated forms of a templated assembly reactant may be handled separate from its reactive counterpart, as product-generating reactions may occur in the absence of target template at high concentrations. Table 1 details guidelines for maximum acceptable concentrations of gymnotic (no delivery agent) templated assembly reactants comprised of various selectively-reactive moieties. If templated assembly reactants are contacted at concentrations above these thresholds, undesirable non-templated background reactions may be expected.

TABLE 1

Maximum concentrations for contact of templated assembly reactants, above which non-templated reaction levels may become undesirable.

| Bioorthogonal Reactive Chemistry | Maximum Concentration |
| --- | --- |
| Azide-Alkyne | <50 µM |
| Azide-Phosphine | <50 µM |
| Native Chemical Ligation | <1 mM |

Threshold concentrations of other templated assembly reactants may be determined empirically utilizing the templated assembly diagnostic evaluation assay disclosed.

In some embodiments, the likelihood of non-templated reactions may be reduced by administering a set of corresponding templated assembly reactants such that one reactant is administered first, then a time delay is observed before the corresponding templated assembly reactant is administered. This time delay may range from one minute to days, depending on the persistence of the templated assembly reactants in the system.

Certain delivery agents, such as transfection reagents such as cationic lipids, polyethyleneimine, dextran-based transfectants, or others known in the art, may cause condensation of the templated assembly reactants. Under these circumstances, templated assembly reactants may be prepared separate from the corresponding reactive templated assembly reactants and administered to the sample separately. Templated assembly reactants may also be administered gymnotically, dissolved in an appropriate buffer without addition of any additional delivery agent.

The templated assembly reactants may also be administered after formulation with a suitable delivery agent. A suitable delivery agent may enhance the stability, bioavailability, biodistribution, cell permeability, or other desirable pharmacologic property of the templated assembly reactants, or a combination of these properties. Delivery agents known in the art include, but are not limited to, polycationic transfection reagents, polyethyleneimine and its derivatives, DEAE-Dextran, other transfection reagents, salts, ions, buffers, solubilization agents, various viral vectors, liposomes, targeted liposomes, nanoparticles, carrier polymers, endosome disruptors, permeabilization agents, lipids, steroids, surfactants, dispersants, stabilizers, or any combination thereof.

Delivery of templated assembly reactants to target compartments may also be enhanced by covalent attachment of accessory groups to templated assembly reactants. Accessory groups that may enhance delivery may include compounds known to enhance the stability and biodistribution of compounds, such as polyethylene glycol (PEG); and enhance cell permeability of templated assembly reactants, including, but not limited to, cholesterol derivatives known in the art, endosome-disrupting agents known in the art, and cell-penetrating peptides, such as poly-cations such as poly-arginine or polylysine, peptides derived from the HIV tat protein, transportan, and peptides derived from the antenapedia protein (penetratin).

Administration of an effector product-triggered agent, such as an antibody or other effector product-detecting molecule, or effector product-detecting cell, may also be included. The administration can be part of the templated assembly procedure. It may be administered before, during, or after administration of templated assembly reactants, and by any method appropriate to the agent. In one embodiment, the effector structure-triggered agent is administered prior to administration of the templated assembly reactants to facilitate triggering of activity by effector structures as soon as they are formed and available for agent binding.

In some embodiments, multiple sets of corresponding reactants may be administered in parallel. These sets of reactants may bind to multiple hybridization sites on a single target nucleic acid, or bind to different target nucleic acids, or a combination thereof. The different sets of reactants may produce the same effector structure, thus increasing the level of activity generated by that effector structure by boosting its production, or the different sets of reactants may produce different effector structures, thus producing multivalent activity in the sample, or a combination thereof. When multiple sets of corresponding reactants are administered in parallel, reactants from different sets of corresponding reactants that have the same bio-orthogonal reactive group (or groups that do not react with each other, if different bio-orthogonal chemistries are employed for different sets of reactants) may be administered together, even at high concentrations, since they will not be reactive with each other. For example, if an azide-alkyne bio-othogonal reactive system is employed for each set of corresponding reactants, all of the azide-containing reactants may be formulated and administered together, and all of the alkyne-containing reactants may be formulated and administered together after sufficient dilution of the azides in the sample.

In some embodiments, the composition administered can include two or more sets of corresponding templated assembly reactants that include nucleic acid recognition moieties capable of binding two or more target nucleic acid sequences. Two or more target nucleic acid sequences may be found within the same gene transcript, or alternatively on distinct and separate transcripts. Two or more sets of corresponding templated assembly reactants recognizing distinct nucleic acid target sequences within the same cellular transcript may independently carry the same effector partial structures that react to form additional copies of the same effector products in a template-directed manner. The individual nucleic acid recognition moieties are linked to the selectively-reactive moiety.

In some embodiments, the composition administered can include two or more effector partial moieties that are each linked to selectively-reactive moieties, to produce two or more active effector structures. Production of two or more active effector structures can yield two or more effector activities, such as inducing an immune response, programmed cell death, apoptosis, necrosis, lysis, growth inhibition, inhibition of viral infection, inhibition of viral replication, inhibition of oncogene expression, modification of gene expression, inhibition of microbial infection, and inhibition of microbe replication, as well as combinations of these biological activities.

In some embodiments, the composition administered can include two or more sets of corresponding templated assembly reactants that include hybridization moieties capable of binding two or more target nucleic acid sequences. Two or more target nucleic acid sequences may be found within the same gene transcript, or alternatively on distinct and separate transcripts. Two or more sets of corresponding templated assembly reactants recognizing distinct nucleic acid target sequences within the same cellular transcript may independently carry the same or distinct effector partial structures that react to form additional copies of the same effector products in a template-directed manner. The inclusion of two or more effector partial moieties can produce two or more active effector structures to yield two or more effector activities, such as inducing an immune response, programmed cell death, apoptosis, non-specific or programmed necrosis, lysis, growth inhibition, inhibition of viral infection, inhibition of viral replication, inhibition of oncogene expression, modification of gene expression, inhibition of microbial infection, and inhibition of microbe replication, as well as combinations of these biological activities.

The abundance of target nucleic acid sequences may also limit the amount of active effector structure produced by templated assembly. In one embodiment, there is an average of at least 5 copies of target nucleic acid per target compartment. The dosage and concentration of the composition administered can take the availability of the target nucleic acids into account.

In some embodiments, a method of delivering a composition to a pathogenic cell is disclosed. The method can include administering a therapeutically effective amount of a set or multiple sets of corresponding templated assembly reactant compositions to the pathogenic cell, binding the templated assembly reactant compositions to the target nucleic acid sequence, and generating active effector products. The composition can include at least one nucleic acid recognition moiety that binds a target nucleic acid sequence within the target pathogenic cell, at least one selectively-reactive moiety bound to the nucleic acid recognition moiety, and at least one effector partial moiety. In one embodiment, the method can also include detecting the presence or absence of the target nucleic acid sequence prior to administering the targeted templated assembly composition reactant compositions.

Pharmaceutical compositions may be administered by one of the following routes: oral, topical, systemic (e.g. transdermal, intranasal, or by suppository), or parenteral (e.g. intramuscular, subcutaneous, or intravenous injection). Compositions may take the form of tablets, pills, capsules, semisolids, powders, sustained release formulations, solutions, suspensions, elixirs, aerosols, or any other appropriate compositions; and comprise at least one compound in combination with at least one pharmaceutically acceptable excipient. Suitable excipients are well known to persons of ordinary skill in the art, and they, and the methods of formulating the compositions, may be found in such standard references as Remington: The Science and Practice of Pharmacy, A. Gennaro, ed., 20th edition, Lippincott, Williams & Wilkins, Philadelphia, Pa. Suitable liquid carriers, especially for injectable solutions, include water, aqueous saline solution, aqueous dextrose solution, and glycols.

Pharmaceutical compositions suitable for injection may include sterile aqueous solutions (where water soluble) or dispersions and sterile powders for the extemporaneous preparation of sterile injectable solutions or dispersion. In all cases, the composition must be sterile and must be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents. In many cases, isotonic agents can be included, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the composition containing the templated assembly reactants in the required amount in an appropriate solvent with one or a combination of ingredients enumerated above, as required. Generally, dispersions are prepared by incorporating the composition into a sterile vehicle which contains a basic dispersion medium and the required other ingredients from those enumerated above When the composition containing the templated assembly reactants is suitably protected, as described above, the composition can be formulated for oral administration, for example, with an inert diluent or an assimilable edible carrier. The composition and other ingredients can also be enclosed in a hard or soft shell gelatin capsule, compressed into tablets, or incorporated directly into the subject's diet. For oral therapeutic administration, the composition can be incorporated with excipients and used in the form of ingestible tablets, buccal tablets, troches, capsules, elixirs, suspensions, syrups, wafers, and the like. The percentage of the compositions and preparations can, of course, be varied. The amount of templated assembly reactants in such therapeutically useful compositions is such that a suitable dosage will be obtained.

It is especially advantageous to formulate compositions in dosage unit form for ease of administration and uniformity of dosage. Dosage unit form as used herein refers to physically discrete units suited as unitary dosages for the subjects to be treated. Each dosage contains a predetermined quantity of the templated assembly reactants calculated to produce the amount of active effector product in association with the required pharmaceutical carrier. The specification for the novel dosage unit forms is dependent on the unique characteristics of the targeted templated assembly composition, and the particular therapeutic effect to be achieved. Dosages are determined by reference to the usual dose and manner of administration of the ingredients.

The term "pharmaceutically acceptable" refers to a material that is not biologically or otherwise unacceptable when used herein. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The term "pharmaceutically acceptable salt" means a salt prepared from a base or an acid which is acceptable for administration to a patient, such as a mammal (e.g., salts having acceptable mammalian safety for a given dosage regime). However, it is understood that the salts covered herein are not required to be pharmaceutically acceptable salts, such as salts of the templated assembly reactants that are not intended for administration to a patient. Pharmaceutically acceptable salts can be derived from pharmaceutically acceptable inorganic or organic bases and from pharmaceutically acceptable inorganic or organic acids. In addition, when a templated assembly reactant contains both a basic moiety, such as an amine, and an acidic moiety such as a carboxylic acid, zwitterions may be formed and are included within the term "salt" as used herein. Salts derived from pharmaceutically acceptable inorganic bases can include ammonium, calcium, copper, ferric, ferrous, lithium, magnesium, manganic, manganous, potassium, sodium, and zinc salts, and the like. Salts derived from pharmaceutically acceptable organic bases can include salts of primary, secondary and tertiary amines, including substituted amines, cyclic amines, naturally-occurring amines and the like, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids can include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids can include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphorsulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

One skilled in the art will appreciate further features and advantages of the disclosure based on the above-described embodiments. Accordingly, the disclosure is not to be limited by what has been particularly shown and described, nor by the examples set forth below. All publications and references cited herein are expressly incorporated herein by reference in their entirety. As used in this specification and the appended claims, the singular forms "a," "an," and "the" include plural references unless the content clearly dictates otherwise. The terms used in this disclosure adhere to standard definitions generally accepted by those having ordinary skill in the art. In case any further explanation might be needed, some terms have been further elucidated below.

The terms "active effector structure" and "effector structure" are used interchangeably herein and refer to the active portion of a templated assembly product that triggers a desired effect.

The term "base," as used herein, refers to a molecule containing a purine or pyrimidine group, or an artificial analogue, that forms a binding pair with another corresponding base via Watson-Crick or Hoogsteen bonding interactions. Bases further contain groups that facilitate covalently joining multiple bases together in a polymer, such as an oligomer. Non-limiting examples include nucleotides, nucleosides, peptide nucleic acid residues, or morpholino residues.

The terms "bind," "binds," "binding," and "bound," as used herein, refer to a stable interaction between two molecules that are close to one another. The terms include physical interactions, such as chemical bonds (either directly linked or through intermediate structures), as well as non-physical interactions and attractive forces, such as electrostatic attraction, hydrogen bonding, and van der Waals/dispersion forces.

The term "bioconjugation chemistry," as used herein, refers to the chemical synthesis strategies and reagents that ligate common functional groups together under mild conditions, facilitating the modular construction of multi-moiety compounds.

The term "chemical linker," as used herein, refers to a molecule that binds one templated assembly reactant to another templated assembly reactant or one moiety to another moiety on different compounds. A linker may be comprised of branched or unbranched covalently bonded molecular chains.

The phrase "non-traceless bio-orthogonal chemistry," as used herein, refers to a reaction involving selectively-reactive moieties in which part or all of the structure of the selectively-reactive moieties is retained in the product structure.

The term "effector partial moiety," as used herein, refers to a portion of a templated assembly reactant that contributes to the chemical structure of the effector structure in a product formed by nucleic acid templated assembly. An effector partial moiety may be a distinct portion of the reactant, or may include or be comprised of part or all of the nucleic acid recognition moiety and/or the selectively-reactive moiety.

The term "effector structure-triggered agent" as used herein refers to an exogenously-produced compound or cell capable of initiating a desired activity upon binding to an effector structure.

The phrase "nucleic acid recognition moiety" as used herein refers to a compound that facilitates sequence-specific binding to a target nucleic acid.

The phrase "nucleic acid templated assembly" as used herein refers to the synthesis of a product structure or structures on a target nucleic acid, such that product formation can be facilitated by templated assembly reactants being assembled in proximity when bound to the target nucleic acid.

The term "oligomer," as used herein, refers to a molecule comprised of multiple units where some or all of the units are bases capable of forming Watson-Crick or Hoogsteen base-pairing interactions, allowing sequence-specific binding to nucleic acids in a duplex or multiplex structure. Non-limiting examples include oligonucleotides, peptide nucleic acid oligomers, and morpholino oligomers.

The term "pathogenic cell" as used herein can refer to a cell that is capable of causing or promoting a diseased or an abnormal condition, such as a cell infected with a virus, a tumor cell, and a cell infected with a microbe, or a cell that produces a molecule that induces or mediates diseases that include, but are not limited to allergy, anaphylaxis, inflammation and autoimmunity.

The term "pharmaceutically acceptable" when used herein refers to a material that is not biologically or otherwise unacceptable. that can be incorporated into a composition and administered to a patient without causing unacceptable biological effects or interacting in an unacceptable manner with other components of the composition.

The term "pharmaceutically acceptable salt" means a salt prepared from a base or an acid which is acceptable for administration to a patient, such as a mammal (e.g., salts having acceptable mammalian safety for a given dosage regime).

The term "salt" as used herein can include salts derived from pharmaceutically acceptable inorganic acids and bases and salts derived from pharmaceutically acceptable organic acids and bases and their derivatives and variants thereof.

The term "sample," as used herein, refers to any system that templated assembly reactants can be administered into, where nucleic acid templated assembly may occur. Non-limiting examples may include living cells, fixed or preserved cells, whole organisms, tissues, tumors, lysates, or in vitro assay systems.

The term "selectively-reactive moiety" refers to the portion of a templated assembly reactant that enables formation of product, such as through a chemical reaction with a corresponding templated assembly reactant, on an adjacent templated assembly. For example, a selectively-reactive moiety can react readily with a corresponding selectively-reactive moiety, but does not readily react with natural biomolecules.

The phrases "set of corresponding reactants" or "corresponding templated assembly reactants" are referred to herein as templated assembly reactants that come together on a single target template to take part in a templated assembly reaction.

The term "superantigen," as used herein, refers to an antigen that binds to a broad subset of T cells that express a particular variable (V) region The phrase "traceless bio-orthogonal chemistry," as used herein, refers to a reaction involving selectively-reactive moieties in which a naturally occurring bond, for example an amide, is formed by elimination of part or all of the selectively-reactive moieties from the product structure.

The term "target compartment" as used herein refers to a cell, virus, tissue, tumor, lysate, other biological structure, spatial region, or sample that contains target nucleic acid, or a different amount of target nucleic acids than a non-target compartment.

The phrases "target nucleic acid sequence" and "target nucleic acid" are used interchangeably and refer to a sequence of units or nucleic acids which are intended to act as a template for nucleic acid templated assembly.

The term "templated assembly ligation product," as used herein, refers to the product structure or structures formed by interaction, binding or reaction of one or more nucleic acid templated assembly reactants.

The term "templated assembly reactant" as used herein refers to the nucleic acid recognition moiety that binds to a target nucleic acid template in a sequence-specific manner and participates in product formation during nucleic acid templated assembly.

Also included herein are "derivatives" or "analogs" such as salts, hydrates, solvates thereof, or other molecules that have been subjected to chemical modification and maintain the same biological activity or lack of biological activity, and/or ability to act as a templated assembly reactant, or function in a manner consistent with a templated assembly reactant.

EXAMPLES

Example 1: Evaluation of Effect of Nucleic Acid Recognition Moiety

A set of azide-cyclooctyne based corresponding reactants was evaluated for ability to participate in nucleic acid templated ligation reactions at various temperatures to determine the relationship between nucleic acid recognition moiety $T_m$, temperature of the sample environment, and reaction efficiency. Results were evaluated with gel electrophoresis of product as well as an ELISA-style sandwich assay. The target nucleic acid template represented sequence from tumor-associated viral transcript HPV16 E6/E7.

Templated assembly reactant nucleic acid recognition moieties were comprised of modified oligodeoxynucleotides. Sequences and predicted $T_m$ of oligonucleotides are shown in Table 2.

TABLE 2

Nucleic acid moieties and melting temperatures.

| Name | Sequence | $T_m$ | SEQ ID NO |
|---|---|---|---|
| Oligo-1.1 | 5' TAACTGTCAAAAGCCACTGTGTCCTGAA GAAAAGCAAAGACATCTGGACAAAAAGC 3' | N/A | 1 |
| Oligo-1.2 | 5'-FAM-CCAGATGTCTTTGCT-Azide 3' | 39° C. | 2 |
| Oligo-1.3 | 5' Amine-TTTCTTCAGGACACAG-biotin-3' | 41° C. | 3 |

Oligo-1.1 represents a sequence from position 415 to 470 of Genbank accession # U89348.1, the reference sequence for human papilloma virus 16 (HPV16) isolated from the Caski cell line. HPV is found in nearly 100% of human cervical cancers. This position in the sequence is from gene E6/E7, which is expressed in almost all HPV-induced cervical cancers. Oligo-1.2 represents the reverse complement of the sequence from position 447-461 of Genbank # U89348.1. It is capable of hybridization to Oligo-1.1. It contains carboxyfluorescein (FAM) at the 5' end and an azide at the 3' end.

Oligo-1.3 represents the reverse complement of the sequence from position 431-446 of Genbank # U89348.1. It is capable of hybridization to Oligo-1.1 adjacent to the hybridization site of Oligo-1.2. It contains a primary amine at the 5' end and biotin at the 3' end.

The bio-orthogonal azide group on Oligo-1.2 was incorporated at the time of synthesis. Oligo-1.3 was functionalized with Dibenzylcyclooctyne-sulfo-NHS ester (DBCO-NHS), obtained from Click Chemistry Tools. DBCO-NHS was dissolved in DMSO to produce a 100 mM stock. A 1 mM stock solution of Oligo-2 was prepared in 1×PBS Buffer (137 mM NaCl, 3 mM KCl, 12 mM phosphates, pH 7.4). A 20× molar excess of DBCO was mixed with 100 nmole of Oligo-1.2 and incubated at room temperature for 4 hours. The reaction was then quenched with 1M Tris-HCl pH 8.0 to a final concentration of 100 mM Tris. Product was purified over a Sephadex G-15 column and ethanol precipitated by standard methods using sodium acetate.

Figure 11:
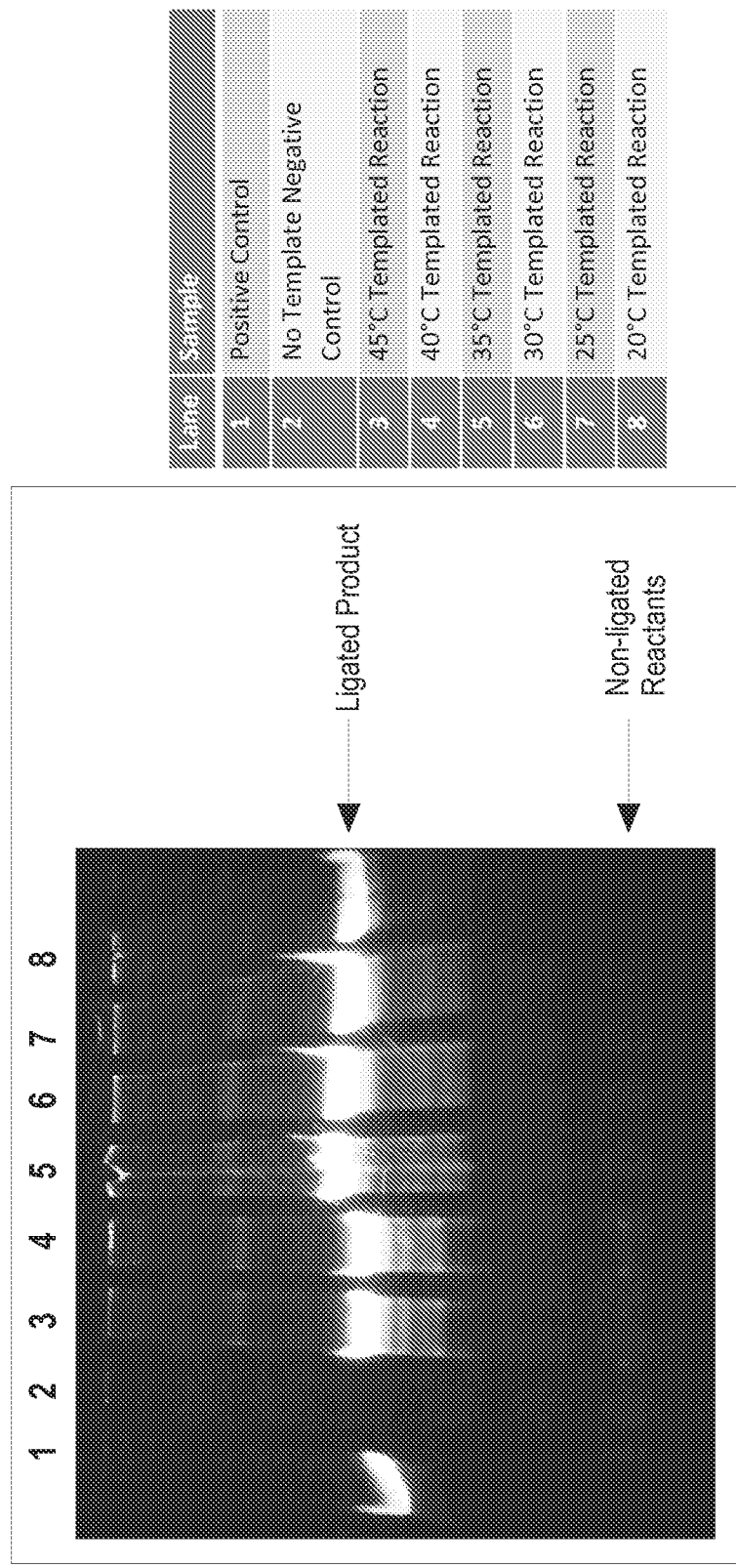
FIG. 11 is a gel showing ligation products produced by nucleic acid templated assembly at various hybridization temperatures, with little non-ligated product remaining after templating.

Nucleic acid templated ligation reactions were prepared in standard PCR tubes by first mixing 40 pmol Oligo-1.1 and 40 pmol Oligo-1.2 in 39 uL 1×PBS. This solution was allowed to equilibrate in a thermal cycler programmed to maintain the experimental temperature for 15 minutes before addition of 40 pmol of Oligo-1.3-DBCO conjugate. Reactions were incubated for 5 minutes before quenching the reaction with Tris(2-carboxyethyl)phosphine hydrochloride (TCEP). A reaction at room temperature that omitted template was included as a negative control. A ligated product generated by incubating Oligo-1.2 and Oligo1.3 at high concentration was included as a positive control. Experimental ligations were incubated at 20° C., 25° C., 30° C., 35° C., 40° C. (~Oligo $T_m$'s), 45° C. (>Oligo $T_m$'s). Immediately after quenching the final reaction, 20 uL of each product and control was run on a 15% denaturing PAGE gel for 3 hours at 20 W. The gel, seen in FIG. 11, was stained with SYBR Gold (Life Technologies).

In addition, the remainder of the sample (20 uL) was evaluated in an ELISA sandwich assay, capturing the biotinylated end of the ligated product on a streptavidin plate and detecting the FAM-labeled end of the product with an anti-FAM-peroxidase antibody (neither reactant possesses both of these groups, only a ligated product generates signal.) TMB-based chromogenic absorbance detection at 450 nm provided in Table 3.

TABLE 3

Templated reaction temperatures and chromogenic absorbances.

| Reaction | Corrected A450 |
|---|---|
| Positive Control | 0.322 |
| No Template Negative Control | 0.055 |
| 45° C. Templated Reaction | 0.447 |
| 40° C. Templated Reaction | 0.512 |
| 35° C. Templated Reaction | 0.621 |
| 30° C. Templated Reaction | 0.667 |
| 25° C. Templated Reaction | 0.591 |
| 20° C. Templated Reaction | 0.501 |

Cyclooctyne-based templated assembly reactants show efficient template-dependent product formation, even at reaction temperatures slightly above calculated reactant $T_m$. A sandwich style ELISA readout correlates well with gel electrophoresis results.

Example 2: Single Base Mutant Discrimination and Target Abundance Discrimination Corresponding reactants with cyclooctyne click and non-traceless Staudinger groups were evaluated for capability of:
discriminating single base mutants in an oncogene sequence and
discriminating target abundance levels
Performance was evaluated in an in vitro system containing complex biological material (tumor cell lysate).

Target Templates: For single base mutant experiments and abundance level discrimination, the templated assembly reactants were targeted to a mutated version of the H-ras oncogene sequence, specifically a G to T mutation represented by position 167 in GenBank accession # M25876.1. Sequences are shown in Table 4. Oligo-2.1 below represents a target fragment of this sequence from position 137 to 186, with the mutation position in bold. Oligo-2.2 represents the wild-type version of this target fragment. Oligo-2.3 is a scrambled version of the mutant target fragment.

TABLE 4

Nucleic acid oligo sequences.

| Name | Sequence | SEQ ID NO |
|---|---|---|
| Oligo-2.1 | 5'-CGGAATATAAGCTGGTGGTGGTGGG CGCCGTCGGTGTGGGCAAGAGTGCG-3' | 4 |
| Oligo-2.2 | 5'-CGGAATATAAGCTGGTGGTGGTGGG CGCCGGCGGTGTGGGCAAGAGTGCG-3' | 5 |
| Oligo-2.3 | 5'-GGGTTACGTGGAGGCGCTCTGTGAA TTGAGTGAGCAGGCGGGGTGGGCCA-3' | 6 |

Complex Lysate for Reaction Buffer: For each evaluation reaction, the subject material consisted of a HeLa cell lysate spiked with the appropriate oligo target. HeLa cell lysate was prepared by lysing 1×10⁶ HeLa cells in 250 uL lysis buffer (20 mM Tris pH 7.5, 150 mM NaCl, 1 mM EDTA, 1% NP-40, 1% Sodium Deoxycholate, 0.1% SDS, protease inhibitors, pancreatic RNase inhibitor), mixing, and pelleting debris. HeLa cells are negative for the experimental H-ras mutation, while providing a complex biochemical environment for nucleic acid templated assembly reactions.

Templated Assembly Reactant Synthesis: Templated assembly of nucleic acid recognition moieties for the H-ras reactants were comprised of oligodeoxynucleotides as shown in Table 5.

TABLE 5

Nucleic acid moieties and melting temperatures.

| Name | Sequence | $T_m$ | SEQ ID NO |
|---|---|---|---|
| Oligo-2.4 | 5'-DIG-ACACCGACGGC-Azide-3' | 38° C. | 7 |
| Oligo-2.5 | 5'-Amine-CCCACCACCAC-Biotin-3' | 38° C. | 8 |

An amine group was incorporated into Oligo-2.5 to facilitate attachment of bio-orthogonal reactive groups. DIG (dioxygenin) and biotin were incorporated into the oligonucleotides as the effector partial groups for detection.

Oligo-2.4 has a hybridization site at positions 173 to 163 on GenBank accession # M25876.1. Oligo-2.5 has a hybridization site at positions 161-151 on GenBank accession # M25876.1. Oligo-2.4 includes the site of the H-ras mutation under investigation; it is perfectly complementary for target template Oligo-2.1 and has a single base mismatch with target template Oligo-2.2.

Bio-orthogonal reactive groups were conjugated to Oligo-2.5 using the reactive 5' amine group. DBCO NHS ester was conjugated to Oligo-2.5 by the method described in Example 1. A non-traceless Staudinger phosphine group was conjugated to Oligo-2.5 using sulfo-NHS-Phosphine (Thermo Fisher Scientific) according to the manufacturer's recommended protocol, producing the phosphine conjugate product:

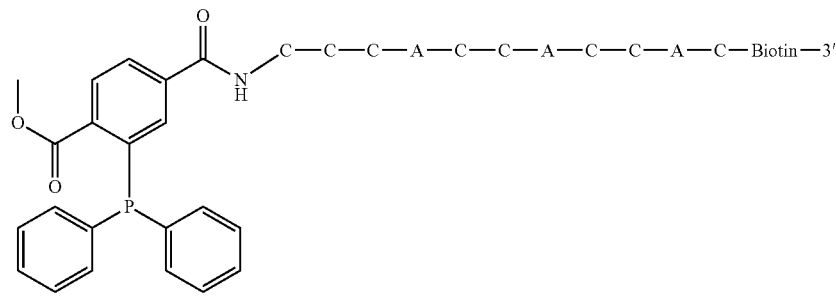

Two sets of corresponding templated assembly reactants specific for mutant H-ras were thus produced: Azide-Cyclooctyne H-ras: Oligo-2.4 and Oligo-2.5-DBCO Conjugate and Azide-Phosphine H-ras: Oligo-2.4 and Oligo-2.5-Phosphine Conjugate.

Evaluation of Mismatch Discrimination: Each set of templated assembly reactants was evaluated for templating capability on each of the oligonucleotide targets Oligo-2.1 (H-ras mutant), Oligo-2.2 (H-ras wild type), and Oligo-2.3 (scrambled control). 40 pmol each of reactant oligonucleotides and 40 pmol template target oligonucleotide were added to 39 uL of HeLa cell lysate at 37° C. and mixed. Reactions were incubated for 5 minutes at 37° C. before quenching with Tris(2-carboxyethyl)phosphine hydrochloride (TCEP).

Extent of templated assembly product formation was evaluated in an ELISA sandwich assay, capturing the biotinylated end of the ligated product on a streptavidin plate and detecting the DIG-labeled end of the product with an anti-DIG-peroxidase antibody (neither reactant possesses both of these groups, only a ligated product generates signal.) TMB-based chromogenic absorbance detection at 450 nm provided the readout. Corrected absorbance values, representing averages of triplicates of each reaction, are presented in Table 6.

TABLE 6

Detection of chromogenic absorbance.

| Reactants | Template | Corrected A450 |
|---|---|---|
| Azide-Cyclooctyne H-ras | Oligo-2.1 Mutant Perfect Match | 0.267 |
| Azide-Cyclooctyne H-ras | Oligo-2.2 Wild Type Mismatch | 0.065 |
| Azide-Cyclooctyne H-ras | Oligo-2.3 Scrambled | 0.027 |
| Azide-Phosphine H-Ras | Oligo-2.1 Mutant Perfect Match | 0.114 |
| Azide-Phosphine H-Ras | Oligo-2.2 Wild Type Mismatch | 0.017 |
| Azide-Phosphine H-Ras | Oligo-2.3 Scrambled | 0.002 |

Both cyclooctyne-based and non-traceless Staudinger-based templated assembly reactants can discriminate single base mismatches on a target template in a complex reaction environment.

Evaluation of Detection of Target Template Relative Abundance: Azide-cylooctyne H-ras templated assembly reactants were evaluated for the ability to detect relative abundance of perfectly matched target template in a complex reaction mixture. 40 pmol of Oligo-2.4 and variable amounts of target template Oligo-2.1 were added to 39 uL of HeLa cell lysate at 37° C. and incubated for 20 minutes. 40 pmol of Oligo-2.5-DBCO conjugate was then added, and reactions were incubated for 5 minutes at 37° C. before quenching with Tris(2-carboxyethyl)phosphine hydrochloride (TCEP). The ELISA sandwich assay was used to detect ligation product. Corrected absorbance values representing averages of triplicates of each reaction are presented in Table 7.

TABLE 7

Detection of ELISA sandwich assay.

| Amount of Target Template (pmol) | Corrected A450 |
|---|---|
| 0 | 0.000 |
| 5 | 0.012 |
| 10 | 0.029 |
| 15 | 0.082 |
| 20 | 0.151 |
| 25 | 0.170 |
| 30 | 0.211 |
| 35 | 0.238 |
| 40 | 0.238 |

Under template-limiting conditions, extent of templated assembly product formation correlates with amount of template present in a complex reaction mixture.

Example 3: Azide-Cyclooctyne Nucleic Acid Templated Assembly in Living Cells A set of corresponding reactants specific for the HPV16 E6/E7 gene were transfected into Caski cells to evaluate non-traceless nucleic acid templated assembly on tumor-associated targets in living cells. Sandwich enzymatic detection was used to confirm that templated assembly ligation product was preferentially formed in Caski cells rather than related cell lines lacking HPV16 E6/E7 sequence Templated assembly reactant of nucleic acid recognition moieties were prepared as 2-O-methyl modified oligoribonucleotides to prevent degradation by nucleases in the cells or cell culture medium. Oligoribonucleotide sequences are provided in Table 8.

TABLE 8

Nucleic acid moieties and melting temperatures.

| Name | Sequence | $T_m$ | SEQ ID NO |
|---|---|---|---|
| Oligo-3.1 | 5'-FAM-CCAGAUGUCUUUGCU-Azide-3' | 39° C. | 4 |
| Oligo-3.2 | 5'-Amine-UUUCUUCAGGACACAG-Biotin3' | 41° C. | 5 |

Oligo-3.1 represents a sequence from position 447 to 461 of Genbank accession # U89348.1, the reference sequence for human papilloma virus 16 (HPV16) isolated from the Caski cell line. HPV is found in nearly 100% of human cervical cancers. This position in the sequence is in gene E6/E7, the mRNA of which is expressed in almost all HPV-induced cervical cancers.

Oligo-3.2 represents the reverse complement of the sequence from position 431-446 of Genbank # U89348.1.

The FAM (carboxyfluorescein) detection group and azide bio-orthogonal moiety in Oligo-3.1 was incorporated at the time of oligoribonucleotide synthesis by incorporation of a FAM-phosphoramidite at the 5' end and conjugation of NHS-azide to a 3' amine.

Oligo-3.2 was synthesized with a 5' amine function to facilitate conjugation to the bio-orthogonal reactive group. Oligo-3.2 was conjugated at the amine with Dibenzylcyclooctyne-sulfo-NHS ester (DBCO-NHS), obtained from Click Chemistry Tools. DBCO-NHS was dissolved in DMSO to produce a 100 mM stock. A 1 mM stock solution of Oligo-3.2 was prepared in 1×PBS Buffer (137 mM NaCl, 3 mM KCl, 12 mM phosphates, pH 7.4). A 20× molar excess of DBCO was mixed with 100 nmole of Oligo-3.2 and incubated at room temperature for 4 hours. The reaction was then quenched with 1M Tris-HCl pH 8.0 to a final concentration of 100 mM Tris. Product was purified over a Sephadex G-15 column and ethanol precipitated by standard methods using sodium acetate. The ethanol precipitate did not form readily. The sample required incubation for 24 hours in a dry ice-ethanol bath at −78° C. to fully precipitate. Purification by HPLC yielded the Oligo-3.2-DBCO conjugate product.

Caski and HeLa cell lines were cultured in DMEM medium with 10% heat inactivated fetal bovine serum. For each experimental condition, $1\times10^6$ cells were plated in a T-25 flask 24 hours before transfection. A flask from each cell line was transfected with both templated assembly reactants (experimental), and Caski flasks were also transfected with each one of the reactants in isolation as well (negative controls).

Lipofectamine 2000 (Invitrogen) was used as the transfection reagent in accordance with the manufacturer's instructions Immediately prior to transfection, cell flasks were washed with 1×PBS and Optimem serum-free medium was added as the growth medium. Oligo-3.1 and Oligo-3.2-DBCO conjugate were resuspended in 1×PBS to a concentration of 100 uM. For each experimental flask, 1.1 uL of Oligo-3.1 was incubated with 275 uL of Optimem serum-free medium (Invitrogen). Separately, 11 uL of Lipofectamine 2000 was incubated with 275 uL of Optimem serum-free medium for 15 minutes. The Oligo-3.1 solution and the Lipofectamine solution were then mixed and incubated for 20 minutes. 500 uL of the Oligo-3.1-Lipofectamine transfection solution was then dispensed to the experimental flask. The transfection process above was repeated for the Oligo-3.2-DBCO conjugate, with the Oligo-3.2-DBCO-Lipofectamine transfection solution being dispensed to the flask 30 minutes after dispensing the corresponding reactant.

After 4 hours the serum-free medium was removed and replaced with DMEM+10% FBS.

Twenty-four hours after transfection cells were washed 3 times with 1×PBS and briefly treated with trypsin to dislodge cells from the substrate. Cells were then pelleted by centrifugation, with the pellet washed twice with 1×PBS. Pellets were then stored frozen until further processing.

A sandwich-style recovery and detection technique was used to detect ligated templated assembly product. Cell pellets were lysed in 5000 μL, RIPA buffer (50 mM Tris-HCl pH 7.4, 150 mM NaCl, 1% Triton x-100, 1% Sodium deoxycholate, 0.1% SDS, 1 mM EDTA, 1 mM $Na_3VO_4$, 1 μg/ml leupeptin) and centrifuged to removed debris. 300 μL of the cleared lysate was applied to a well of a streptavidin coated plate (Thermo Fisher Scientific) and incubated for 3 hours with shaking. The wells were washed 3 times in accordance with the manufacturer's instructions, and a 1:5000 dilution of anti-FAM horseradish peroxidase conjugate antibody (Life Technologies) in TBST was added to the wells and incubated at room temperature for 3 hours with shaking. The antibody solution was removed, wells washed 3 times, and signal developed with the Ultra TMB-ELISA Substrate Kit (Thermo Fisher Scientific) according to the manufacturer's instructions. Absorbance values for transfected samples are presented in Table 9.

TABLE 9

Transfection of cells with reactants and growth absorbances.

| Cell Line | Reactants Transfected | Corrected Absorbance A450 |
|---|---|---|
| Caski | Both Reactants | 0.237 |
| Caski | Azide Only | 0.003 |
| Caski | DBCO Only | 0.012 |
| HeLa | Both Reactants | 0.042 |

Caski cells transfected with both templated assembly reactants generated an appreciable positive signal in the detection assay for ligated product, confirming that nucleic acid templated assembly has selectively occurred in target cells.

Example 4: Synthesis Via Traceless Staudinger Ligation of a Non-Endogenous Peptide in Living Cells Traceless Staudinger-based nucleic acid templated assembly was carried out in living cells, using HPV16 E6/E7 mRNA as the target nucleic acid and creating the FLAG peptide epitope as an effector structure.

Templated assembly reactants were synthesized that allowed production of the FLAG peptide epitope (DYKDDDDK) in the presence of HPV16 E6/E7 target mRNA sequence in cells. The hybridization sites of HPV E6/E7 were chosen to be the same as those in Example 3. Traceless phosphinomethanethiol bio-orthogonal reactive chemistry was utilized. Since the four N-terminal residues of the FLAG epitope have been reported to be the key residues for binding of the antibody used for effector structure detection (Rooslid et al. 2006), the effector partial moieties were chosen such that they disrupted this 4-residue region to prevent detection of non-ligated reactant.

The nucleic acid recognition, bio-orthogonal reactive, and effector partial moieties of Templated Assembly Reactant 4A were synthesized separately, then conjugated via bioconjugate chemistry methods.

Nucleic acid recognition moiety 4A consisted of 2-O-methyl oligoribonucleotides to provide nuclease resistance, functionalized with a 3' thiol to provide for conjugation to other moieties. The hybridization site on HPV16 E6/E7 mRNA was positions 447 to 461 of Genbank accession # U89348. Oligoribonucleotide sequences are provided in Table 10.

TABLE 10

Nucleic acid recognition moiety and melting temperature.

| Name | Sequence | $T_m$ | SEQ ID NO |
|---|---|---|---|
| Oligo-4.1 | 5'-CCAGAUGUCUUUGCU-Thio-3' | 39° C. | 6 |
| Oligo-4.2 | 5'-Amine-UUUCUUCAGGACACAG-Biotin-3' | 41° C. | 7 |

All nucleotides in Oligo-4.1 and Oligo-4.2 were 2-O-methyl ribonucleotides. The 3' thiol modification was introduced at the time of synthesis.

A water soluble phosphinomethanethiol, bis(m-N,N-dimethylaminomethylphenyl)phosphinomethanethiol, served as the bio-orthogonal reactive moiety of templated assembly reactant 4A:

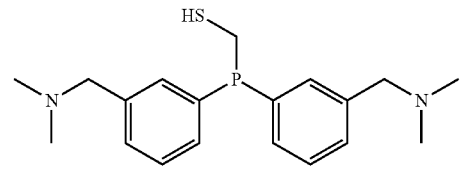

This product was synthesized as described (Tam et al., Bioorg Med Chem, 2009. 17(3): p. 1055-63), with an overall yield of 5%.

The effector partial moiety of reactant 4A was comprised of the aspartic acid-tyrosine dipeptide (DY). To facilitate conjugation of this peptide to the bio-orthogonal reactive group, it was synthesized on diaminobenzoyl-linker Rink Amide AM resin, as described in (Blanco-Canosa, Dawson 2008), and available commercially from Novabiochem. After synthesis of the DY peptide on this resin using standard methods, the linker is activated as described with p-nitrophenyl chloroformate followed by DIPEA. The peptide was then removed from the linker using standard $TFA/H_2O/TIS$ cleavage, yielding a C-terminal N-acylurea suitable for coupling with Bio-orthogonal Reactive Group 4A via thioester formation:

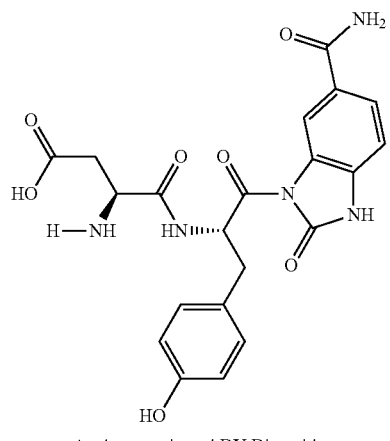

Acylurea-activated DY Dipeptide 1.0 mg (2.2 umol) of acylurea-activated DY dipeptide Effector partial Moiety 4A was reacted with 1.2 mg (3.3 umol) of Bioorthogonal Reactive Group A in a total of 1 mL Thioester Ligation Buffer (0.2M Phosphate Buffer, 6M guanidine HCl, 0.2M 4-mercaptophenylacetic acid, 0.02M TCEP, pH 7.0) and incubated at room temperature for 4 hours. The product was purified by HPLC, yielding 1.0 mg of thioester product (73% yield). The 1.0 mg thioester product was reacted with 10 molar equivalents of the bifunctional crosslinker SMCC (Pierce) in N,N-dimethylformamide (DMF) at room temperature for 2 hours. Product was purified by HPLC, yielding 1.1 mg (1.3 umol) of maleimide-bearing intermediate product. This product was resuspended in 260 uL DMF. 2 uL of this resuspension (10 nmol) was added to an equimolar amount of thiol-deprotected Oligo-4.1 in 48 uL 1×PBS and incubated for 2 hours at room temperature. The product was purified by HPLC. MALDI mass spectrometry analysis gave a product m/z of 5984.3 (expected 5977.21).

The bio-orthogonal reactive moiety of Reactant 4B was incorporated as part of the effector partial moiety during synthesis. Nucleic Acid Recognition Moiety 4B was synthesized separately, then conjugated via bioconjugate chemistry methods to the other moieties.

Nucleic Acid Recognition moiety 4B consisted of 2-O-methyl oligoribonucleotides to provide nuclease resistance, functionalized with a 5' amine to provide for conjugation to other moieties and a 3' biotin to facilitate isolation and detection of product. The hybridization site on HPV16 E6/E7 mRNA was positions 447 to 461 of Genbank accession # U89348 for oligo-4.1; 431-446 of Genbank # U89348 for oligo 4.2.

The effector partial moiety of Reactant 4B must reconstitute the remainder of the FLAG peptide that Reactant 4A does not provide. It therefore includes the peptide sequence KDDDDK. The N-terminal group must be an α-azido amino acid in order to react with the traceless phosphine bio-orthogonal reactive moiety on Reactant 4A to produce a native peptide bond, so the N-terminal lysine was incorporated as (S)-2-Azido-6-(Boc-amino)hexanoic acid (Sigma Aldrich). Additionally, a C-terminal cysteine was included to facilitate conjugation to Nucleic Acid Recognition Moiety 4A via the thiol. Thus, standard peptide synthesis was utilized to produce a moiety of the form: $N_3$-KDDDDKC. This peptide was purified by HPLC. MALDI mass spectrometry analysis gave a product m/z of 864.21 (expected 863.31). The bifunctional cross-linker SMCC (Thermo Fisher Scientific) was used to conjugate the primary amine group of Nucleic Acid Recognition Moiety 4B to the thiol of Bio-orthogonal-Effector Partial Moiety 4B. First, 20 nmol of Oligo-4.2 in 100 uL 1×PBS was mixed with 20 molar equivalents of SMCC dissolved in 2 uL DMF. The reaction proceeded at room temperature for 2 hours, then the product was purified over a Sephadex G-15 column (Sigma Aldrich). The purified product was used immediately in a reaction with 20 nmol (0.02 mg) the azido-peptide product in 1×PBS. The reaction proceeded for 3 hours at room temperature, then purified by HPLC. MALDI mass spectrometry analysis gave a product m/z of 6611.94 (expected 6607.31).

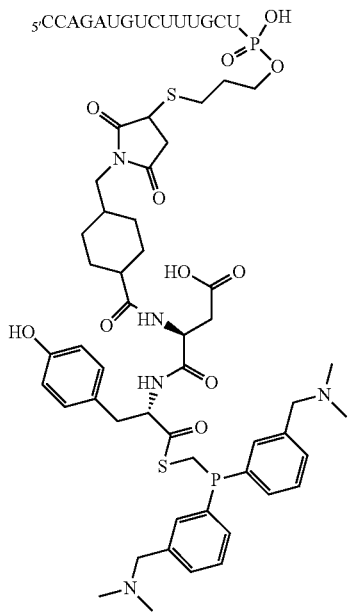

Templated Assembly Reactant 4A

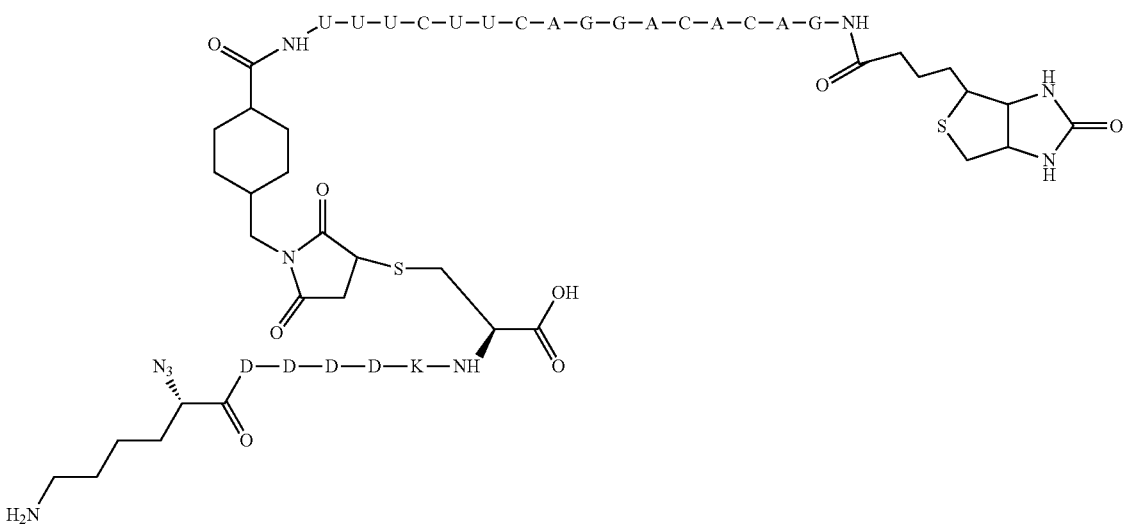

Templated Assembly Reactant 4B

Transfection conditions and procedure were identical to those used in Example 3, except that no transfections were performed with only one reactant. An additional cell line, C33A cervical cancer cells that do not harbor any strain of HPV, were included as an additional negative control. Transfection flask set up is described in Table 11.

TABLE 11

Transfection conditions.

| Cell Line | Reactant 4A Transfected | Reactant 4B Transfected |
|---|---|---|
| Caski | 0.1 nanomoles | 0.1 nanomoles |
| HeLa | 0.1 nanomoles | 0.1 nanomoles |
| C33A | 0.1 nanomoles | 0.1 nanomoles |

Cell harvest and detection with a sandwich style assay in wells of a streptavidin-coated ELISA plate was carried out identically to Example 3, with the exception that the detection antibody added was Monoclonal Anti-FLAG® M2-Peroxidase (Sigma Aldrich) diluted 1:10,000. Absorbance values obtained for detection of the FLAG epitope ligation product in each cell line are given in Table 12.

TABLE 12

Absorbance values.

| Cell Line | HPV16 Status | Corrected Absorbance A450 |
|---|---|---|
| Caski | Positive | 0.053 |
| HeLa | Negative | 0.019 |
| C33A | Negative | 0.011 |

FLAG peptide epitope product is preferentially formed by traceless nucleic acid templated assembly in cells harboring target nucleic acid sequence.

Example 5: Stimulation of Antigen-Specific Immune Cells by Traceless Staudinger-Based Nucleic Acid Templated Assembly of a Non-Endogenous Peptide Antigen in Tumor Cells Traceless Staudinger-based nucleic acid templated assembly was carried out in living tumor cells, using HPV16 E6/E7 mRNA as the target nucleic acid and creating the ELA peptide epitope (amino acid sequence: ELAGIGILTV) as an effector structure. This peptide epitope is not naturally present in any of the tumor cell lines utilized for this study. The ELA peptide binds to HLA-A2 molecules, and within this context may be displayed on the tumor cell surface for recognition by T cells specific for ELA-HLA complexes. In this study, treatment of tumor cells harboring HPV16 E6/E7 RNA with templated assembly reactants elicited selective stimulation of ELA antigen-specific immune cells.

Templated assembly reactants were synthesized that allowed production of the ELA peptide epitope (ELAGIGILTV) in the presence of HPV16 E6/E7 target mRNA sequence in cells. The hybridization sites of HPV E6/E7 were chosen to be the same as those in Examples 3 and 4.

Traceless phosphinomethanethiol bio-orthogonal reactive chemistry was utilized. To facilitate cellular protease processing of the ligated product and loading of the effector peptide into MHC molecules, the effector structure peptide was flanked on either end by additional amino acids as described in Le Gall et al., 2007 [1], so that the peptide produced in the ligated product before proteasomal cleavage was DRWEKELAGIGILTVKYKLKC. (This includes a C-terminal cysteine to facilitate templated assembly reactant synthesis.)

To determine if conjugation of different amino acids to bio-orthogonal groups would have a significant impact on the templated assembly process, two different sets of templated assembly reactants were prepared, which differed only in how the effector structure peptide was distributed between the corresponding reactants. Thus in one set, Templated Assembly Reactant 5A included effector partial peptide DRWEKELAGI, while Templated Assembly Reactant 5B included peptide GILTVKYKLKC. In the other set, Templated Assembly Reactant 5α included effector partial peptide DRWEKELAG, while Templated Assembly Reactant 5β included effector partial peptide IGILTVKYKLKC. The oligonucleotides used as nucleic acid recognition moieties and the biorthogonal groups were identical across the two sets.

Synthesis of Templated Assembly Reactants 5A and 5α

The nucleic acid recognition, bio-orthogonal reactive, and effector partial moieties of Templated Assembly Reactants 5A and 5α were synthesized separately, then conjugated via bioconjugate chemistry methods.

Nucleic acid recognition moiety 5A/α consisted of 2′-O-methyl oligoribonucleotides to provide nuclease resistance, functionalized with a 3′ thiol to provide for conjugation to other moieties. The hybridization site on HPV16 E6/E7 mRNA was positions 447 to 461 of Genbank accession # U89348. Oligoribonucleotide sequences are provided in Table 13.

TABLE 13

Nucleic acid recognition moiety and melting temperature of oligonucleotides utilized in Example 5.

| Name | Sequence | Tm | SEQ ID NO |
|---|---|---|---|
| Oligo-5.1 | 5′-CCAGAUGUCUUUGCU-Thio-3′ | 39° C. | 8 |
| Oligo-5.2 | 5′-Amine-UUUCUUCAGGACACAG-3′ | 41° C. | 9 |

All nucleotides in Oligo-5.1 and Oligo-5.2 were 2′-O-methyl ribonucleotides. The 3′ thiol modification was introduced at the time of synthesis.

The same water soluble phosphinomethanethiol, bis(m-N,N-dimethylaminomethylphenyl)phosphinomethanethiol, used in Example 4 also served as the bio-orthogonal reactive moiety of templated assembly reactants 5A and 5α. Again, this product was synthesized as described in Tam et al., 2009. [2]

The effector partial moiety of reactant 5A was comprised of the peptide DRWEKELAGI, while the effector partial moiety of reactant 5α was comprised of the peptide DRWEKELAG. As in Example 4, these peptides were synthesized on diaminobenzoyl-linker Rink Amide AM resin [3] to facilitate conjugation to the bio-orthogonal reactive group. After synthesis of the peptides on this resin using standard methods, the linker was activated as described with p-nitrophenyl chloroformate followed by DIPEA. The peptides were removed from the linker using standard TFA/H2O/TIS cleavage, yielding a C-terminal N-acylurea suitable for coupling with Bio-orthogonal Reactive Group 5A/α via thioester formation. For both DRWEKELAGI peptide effector partial moiety 5A and DRWEKELAG peptide effector partial moiety 5α, 2.0 mg (~1.4 µmol) of acylurea-activated peptide was reacted with 1.2 mg (3.3 µmol) of Bioorthogonal Reactive Group 5A/α in a total of 1 mL Thioester Ligation Buffer (0.2M Phosphate Buffer, 6M guanidine HCl, 0.2M 4-mercaptophenylacetic acid, 0.02M TCEP, pH 7.0) and incubated at room temperature for 4 hours. The products were purified by HPLC, yielding 2.1 mg each of thioester product. 2.0 mg of each thioester product was reacted with 10 molar equivalents of the bifunctional crosslinker SMCC (Pierce) in 10% N,N dimethylformamide (DMF), 50 mM phosphate buffer pH 6.5 (to restrict conjugation to the N-terminal amine) at room temperature for 2 hours. Products were purified by HPLC, yielding the maleimide-bearing intermediate. 20 nmol of this material was added to an equimolar amount of thiol-deprotected Oligo-5.1 in 48 µL 1×PBS and incubated for 4 hours at room temperature. The products were purified by HPLC. MALDI mass spectrometry analysis of gave a product m/z of 6907.7 (expected 6897.29) for Templated Assembly Reactant 5A. MALDI analysis gave a product m/z of 6796.6 (expected 6784.21) for Templated Assembly Reactant 5α.

Synthesis of Templated Assembly Reactants 5B and 5β

As in Example 4, the bio-orthogonal reactive moiety of Reactants 5B and 5β were incorporated as part of the effector partial moiety during synthesis. Nucleic Acid Recognition Moieties 5B/β were synthesized separately, then conjugated via bioconjugate chemistry methods to the other moieties.

Nucleic Acid Recognition moiety 5B/β consisted of 2'-O-methyl oligoribonucleotides to provide nuclease resistance, functionalized with a 5' amine to provide for conjugation to other moieties. The hybridization site on HPV16 E6/E7 mRNA was positions 431-446 of Genbank # U89348 for oligo 5.2.

The effector partial moiety of Reactant 5B reconstitutes the remainder of the ELA peptide that Reactant 5A does not provide. It therefore includes the peptide sequence GILT-VKYKLKC. Likewise, the effector partial moiety of Reactant 5β is comprised of the peptide sequence IGILT-VKYKLKC. The N-terminal groups must be an α-azido amino acid in order to react with the traceless phosphine bio-orthogonal reactive moiety on Reactants 5A or 5α to produce a native peptide bond. Thus for Effector Partial Moiety 5B, the N-terminal glycine was incorporated as 2-azido acetic acid (Sigma Aldrich). For Effector Partial Moiety 5β, a 2-azido isoleucine was not commercially available, so a standard isoleucine amino acid at the N-terminus of the peptide was converted to the 2-azido form by treatment with the diazotransfer agent imidazole-1-sulfonyl azide hydrochloride as described in Hansen et al., 2012 [4]. In addition to the azido groups, a C-terminal cysteine was included in each peptide to facilitate conjugation to Nucleic Acid Recognition Moiety 5B/β via the thiol. Thus, standard peptide synthesis was utilized to produce a moiety of the form N3-GILTVKYKLKC for Templated Assembly Reactant 5B, and $N_3$-IGILTVKYKLKC for Templated Assembly Reactant 5β. These peptides were purified by HPLC.

The bifunctional cross-linker SMCC (Thermo Fisher Scientific) was used to conjugate the primary amine group of Nucleic Acid Recognition Moiety 5B/β to the thiol of Bioorthogonal-Effector Partial Moieties 5B and 5β. For each Effector Partial Moiety, 30 nmol of Oligo-5.2 in 100 uL 1×PBS was mixed with 20 molar equivalents of SMCC dissolved in 2 uL DMF. The reaction proceeded at room temperature for 2 hours, then the product was purified over a Sephadex G-15 column (Sigma Aldrich). The activated oligonucleotide was used immediately in a reaction with 30 nmol of azido-peptide productx in 1×PBS. The reactions proceeded for 4 hours at room temperature, then were purified by HPLC. MALDI mass spectrometry analysis gave a product m/z of 7149.6. (expected 7138.20) for Templated Assembly Reactant 5B. MALDI analysis gave a product m/z of 7249.1 (expected 7251.28) for Templated Assembly Reactant 5β.

Treatment of Tumor Cells with Templated Assembly Reactant Sets 5A/5B, and 5α/5β

Templated Assembly Reactants 5A and 5B, and separately 5α and 5β, were tested in HPV E6/E7 RNA positive and negative tumor cell lines for their ability to selectively generate a peptide antigen-specific immune cell response to positive tumor cells. To assay this response:

1. Tumor cell lines were treated with templated assembly reactants, allowing ELA effector structure peptide antigens to form in HPV positive tumors, be proteolytically processed, and get loaded into HLA molecules for display on the surface.

2. T cells specifically recognizing the ELA peptide in HLA were co-cultured with treated tumor cells, resulting in stimulation of the T cells if peptide antigen is present.

3. T cell stimulation level is determined by an IL-2 cytokine release assay.

Tumor Cell Lines

The ELA peptide antigen effector structure created by these templated assembly compounds binds to HLA molecule allele HLA-A2, so all tumor cell lines used in these tests were HLA-A2 positive. Caski cells served as the HPV E6/E7 RNA positive cell line, while HPV negative C33A and U266 cells served as negative controls. Table 14 summarizes the tumor cell lines utilized in Example 5.

TABLE 14

| Cell Line | Origin | HPV Status | HLA-A2 Status |
|---|---|---|---|
| Caski | Cervical carcinoma | Positive | Positive |
| C33A | Cervical carcinoma | Negative | Positive |
| U266 | Myeloma | Negative | Positive |

Compound Administration

For these assays, tumor lines were cultured in 96-well plates, with $5 \times 10^4$ cells seeded per well in a total of 150 uL Roswell Park Memorial Institute 1640 (RPMI-1640) medium. Cells were treated with templated assembly reactants or control ELA peptide on the same day they were seeded in wells. Templated assembly reactants were tested at dosages of 0.1 nanomoles per well and 0.5 nanomoles per well. Control ELA peptide was tested at those levels, as well as at a lower 0.02 nanomoles per well dosage. Templated assembly compounds were dissolved and diluted in 1×PBS before addition to the well. Compounds were administered gymnotically in 1×PBS—no transfection reagent or carrier was used. Several templated assembly reactant administration schemes were evaluated to assess their effect on templating background level:

1. Concurrent administration: templated assembly reactant 5B was added and allowed to disperse in the well, then templated assembly reactant 5A was added within 5 minutes.

2. Staggered administration: templated assembly reactant 5B was added and incubated with cells for 4 hours, then medium was removed. Cells received fresh medium, and templated assembly reactant 5A was added.

3. Staggered administration with Delay: templated assembly reactant 5B was added and incubated with cells for 4 hours, then medium was removed. Cells received fresh medium. Two hours after this medium replacement, templated assembly reactant 5A was added.

Each set of conditions was tested in triplicate wells.

T Cell Administration and Stimulation Assay

ELA-specific T cells were established from Jurkat cells transformed with a cloned T-Cell receptor specifically recognizing ELA bound to HLA-A2, as described in Haggerty et al. 2012 [5]. Immediately after administration of the second template assembly reactant or ELA control peptide, $5 \times 10^4$ of these cells were added to test wells. After co-culture of treated tumor cells and T cells for 20 hours at 37° C., antigen-specific stimulation of T cells was assayed by an ELISA-based IL-2 cytokine release assay as described in [5]. Table 15 summarizes the test conditions evaluated.

TABLE 15

'Simple' refers to the direct addition of control ELAGIGILTV peptide to the test wells.

| ID | Cell line | Treatment | Dosage (nmoles) | Administration | IL-2 Release (Units) |
|---|---|---|---|---|---|
| 1 | None | T cells only | 0 | N/A | 0 |
| 2 | Caski | None | 0 | N/A | 0 |
| 3 | Caski | ELA | 0.02 | Simple | 200 |
| 4 | Caski | ELA | 0.1 | Simple | 325 |
| 5 | Caski | ELA | 0.5 | Simple | 350 |
| 6 | Caski | 5A + 5B | 0.1 | Concurrent | 270 |
| 7 | Caski | 5A + 5B | 0.5 | Concurrent | 275 |
| 8 | Caski | 5A + 5B | 0.1 | Staggered | 62 |
| 9 | Caski | 5A + 5B | 0.5 | Staggered | 125 |
| 10 | Caski | 5A + 5B | 0.1 | Staggered/Delayed | 50 |
| 11 | Caski | 5A + 5B | 0.5 | Staggered/Delayed | 120 |
| 12 | Caski | 5α + 5β | 0.1 | Concurrent | 275 |
| 13 | Caski | 5α + 5β | 0.5 | Concurrent | 290 |
| 14 | Caski | 5α + 5β | 0.1 | Staggered | 50 |
| 15 | Caski | 5α + 5β | 0.5 | Staggered | 130 |
| 16 | Caski | 5α + 5β | 0.1 | Staggered/Delayed | 62 |
| 17 | Caski | 5α + 5β | 0.5 | Staggered/Delayed | 150 |
| 18 | C33A | None | 0 | N/A | 0 |
| 19 | C33A | ELA | 0.02 | Simple | 190 |
| 20 | C33A | ELA | 0.1 | Simple | 250 |
| 21 | C33A | ELA | 0.5 | Simple | 310 |
| 22 | C33A | 5A + 5B | 0.1 | Concurrent | 30 |
| 23 | C33A | 5A + 5B | 0.5 | Concurrent | 60 |
| 24 | C33A | 5α + 5β | 0.1 | Concurrent | 25 |
| 25 | C33A | 5α + 5β | 0.5 | Concurrent | 50 |
| 26 | U266 | None | 0 | N/A | 0 |
| 27 | U266 | ELA | 0.02 | Simple | 125 |
| 28 | U266 | ELA | 0.1 | Simple | 175 |
| 29 | U266 | ELA | 0.5 | Simple | 350 |
| 30 | U266 | 5A + 5B | 0.1 | Concurrent | 40 |
| 31 | U266 | 5A + 5B | 0.5 | Concurrent | 175 |
| 32 | U266 | 5A + 5B | 0.1 | Staggered | 0 |
| 33 | U266 | 5A + 5B | 0.5 | Staggered | 15 |
| 34 | U266 | 5A + 5B | 0.1 | Staggered/Delayed | 0 |
| 35 | U266 | 5A + 5B | 0.5 | Staggered/Delayed | 10 |
| 36 | U266 | 5α + 5β | 0.1 | Concurrent | 40 |
| 37 | U266 | 5α + 5β | 0.5 | Concurrent | 200 |
| 38 | U266 | 5α + 5β | 0.1 | Staggered | 5 |
| 39 | U266 | 5α + 5β | 0.5 | Staggered | 10 |
| 40 | U266 | 5α + 5β | 0.1 | Staggered/Delayed | 0 |
| 41 | U266 | 5α + 5β | 0.5 | Staggered/Delayed | 8 |

Figure 12:
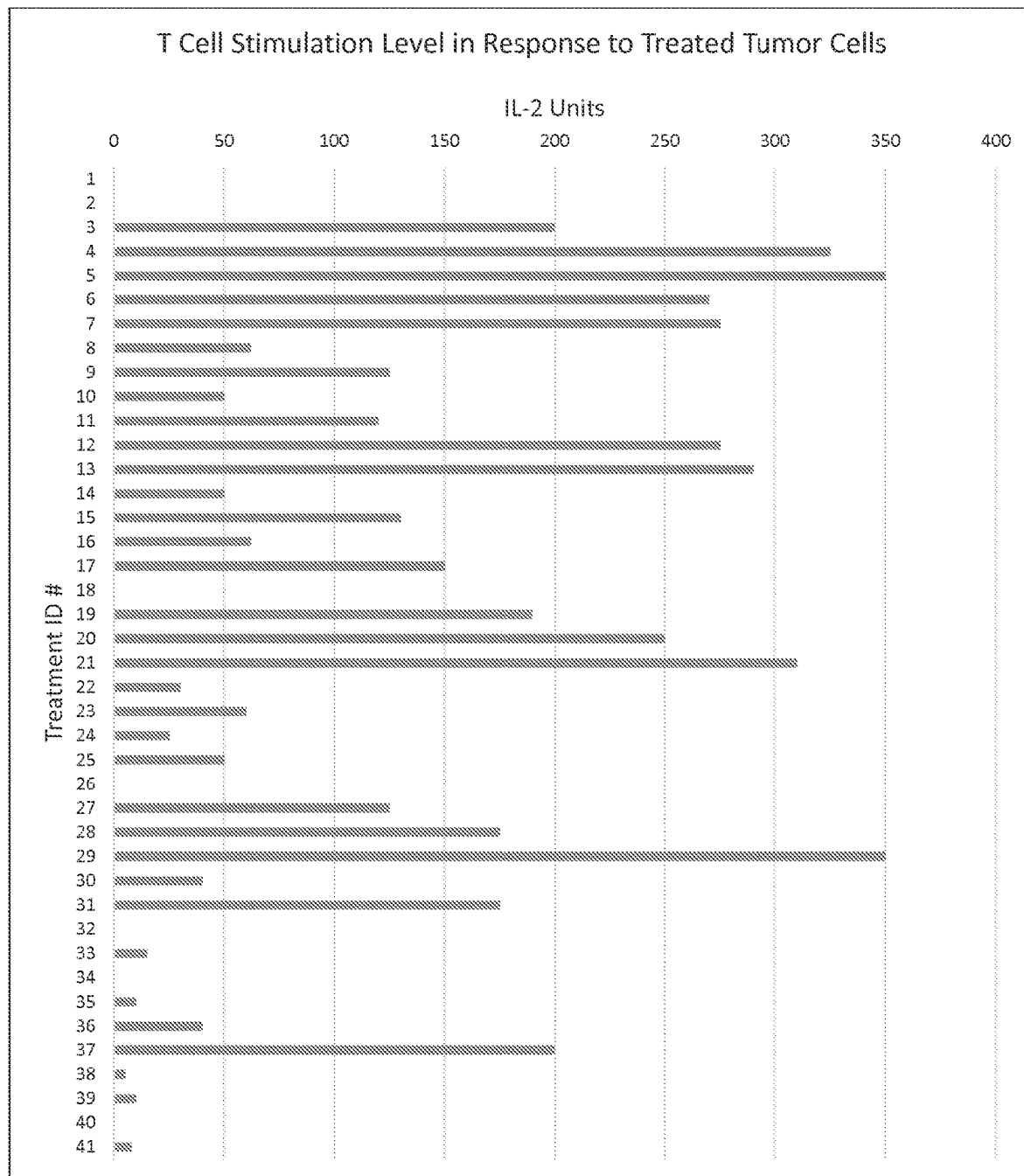
FIG. 12 shows IL-2 release in stimulation of antigen-specific immune effector cells by treated tumor cells.

Results: Stimulation of Antigen-Specific Immune Effector Cells by Treated Tumor Cells FIG. 12 graphs IL-2 release observed in each of the conditions tested. Several conclusions may be drawn from the results:

1. Treatment with templated assembly reactants elicits a selectively stronger T cell response against tumor cells harboring target RNA.

2. Different administration schemes for the two reactants may impact the degree of selectivity of the response. In this case, staggered administration routes improve selectivity by achieving very low background in negative controls.

3. In this example, the two sets of Templated Assembly Reactants performed very similarly, despite having different amino acids conjugated to the bio-orthogonal groups in each case.

The results demonstrate that nucleic acid templated assembly compounds designed to create a peptide antigen in the presence of a tumor-associated RNA may be used to generate a selective response to tumor cells in conjunction with antigen-specific immune cells. Antigen-specific immune cells are selectively stimulated in the presence of treated tumor cells that harbor target RNA. Nucleic acid templated assembly compounds are capable of eliciting an RNA-selective immune cell response to tumor cells.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A pair of targeted templated assembly reactants comprising:
   a first targeted templated assembly reactant comprising:
   a) at least one nucleic acid recognition moiety that binds a target nucleic acid sequence;
   b) at least one effector partial moiety; and
   c) at least one selectively-reactive moiety; and
   a second targeted templated assembly reactant comprising:
   a) at least one nucleic acid recognition moiety that binds a target nucleic acid sequence, wherein the sequence is adjacent to the sequence to which the nucleic acid recognition moiety of the first targeted templated assembly reactant binds;
   b) at least one effector partial moiety; and
   c) at least one selectively-reactive moiety;
   wherein the selectively-reactive moiety of the first targeted templated assembly reactant is reactable with the selectively-reactive moiety of the second targeted templated assembly reactant,
   wherein the target nucleic acid sequence is selected from a cancer-specific nucleic acid sequence, a viral nucleic acid sequence, a microbial-specific nucleic acid sequence, a differentially expressed gene, a disease-specific nucleic acid sequence, and a fragment, portion or a nucleic acid gene product thereof;
   wherein the reaction between the selectively-reactive moiety of the first targeted templated assembly reactant and the selectively-reactive moiety of the second targeted templated assembly reactant forms a covalent bond between the selectively-reactive moiety of the first targeted templated assembly reactant and the selectively-reactive moiety of the second targeted templated assembly reactant; and
   wherein the effector partial moiety of the first targeted templated assembly reactant and the effector partial moiety of the second targeted templated assembly reactant produce an active effector structure, and wherein each effector partial moiety is selected from the group consisting of a peptide, a non-active portion of a peptidomimetic structure, and a non-active portion of a drug.

2. The pair of targeted templated assembly reactants of claim 1, wherein the nucleic acid recognition moiety of each targeted templated assembly reactant is a nucleic acid-binding oligomer or a nucleic acid oligomer that hybridizes to the target nucleic acid sequence.

3. The pair of targeted templated assembly reactants of claim 1, wherein the selectively-reactive moiety of each targeted templated assembly reactant is biologically inert or a bio-orthogonal reactive molecule.

4. The pair of targeted templated assembly reactants of claim 3, wherein each bio-orthogonal reactive molecule is selected from the group consisting of an azide, a cyclooctyne, a nitrone, a norbornene, an oxanorbornadiene, a phosphine, a dialkyl phosphine, a trialkyl phosphine, a phosphinothiol, a phosphinophenol, a cyclooctene, a nitrile oxide, a thioester, a tetrazine, an isonitrile, a tetrazole, and a quadricyclane.

5. The pair of targeted templated assembly reactants of claim 1, wherein the selectively-reactive moiety of each targeted templated assembly reactant is linked to the nucleic acid recognition moiety.

6. The pair of targeted templated assembly reactants of claim 1, wherein the active effector structure is a ligand for an antibody or antibody fragment or T cell receptor.

7. The pair of targeted templated assembly reactants of claim 6, wherein the antibody fragment is an scFv.

8. The pair of targeted templated assembly reactants of claim 1 further comprising a chemical linker between any of the nucleic acid recognition moiety and the selectively-reactive moiety, and the selectively-reactive moiety and the effector partial moiety, wherein the chemical linker is at least one of a flexible moiety, cleavage site, and chemical modification site.

9. The pair of targeted templated assembly reactants of claim 1, wherein the nucleic acid recognition moiety of each targeted templated assembly reactant is an oligomer selected from the group consisting of DNA nucleotides, RNA nucleotides, phosphorothioate-modified nucleotides, 2-O-alkylated RNA nucleotides, halogenated nucleotides, locked nucleic acid nucleotides (LNA), peptide nucleic acids (PNA), morpholino nucleic acid analogues (morpholinos), pseudouridine nucleotides, xanthine nucleotides, hypoxanthine nucleotides, 2-deoxyinosine nucleotides, other nucleic acid analogues capable of base-pair formation, and combinations thereof.

10. The pair of targeted templated assembly reactants of claim 1, wherein each effector partial moiety is a peptide.

11. The pair of targeted templated assembly reactants of claim 1, wherein the active effector structure is a ligand for an antibody or antibody fragment.

12. The pair of targeted templated assembly reactants of claim 1, wherein the target nucleic acid sequence is a cancer-specific nucleic acid sequence, a viral nucleic acid sequence, a microbial-specific nucleic acid sequence, or a disease-specific nucleic acid sequence.

13. The pair of targeted templated assembly reactants of claim 1, wherein the target nucleic acid sequence is a cancer-specific nucleic acid sequence or a disease-specific nucleic acid sequence.

14. The pair of targeted templated assembly reactants of claim 1, wherein the target nucleic acid sequence is present in a pathogenic cell.

15. The pair of targeted templated assembly reactants of claim 1, wherein the active effector structure is the ELA peptide epitope.

* * * * *

SEQUENCE LISTING

<160> NUMBER OF SEQ ID NOS: 12

<210> SEQ ID NO 1
<211> LENGTH: 56
<212> TYPE: DNA
<213> ORGANISM: Artificial Sequence
<220> FEATURE:
<223> OTHER INFORMATION: Oligo sequence

<400> SEQUENCE: 1
taactgtcaa aagccactgt gtcctgaaga aaagcaaaga catctggaca aaaagc    56

<210> SEQ ID NO 2
<211> LENGTH: 15
<212> TYPE: DNA

-continued

<213> ORGANISM: Artificial Sequence
<220> FEATURE:
<223> OTHER INFORMATION: Oligo sequence

<400> SEQUENCE: 2
ccagatgtct ttgct                                                        15

<210> SEQ ID NO 3
<211> LENGTH: 16
<212> TYPE: DNA
<213> ORGANISM: Artificial Sequence
<220> FEATURE:
<223> OTHER INFORMATION: Oligo sequence

<400> SEQUENCE: 3
tttcttcagg acacag                                                       16

<210> SEQ ID NO 4
<211> LENGTH: 50
<212> TYPE: DNA
<213> ORGANISM: Artificial Sequence
<220> FEATURE:
<223> OTHER INFORMATION: Oligomer

<400> SEQUENCE: 4
cggaatataa gctggtggtg gtgggcgccg tcggtgtggg caagagtgcg                  50

<210> SEQ ID NO 5
<211> LENGTH: 50
<212> TYPE: DNA
<213> ORGANISM: Artificial Sequence
<220> FEATURE:
<223> OTHER INFORMATION: Oligomer

<400> SEQUENCE: 5
cggaatataa gctggtggtg gtgggcgccg gcggtgtggg caagagtgcg                  50

<210> SEQ ID NO 6
<211> LENGTH: 50
<212> TYPE: DNA
<213> ORGANISM: Artificial Sequence
<220> FEATURE:
<223> OTHER INFORMATION: Oligomer

<400> SEQUENCE: 6
gggttacgtg gaggcgctct gtgaattgag tgagcaggcg gggtgggcca                  50

<210> SEQ ID NO 7
<211> LENGTH: 11
<212> TYPE: DNA
<213> ORGANISM: Artificial Sequence
<220> FEATURE:
<223> OTHER INFORMATION: Oligomer

<400> SEQUENCE: 7
acaccgacgg c                                                            11

<210> SEQ ID NO 8
<211> LENGTH: 11
<212> TYPE: DNA
<213> ORGANISM: Artificial Sequence
<220> FEATURE:
<223> OTHER INFORMATION: Oligomer

<400> SEQUENCE: 8
cccaccacca c                                                            11

```
<210> SEQ ID NO 9
<211> LENGTH: 15
<212> TYPE: RNA
<213> ORGANISM: Artificial Sequence
<220> FEATURE:
<223> OTHER INFORMATION: Oligomer

<400> SEQUENCE: 9
ccagaugucu uugcu                                                    15

<210> SEQ ID NO 10
<211> LENGTH: 16
<212> TYPE: RNA
<213> ORGANISM: Artificial Sequence
<220> FEATURE:
<223> OTHER INFORMATION: Oligomer

<400> SEQUENCE: 10
uuucuucagg acacag                                                   16

<210> SEQ ID NO 11
<211> LENGTH: 15
<212> TYPE: RNA
<213> ORGANISM: Artificial Sequence
<220> FEATURE:
<223> OTHER INFORMATION: Oligomer

<400> SEQUENCE: 11
ccagaugucu uugcu                                                    15

<210> SEQ ID NO 12
<211> LENGTH: 16
<212> TYPE: RNA
<213> ORGANISM: Artificial Sequence
<220> FEATURE:
<223> OTHER INFORMATION: Oligomer

<400> SEQUENCE: 12
uuucuucagg acacag                                                   16
```